(12) United States Patent
Hayashi et al.

(10) Patent No.: US 8,673,590 B2
(45) Date of Patent: Mar. 18, 2014

(54) METHOD FOR PRODUCING DIPEPTIDE

(75) Inventors: Mikiro Hayashi, Ibaraki (JP); Kazuhiko Tabata, Ibaraki (JP); Makoto Yagasaki, Yamaguchi (JP); Yoshiyuki Yonetani, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 317 days.

(21) Appl. No.: 12/594,903

(22) PCT Filed: Apr. 4, 2008

(86) PCT No.: PCT/JP2008/056758
§ 371 (c)(1),
(2), (4) Date: Oct. 6, 2009

(87) PCT Pub. No.: WO2008/126783
PCT Pub. Date: Oct. 23, 2008

(65) Prior Publication Data
US 2010/0129867 A1 May 27, 2010

(30) Foreign Application Priority Data
Apr. 6, 2007 (JP) ................................ 2007-099956

(51) Int. Cl.
*C07K 5/06* (2006.01)
*C07K 14/195* (2006.01)
*C12P 21/02* (2006.01)

(52) U.S. Cl.
USPC ............ 435/69.1; 435/252.3; 435/31; 435/34; 435/30; 435/33

(58) Field of Classification Search
None
See application file for complete search history.

(56) References Cited

U.S. PATENT DOCUMENTS

| | | |
|---|---|---|
| 6,303,348 B1 | 10/2001 | Livshits et al. |
| 6,858,406 B1 | 2/2005 | Vrljic et al. |
| 2003/0113899 A1 | 6/2003 | Yamaguchi et al. |
| 2004/0171106 A1 | 9/2004 | Hashimoto et al. |
| 2005/0106703 A1 | 5/2005 | Hashimoto et al. |
| 2005/0148048 A1 | 7/2005 | Hashimoto et al. |
| 2005/0221453 A1 | 10/2005 | Takagi et al. |
| 2005/0239177 A1 | 10/2005 | Livshits et al. |
| 2005/0287626 A1 | 12/2005 | Hashimoto et al. |
| 2005/0287627 A1 | 12/2005 | Hashimoto et al. |
| 2006/0019355 A1 | 1/2006 | Ueda et al. |
| 2007/0128687 A1 | 6/2007 | Ikeda et al. |
| 2007/0243581 A1 | 10/2007 | Hashimoto et al. |
| 2008/0213827 A1 | 9/2008 | Hashimoto et al. |

FOREIGN PATENT DOCUMENTS

| | | |
|---|---|---|
| EP | 1 616 963 A2 | 1/2006 |
| JP | 2000-116390 A | 4/2000 |
| JP | 2000-189177 A | 7/2000 |
| JP | 2005-237379 A | 9/2005 |
| JP | 2005-287333 A | 10/2005 |
| WO | WO 97/23597 A2 | 7/1997 |
| WO | WO 2004/058960 A1 | 7/2004 |
| WO | WO 2005/045006 A1 | 5/2005 |
| WO | WO 2005/052153 A1 | 6/2005 |
| WO | WO 2005/052177 A1 | 6/2005 |
| WO | WO 2005/103260 A1 | 11/2005 |
| WO | WO 2006/001379 A1 | 1/2006 |
| WO | WO 2006/001381 A1 | 1/2006 |
| WO | WO 2006/001382 A1 | 1/2006 |

OTHER PUBLICATIONS

Degrassi et al., *Current Microbiology*, 45(4): 250-254 (2002).
Hayashi et al., *FEMS Microbiol. Letters*, 304(1): 12-19 (2010).
Olson et al., *Journal of Bacteriology*, 173(1): 234-244 (Jan. 1991).
Park et al., *The Journal of Biological Chemistry*, 272(14): 9210-9214 (1997).
Tabata et al., *Journal of Bacteriology*, 187(15): 5195-5202 (Aug. 2005).
Yamada et al., *Applied and Environmental Microbiology*, 72(7): 4735-4742 (Jul. 2006).
Bentley et al., *Gene*, 127: 117-120 (1993).
Delgado et al., *Journal of Bacteriology*, 187(10): 3465-3470 (May 2005).
Nishino et al., *Journal of Bacteriology*, 183(20): 5803-5812 (Oct. 2001).
Riley et al., *Nucleic Acids Research*, 34(1): 1-9 (2006).
Smith et al., *Microbiology*, 145: 2891-2901 (1999).
Tabata et al., *Applied and Environmental Microbiology*, 73(20): 6378-6385 (Oct. 2007).
Tabata et al., Japan Society for Bioscience, Biotechnology, and Agrochemistry 2006 Nendo Taikai Koen Yoshishu, p. Shi72 (Mar. 5, 2006).
Yang et al., *Journal of Antimicrobial Chemotherapy*, 51: 545-556 (2003).
Sequence Listing for International Patent Application Publication WO 2005/103260.
Sequence Listing for International Patent Application Publication WO 2006/001379.
Sequence Listing for International Patent Application Publication WO 2006/001381.
Sequence Listing for International Patent Application Publication WO 2006/001382.

*Primary Examiner* — Kagnew H Gebreyesus
(74) *Attorney, Agent, or Firm* — Leydig, Voit & Mayer, Ltd.

(57) ABSTRACT

The invention provides a microorganism having an ability to produce a protein having a dipeptide synthesizing activity and in which an activity of the protein to transport a dipeptide in a microbial cell to the outside of the microbial cell is higher than that of a parental strain.

8 Claims, No Drawings

METHOD FOR PRODUCING DIPEPTIDE

CROSS-REFERENCE TO RELATED APPLICATIONS

This patent application is the U.S. national phase of International Patent Application PCT/JP2008/056758, filed Apr. 4, 2008, which claims the benefit of Japanese Patent Application 2007-099956, filed Apr. 6, 2007, the contents of which are hereby incorporated by reference in their entireties.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 141,827 bytes ASCII (Text) file named "705524SequenceListing.txt," created Oct. 6, 2009.

TECHNICAL FIELD

The present invention relates to a microorganism having an ability to produce a protein having a dipeptide synthesizing activity, and in which an activity of a protein to transport a dipeptide in the microbial cell to the outside of the microbial cell is higher than that of a parental strain, and a process for producing a dipeptide using the microorganism.

BACKGROUND ART

As a process for producing a dipeptide wherein two L-amino acids are linked by α-bond, a process utilizing a ywfE gene product which is one of the synthases of bacilysin, a dipeptide antibiotic derived from a microorganism belonging to the genus *Bacillus*, is known (patent documents 1-8).

As a method of improving a producing ability of a strain in L-amino acid fermentation, a method including altering an efflux system for L-amino acid in a microbial cell is known (patent documents 9-14). In addition, the presence of an efflux system for Microcin J25, a peptidic antibiotic, is also known (non-patent document 1).

Also in the production of a dipeptide, dipeptide productivity is considered to be improved by enhancing the activity of a dipeptide exporting system, namely, a protein having an activity to transport a dipeptide in the microbial cell to the outside of the microbial cells (hereinafter to be referred to as a dipeptide transporting activity). However, a protein having a dipeptide transporting activity has not been reported heretofore.

It is known that bcr gene of *Escherichia coli* is a gene encoding membrane protein which relates to bicyclomycin resistance (non-patent document 2), and norE gene is a gene encoding an efflux pump which relates to quinolone resistance (non-patent document 3). emrD gene has been reported as a gene encoding an SDS transporting protein (non-patent document 4). ydeE gene is predicted to be a gene encoding a drug transporting protein, but its activity has not been confirmed (non-patent document 4). The function of yeeO gene is completely unknown.

patent document 1: WO 2004/058960
patent document 2: WO 2005/045006
patent document 3: WO 2005/052153
patent document 4: WO 2005/052177
patent document 5: WO 2005/103260
patent document 6: WO 2006/001379
patent document 7: WO 2006/001381
patent document 8: WO 2006/001382
patent document 9: WO 97/23597 A2
patent document 10: US 2003/0113899 A1
patent document 11: JP-A-2000-116390
patent document 12: JP-A-2000-189177
patent document 13: JP-A-2005-287333
patent document 14: JP-A-2005-237379
non-patent document 1: J. Bacteriol., 187, 3465-3470 (2005)
non-patent document 2: Gene, 127, 117-120 (1993)
non-patent document 3: J. Antimicrob. Chemother., 51, 545-56 (2003)
non-patent document 4: J. Bacteriol., 183, 5803-5812 (2001)

DISCLOSURE OF THE INVENTION

Problems to be Solved by the Invention

The present invention aims to provide a microorganism which produces a dipeptide efficiently and a process for producing a dipeptide using the microorganism.

Means of Solving the Problems

The present invention relates to the following (1)-(6).

(1) A microorganism having an ability to produce a protein having a dipeptide synthesizing activity and
in which an activity of a protein to transport a dipeptide in a microbial cell is higher than that of a parental strain, wherein said protein having a dipeptide transporting activity is described in any of the following [1] to [3]:
[1] a protein having an amino acid sequence shown by any of SEQ ID NOs: 6 to 10
[2] a protein consisting of an amino acid sequence wherein one or more amino acids are deleted, substituted or added in the amino acid sequence shown by any of SEQ ID NOs: 6 to 10, and having a dipeptide transporting activity,
[3] a protein having an amino acid sequence having 80% or more homology with the amino acid sequence shown by any of SEQ ID NOs: 6 to 10, and having a dipeptide transporting activity.
(2) The microorganism of the above-mentioned (1), which is obtained by transforming the parental strain with a DNA described in any of the following [1] to [3]:
[1] a DNA encoding a protein of any of [1] to [3] in the above-mentioned (1),
[2] a DNA having a nucleotide sequence of a coding region in the nucleotide sequence shown by any of SEQ ID NOs: 1 to 5,
[3] a DNA hybridizing with a DNA consisting of a nucleotide sequence which is complementary to a nucleotide sequence of a coding region in the nucleotide sequence shown by any of SEQ ID NOs: 1 to 5 under stringent conditions, and encoding the protein having a dipeptide transporting activity.
(3) The microorganism of the above-mentioned (1) or (2), which belongs to the genus *Escherichia*, *Corynebacterium*, *Bacillus*, *Serratia*, *Pseudomonas* or *Streptomyces*.
(4) A process for producing a dipeptide which comprises: allowing a culture or a treated culture of the microorganism of any one of the above-mentioned (1) to (3) and an amino acid, amino acid ester or amino acid amide to be present in an aqueous medium, allowing the dipeptide to form and accumulate in the aqueous medium and recovering the dipeptide from the aqueous medium.
(5) A process for producing a dipeptide which comprises: culturing the microorganism of the above-mentioned (1) or (2) and which has an ability to produce at least one kind of amino acid out of amino acids constituting the dipeptide in a medium, allowing the dipeptide to form and accumulate in the medium, and recovering the dipeptide from the culture.

(6) The process of the above-mentioned (4) or (5), wherein the microorganism belongs to the genus *Escherichia, Corynebacterium, Bacillus, Serratia, Pseudomonas* or *Streptomyces*.

Effect of the Invention

According to the present invention, by enhancing the activity of a protein having a transporting activity of dipeptide in a microbial cell of a microorganism to the outside of the microbial cell, dipeptide can be efficiently produced using the microorganism.

BEST MODE FOR CARRYING OUT THE INVENTION

1. Microorganism of the Present Invention (1) Microorganism Wherein a Dipeptide Transporting Activity is Higher than that of Parental Strain Examples of the microorganism wherein the activity of a protein having a dipeptide transporting activity is higher than that of a parental strain include (a) i) a microorganism wherein the specific activity of the protein is improved as compared to the parental strain, and ii) a microorganism showing an improved production amount of the protein having a dipeptide transporting activity as compared to the parental strain, which is obtained by modifying a gene on the chromosomal DNA of the parental strain, and encodes the protein having a dipeptide transporting activity, and (b) a microorganism obtained by transforming the parental strain with a DNA encoding a protein having a dipeptide transporting activity. The parental strain in the present specification is the original strain to be the target of modification or transformation, and may be a wild strain or a mutant. Examples of the parental strain include when the microorganism is *Escherichia coli*, wild strain such as *E. coli* K-12 strain, B strain and B/r strain, or a mutant thereof. Example of the mutant include *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415 and the like.

Examples of the protein having a dipeptide transporting activity include a protein of any of the following [1]-[3],

[1] a protein having an amino acid sequence shown by any of SEQ ID NOs: 6 to 10,
[2] a protein consisting of an amino acid sequence wherein one or more amino acids are deleted, substituted or added in the amino acid sequence shown by any of SEQ ID NOs: 6 to 10, and having a dipeptide transporting activity, and
[3] a protein having an amino acid sequence having 80% or more homology with amino acid sequence shown by any of SEQ ID NOs: 6 to 10 and having a dipeptide transporting activity.

The above protein consisting of an amino acid sequence wherein one or more amino acid residues are deleted, substituted or added and having a dipeptide transporting activity can be obtained, for example, by introducing a site-directed mutation into DNA encoding a protein consisting of the amino acid sequence of any of SEQ ID NOs: 6 to 10 by site-directed mutagenesis described in Molecular Cloning, A Laboratory Manual, Third Edition, Cold Spring Harbor Laboratory Press (1989) (hereinafter referred to as Molecular Cloning, Third Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited, but is within the range where deletion, substitution or addition is possible by known methods such as the above-mentioned site-directed mutagenesis. The number is 1 to dozens, preferably 1 to 20, more preferably 1 to 10, further preferably 1 to 5.

The expression "one or more amino acid residues are deleted, substituted or added in the amino acid sequence shown by SEQ ID NOs: 6 to 10" means that the amino acid sequence may contain deletion, substitution or addition of a single or plural amino acid residues at an arbitrary position therein.

Deletion or addition of amino acid residues may be contained, for example, in the N-terminal or C-terminal one to 10 amino acid residue of the amino acid sequence of any of SEQ ID NOs: 6 to 10.

Deletion, substitution and addition may be simultaneously contained in one sequence, and amino acids to be substituted or added may be either natural or not. Examples of the natural amino acids are L-alanine, L-asparagine, L-aspartic acid, L-arginine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine
Group B: aspartic acid, glutamic acid, isoaspartic acid, isoglutamic acid, 2-aminoadipic acid, 2-aminosuberic acid
Group C: asparagine, glutamine
Group D: lysine, arginine, ornithine, 2,4-diaminobutanoic acid, 2,3-diaminopropionic acid
Group E: proline, 3-hydroxyproline, 4-hydroxyproline
Group F: serine, threonine, homoserine
Group G: phenylalanine, tyrosine In addition, examples of the protein having the dipeptide transporting activity include a protein consisting of an amino acid sequence having 80% or more, preferably 90% or more, more preferably 95% or more, further preferably 97% or more, particularly preferably 98% or more, most preferably 99% or more homology with amino acid sequence shown by any of SEQ ID NOs: 6 to 10, and a protein having the dipeptide transporting activity.

The homology among amino acid sequences and nucleotide sequences can be determined by using algorithm BLAST by Karlin and Altschul [Pro. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are well known.

That the protein consisting of an amino acid sequence, wherein one or more amino acids are deleted, substituted or added in the amino acid sequence shown by SEQ ID NOs: 6 to 10, has a dipeptide transporting activity can be confirmed, for example, by preparing a transformant having a higher activity of the protein than that of the parental strain by transforming the parental strain with a DNA encoding the protein to be confirmed for the activity, adding culture of the parental strain or the transformed strain and amino acids constituting the object dipeptide to a buffer, and comparing the amounts of the dipeptide formed and accumulated in the aqueous medium.

Examples of the microorganism of the above-mentioned (a) i), having an improved specific activity of the protein having a dipeptide transporting activity as compared to that of the parental strain, include a microorganism containing a mutant protein improved in the activity as compared to that of the protein having a dipeptide transporting activity of the parental strain, since the protein has the amino acid sequence, wherein one or more amino acid, preferably 1-10 amino acids, more preferably 1-5 amino acids, still more preferably 1-3 amino acids, are substituted in the amino acid sequence of the protein of the parental strain.

Examples of the microorganism improved in the production amount of the protein having a dipeptide transporting activity as compared to the parental strain in the above-mentioned (a) ii) include a microorganism showing an improved production amount of the protein as compared to the protein having a dipeptide transporting activity of the parental strain, since it has a promoter region wherein not less than one base, preferably 1 to 10 bases, more preferably 1 to 5 bases, still more preferably 1 to 3 bases, are substituted in the nucleotide sequence of the transcription regulatory region or promoter region of the gene encoding the protein, which is present on the chromosomal DNA of the parental strain.

Examples of the microorganism obtained by transforming the parental strain of the above-mentioned (b) with a DNA encoding the protein having a dipeptide transporting activity include a microorganism obtained by transforming the parental strain with

[4] a DNA encoding a protein of any of the above-mentioned [1] to [3],

[5] a DNA having a nucleotide sequence of the coding region in the nucleotide sequence shown by any of SEQ ID NOs: 1 to 5, or

[6] a DNA hybridizing with a DNA consisting of a nucleotide sequence complementary to a nucleotide sequence of a coding region in the nucleotide sequence shown by any of SEQ ID NOs: 1 to 5 under stringent conditions, and encoding the protein having a dipeptide transporting activity.

Examples of the microorganism include i) a microorganism having an exogenous DNA encoding a protein having a dipeptide transporting activity on the chromosomal DNA and ii) a microorganism having an exogenous DNA encoding a protein having a dipeptide transporting activity outside the chromosome. In other words, the microorganism of i) means that the parental strain does not have a DNA encoding a protein having a dipeptide transporting activity and one or more newly-introduced DNAs are present on the chromosomal DNA, or the parental strain intrinsically has a DNA encoding a protein having a dipeptide transporting activity, and two or more DNAs encoding a protein having a dipeptide transporting activity, which includes the newly-introduced DNA, are present on the chromosomal DNA. The microorganism of ii) is a microorganism having a DNA encoding a protein having a dipeptide transporting activity on the plasmid DNA.

"To hybridize" in the above refers to a step of hybridization of DNA with DNA having a specific nucleotide sequence or a part of the DNA. Therefore, the DNA having a specific nucleotide sequence or a part of the DNA can be used as a probe for Northern or Southern blot analysis or can be used as an oligonucleotide primer for PCR analysis. DNAs used as a probe include DNAs comprising at least 100 or more bases, preferably 200 or more bases, more preferably 500 or more bases, and DNAs used as a primer include DNAs comprising at least 10 or more bases, preferably 15 or more bases.

The methods of hybridization experiments of DNA are well known and, for example, those of ordinary skill in the art can determine the hybridization conditions according to the description of the specification of the present application. The hybridization conditions can be employed according to many standard textbooks, including the description in Molecular Cloning Second Edition, Third Edition (2001), Methods for General and Molecular Bacteriolgy, ASM Press (1994) and Immunology methods manual, Academic press (Molecular).

Hybridization under the above stringent conditions is carried out, for example, as follows. A filter and a probe DNA are incubated in a solution comprising 50% formamide, 5×SSC (750 mmol/l sodium chloride and 75 mmol/l sodium citrate), 50 mmol/l sodium phosphate (pH 7.6), 5×Denhardt's solution, 10% dextran sulfate and 20 µg/l denatured salmon sperm DNA at 42° C. overnight, and after the incubation, for example, the filter is preferably washed in 0.2×SSC solution at about 65° C. Less stringent conditions can also be employed. Modification of the stringent conditions can be made by adjusting the concentration of formamide (the conditions become less stringent as the concentration of formamide is lowered) and by changing the salt concentrations and the temperature conditions. Hybridization under less stringent conditions is carried out, for example, by incubating a filter with DNA immobilized thereon and a probe DNA in a solution comprising 6×SSCE (20×SSCE: 3 mol/l sodium chloride, 0.2 mol/l sodium dihydrogenphosphate and 0.02 mol/l EDTA, pH 7.4), 0.5% SDS, 30% formamide and 100 µg/l denatured salmon sperm DNA at 37° C. overnight, and washing the filter with 1×SSC solution containing 0.1% SDS at 50° C. Hybridization under still less stringent conditions is carried out by hybridization under the above less stringent conditions using a solution having a high salt concentration (for example, 5×SSC), and washing the filter.

Various conditions described above can also be established by adding a blocking reagent used to reduce the background of hybridization or changing the reagent. The addition of the above blocking reagent may be accompanied by changes of conditions for hybridization to make the conditions suitable for the purpose.

The above DNA capable of hybridization under stringent conditions includes DNA having at least 90% or more, preferably 95% or more, more preferably 97% or more, further preferably 98% or more, particularly preferably 99% or more homology to the DNA having nucleotide sequence of coding region of nucleotide sequence of any of SEQ ID NOs: 1 to 5 as calculated by use of programs such as BLAST and FASTA described above based on the above parameters.

(2) Microorganism Having an Ability to Produce a Protein Having Dipeptide Synthesizing Activity The microorganism having an ability to produce a protein having a dipeptide synthesizing activity is not particularly limited as long as it has the ability. Examples thereof include a microorganism that produces a protein having an activity to synthesize dipeptide by condensing and ligating one or more kinds of amino acids [hereinafter to be referred to as L-amino acid ligase (EC 6.3.2.28)], a microorganism that produces a protein having an activity to synthesize dipeptide from L-amino acid ester and L-amino acid, a microorganism that produces a protein having an activity to synthesize dipeptide from L-amino acid amide and L-amino acid and the like.

Examples of the microorganism that produces a protein having an activity to synthesize dipeptide by condensing and ligating one or more kinds of amino acids include a microorganism that produces a protein selected from the group consisting of Non-Ribosomal Peptide Synthetase (NRPS), D-Ala-D-Ala ligase and L-amino acid ligase.

Examples of the microorganism that produces NRPS include prokaryotes including *Bacillus*, eucaryotes including *Penicillium*, microorganisms that produce BacA, BacB and BacC (GenBank AF007865), microorganisms that produce TycA, TycB and TycC (GenBank AF004835), a microorganism that produces PcbAB (GenBank M57425), and a microorganism that produces a protein having 80% or more, preferably 90% or more, more preferably 95% or more homology, with the amino acid sequence of a protein selected from BacA, BacB, BacC, TycA, TycB, TycC and PcbAB and having the activity of NRPS, and the like.

Examples of the microorganism that produces D-Ala-D-Ala ligase include a procaryote forming peptidoglycan, a microorganism that produces DdlA (GenBank accession no. M58467), a microorganism that produces DdlB (GenBank accession no. AE000118), a microorganism that produces DdlC (GenBank accession no. D88151), and a microorganism that produces a protein having an amino acid sequence wherein one or more amino acids are deleted, substituted or added in amino acid sequence of any selected from DdlA, DdlB and DdlC, and having a D-Ala-D-Ala ligase activity, and the like.

The homology of the amino acid sequence can be determined using a program such as the above-mentioned BLAST, FASTA and the like.

Examples of the microorganism that produces L-amino acid ligase include microorganisms belonging to the genus *Bacillus*, preferably *Bacillus subtilis, Bacillus amyloliquefaciens, Bacillus coagulans, Bacillus licheniformis, Bacillus megaterium, Bacillus pumilus*, and the microorganism that produces the protein described in WO 2004/058960.

Examples of the L-amino acid ligase include microorganisms capable of producing a protein selected from the following [7] to [10]:

[7] A protein consisting of an amino acid sequence shown by any of SEQ ID NOs: 11 to 18,

[8] A protein consisting of an amino acid sequence, wherein one or more amino acids are deleted, substituted or added in the amino acid sequence shown by any of SEQ ID NOs: 11 to 18, and having an L-amino acid ligase activity,

[9] A protein consisting of an amino acid sequence having 80% or more, preferably 90% or more, more preferably 95% or more, still more preferably 97% or more, particularly preferably 98% or more, most preferably 99% or more homology, with the amino acid sequence shown by any of SEQ ID NOs: 11 to 18, and having an L-amino acid ligase activity, and

[10] A protein having an amino acid sequence having 80% or more, preferably 90% or more, more preferably 95% or more, still more preferably 97% or more, particularly preferably 98% or more, most preferably 99% or more homology, with the amino acid sequence shown by SEQ ID NO: 19, and having an L-amino acid ligase activity.

Examples of the microorganism that produces a protein having an activity to synthesize dipeptide from L-amino acid ester and L-amino acid include a microorganism that produces proline imino peptidase; specifically, microorganisms belonging to the genus *Bacillus, Corynebacterium, Pseudomonas*, and the like. Specifically, examples of the microorganism include *Bacillus subtilis* ATCC6633, *Bacillus coagulans* EK01[J. Bacteriol., 174, 7919 (1992)], *Corynebacterium glutamicum* ATCC13286, *Pseudomonas putida* AJ-2402 (FERN BP-8101), *Pseudomonas putida* ATCC12633, *Pseudomonas putida* AJ2048(FERM BP-8123) (above-mentioned microorganisms are described in WO 03/010307) and the like. Examples of proline imino peptidase producing microorganism include *Arthrobacter nicotianae* [FEMS Microbiol. Lett., 78, 191 (1999)], *Escherichia coli* (JP-A-2-113887), *Flavobacterium meningosepticum* [Arch. Biochem. Biophys., 336, 35 (1996)], *Hafnia alvei* [J. Biochem., 119, 468 (1996)], *Lactobacillus delbrueckii* [Microbiology, 140, 527 (1994)], *Bacillus coagulans* [J. Bacteriol., 174, 7919 (1994)], *Aeromonas sobria* [J. Biochem., 116, 818 (1994)], *Xanthomonas campestris* (JP-A-9-121860), *Neisseria gonorrhoeae* [Mol. Microbiol., 9, 1203 (1993)], *Propionibacterium freudenreichii* [Appl. Environ. Microbiol., 64, 4736 (1998)], *Serratia marcescens* [J. Biochem., 122, 601 (1997)], *Corynebacterium variabilis* [J. Appl. Microbiol., 90, 449 (2001)], *Thermoplasma acidophilum* [FEBS Lett., 398, 101 (1996)], *Pseudomonas aeruginosa* [Nature, 406, 959 (2000)] and the like.

Furthermore, examples of the microorganism that produces proline imino peptidase include a microorganism having an ability to produce a protein selected from the following [11]-[13],

[11] proline imino peptidase described in any of WO 03/010307, FEMS Microbiol. Lett., 78, 191 (1999), JP-A-2-113887, Arch. Biochem. Biophys., 336, 35 (1996), J. Biochem., 119, 468 (1996), Microbiology, 140, 527 (1994), J. Bacteriol., 174, 7919 (1994), J. Biochem., 116, 818 (1994), JP-A-9-121860, Mol. Microbiol., 9, 1203 (1993), Appl. Environ. Microbial., 64, 4736 (1998), J. Biochem., 122, 601 (1997), FEBS Lett., 398, 101 (1996), and Nature, 406, 959 (2000),

[12] a protein consisting of an amino acid sequence, wherein one or more amino acids are deleted, substituted or added in the amino acid sequence above-mentioned proline imino peptides of [11], and having a proline imino peptidase activity, and

[13] a protein consisting of an amino acid sequence having 80% or more, preferably 90% or more, more preferably 95% or more, still more preferably 97% or more, particularly preferably 98% or more, most preferably 99% or more homology, with the amino acid sequence of any of the above-mentioned proline imino peptidases of [11], and having a proline imino peptidase activity.

Examples of the microorganism that produces a protein having an activity to synthesize dipeptide from L-amino acid amide and L-amino acid include a microorganism that produces L-amino acid amide hydrolase; specifically, microorganisms belonging to the genus *Bacillus, Corynebacterium, Erwinia, Rhodococcus, Chryseobacterium, Micrococcus, Pseudomonas, Cryptococcus, Trichosporon, Rhodosporidium, Sporobolomyces, Tremella, Torulaspora, Sterigmatomyces*, and *Rhodotorula*, preferably microorganism belonging to the genus *Bacillus, Corynebacterium* and *Pseudomonas*, more preferably *Bacillus megaterium* AJ3284 (FERM BP-8090), *Corynebacterium glutamicum* ATCC13286, *Micrococcus luteus* ATCC9341, *Pseudomonas*

*saccharophila* ATCC15946 (the above microorganisms are described in WO 03/010187) and the like.

In addition, examples of the microorganism that produces a protein having an L-amino acid amide hydrolase activity include a microorganism having an ability to produce a protein selected from the following [14]-[16]:

[14] L-amino acid amide hydrolase described in WO 03/010187,

[15] a protein consisting of an amino acid sequence wherein one or more amino acids are deleted, substituted or added in the amino acid sequence of the L-amino acid amide hydrolase described in WO 03/010187, and having an L-amino acid amide hydrolase activity, and

[16] a protein consisting of an amino acid sequence having 80% or more, preferably 90% or more, more preferably 95% or more, still more preferably 97% or more, particularly preferably 98% or more, most preferably 99% or more homology, with the amino acid sequence of the L-amino acid amide hydrolase described in WO 03/010187, and having an L-amino acid amide hydrolase activity.

In the above, the protein having an amino acid sequence wherein one or more amino acids are deleted, substituted or added, and having a dipeptide synthesizing activity can be acquired according to a method similar to the above-mentioned (1). The number, kind and the like of the amino acids to be deleted, substituted or added are the same as those in the above-mentioned (1).

The homology of amino acid sequences can be determined using a program such as the above-mentioned BLAST, FASTA and the like.

In addition, a microorganism having a recombinant DNA obtained by ligating a DNA encoding a protein having an activity to synthesize dipeptide by condensing and ligating one or more kinds of amino acids, a DNA encoding a protein having an activity to synthesize dipeptide from L-amino acid ester and L-amino acid, or a DNA encoding a protein having an activity to synthesize dipeptide from L-amino acid amide and L-amino acid and a vector DNA is also a microorganism having an ability to produce a protein having a dipeptide synthesizing activity.

Examples of the microorganism include microorganisms belonging to the genus *Escherichia, Bacillus, Corynebacterium* or *Saccharomyces*.

Examples of the DNA encoding a protein having an activity to synthesize dipeptide by condensing and ligating one or more kinds of amino acids include DNAs encoding NRPS, D-Ala-D-Ala ligase, L-amino acid ligase, and the like.

Examples of the DNA encoding NRPS include DNA encoding a protein selected from the group consisting of BacA, BacB, BacC, TycA, TycB, TycC and PcbAB.

Examples of the DNA encoding D-Ala-D-Ala ligase include a DNA encoding a protein selected from the group consisting of DdlA, DdlB and DdlC.

Examples of the DNA encoding L-amino acid ligase include DNA selected from the following [17]-[20]:

[17] a DNA encoding the L-amino acid ligase described in any of the above-mentioned [7] to [10],

[18] a DNA having a nucleotide sequence shown by any of SEQ ID NOs: 20 to 28,

[19] a DNA hybridizing with a DNA having a nucleotide sequence complementary to a nucleotide sequence shown by any of SEQ ID NOs: 20 to 28 under stringent conditions, and encoding a protein having an L-amino acid ligase activity, and

[20] a DNA having a nucleotide sequence having 80% or more, preferably 90% or more, more preferably 95% or more, still more preferably 97% or more, particularly preferably 98% or more, most preferably 99% or more homology, with the nucleotide sequence shown by SEQ ID NO: 29, and encoding a protein having an L-amino acid ligase activity.

Examples of the DNA encoding a protein having an activity to synthesize dipeptide from L-amino acid ester and L-amino acid include DNA selected from the following [21]-[23]:

[21] a DNA encoding the proline imino peptidase described in any of the above-mentioned [11] to [13],

[22] a DNA encoding proline imino peptidase having the nucleotide sequence described in any of WO 03/010307, FEMS Microbiol. Lett., 78, 191 (1999), JP-A-2-113887, Arch. Biochem. Biophys., 336, 35 (1996), J. Biochem., 119, 468 (1996), Microbiology, 140, 527 (1994), J. Bacteriol., 174, 7919 (1994), J. Biochem., 116, 818 (1994), JP-A-9-121860, Mol. Microbiol., 9, 1203 (1993), Appl. Environ. Microbiol., 64, 4736 (1998), J. Biochem., 122, 601 (1997), FEES Lett., 398, 101 (1996), and Nature, 406, 959 (2000), and

[23] a DNA hybridizing with a complementary strand DNA of the DNA encoding proline imino peptidase of any of the above-mentioned [21] under stringent conditions, and encoding a protein having a proline imino peptidase activity.

Examples of the DNA encoding a protein having an activity to synthesize dipeptide from L-amino acid amide and L-amino acid include DNA selected from the following [24]-[26]:

[24] a DNA encoding the L-amino acid amide hydrolase of any of the above-mentioned [14]-[16],

[25] a DNA encoding an L-amino acid amide hydrolase having the nucleotide sequence described in WO 03/010187, and

[26] a DNA hybridizing with a complementary strand of DNA encoding L-amino acid amide hydrolase having the nucleotide sequence described in WO 03/010187 under stringent conditions, and encoding a protein having an L-amino acid amide hydrolase activity.

The DNA which can hybridize under stringent conditions is the same as the definition of the above-mentioned 1(1). That the DNA hybridizing with the above-mentioned DNA under stringent conditions is a DNA encoding a protein having a dipeptide synthesis activity can be confirmed by a method including preparing a recombinant DNA expressing the DNA, using a microorganism obtained by introducing the recombinant DNA into a host cell as an enzyme source, 1) adding the enzyme source and one or more kinds of amino acids to an aqueous medium, and analyzing whether or not a dipeptide is formed and accumulated in the aqueous medium by HPLC and the like, 2) adding the enzyme source, L-amino acid ester and L-amino acid in an aqueous medium, and analyzing whether or not a dipeptide is formed and accumulated in the aqueous medium by HPLC and the like, or 3) adding the enzyme source, L-amino acid amide and L-amino acid in an aqueous medium, and analyzing whether or not a dipeptide is formed and accumulated in the aqueous medium by HPLC and the like.

The homology of the nucleotide sequence can be determined using a program such as the above-mentioned BLAST, FASTA and the like.

2. Preparation of Microorganism Used in the Present Invention (1) Preparation of Microorganism Wherein a Protein Having a Dipeptide Transporting Activity Shows Higher Activity than that of Parental Strain Of the microorganisms wherein a protein having a dipeptide transporting activity shows higher activity than that of the parental strain, a microorganism wherein a specific activity is higher than that of a protein having a dipeptide transporting activity of the parental strain can be acquired by subjecting a DNA encoding a protein having a dipeptide transporting activity to in vitro mutation treatment with a mutagen, or error-prone PCR and the like to introduce mutation into the DNA, substituting a DNA encoding a protein having a dipeptide transporting activity before introduction of mutation, which is present on the chromosomal DNA of the parental strain, with the mutant DNA by a known method [Proc. Natl. Acad. Sci. USA., 97, 6640 (2000)] to give a modified strain expressing the mutant DNA, and comparing the dipeptide transporting activity of the parental strain and the modified strain according to the above-mentioned methods.

In addition, of the microorganisms wherein a protein having a dipeptide transporting activity shows higher activity than that of the parental strain, a microorganism wherein the production amount of the protein is higher than that of the parental strain can be confirmed by a method including subjecting a DNA having a transcription regulatory region and a promoter region of the gene encoding a protein having a dipeptide transporting activity of the parental strain, for example, the nucleotide sequence of 200 bp, preferably 100 bp, upstream of the initiation codon of the protein to in vitro mutation treatment, or error-prone PCR and the like to introduce mutation into the DNA, substituting the transcription regulatory region and promoter region of the gene encoding a protein having a dipeptide transporting activity before introduction of mutation, which is present on the chromosomal DNA of the parental strain, with the mutant DNA by a known method [Proc. Natl. Acad. Sci. USA., 97, 6640 (2000)] to give a modified strain having a mutant transcription regulatory region or a promoter region, and comparing the amounts of the transcript of the genes encoding the protein having a dipeptide transporting activity of the parental strain and the modified strain by RT-PCR, Northern hybridization and the like, or comparing the production amounts of the protein having a dipeptide transporting activity of the parental strain and the modified strain by SDS-PAGE and the like.

In addition, a microorganism wherein the production level of the protein having a dipeptide transporting activity is promoted as compared to the parental strain can also be obtained by substituting the promoter region of a gene encoding the protein having a dipeptide transporting activity of the parental strain with a known strong promoter sequence.

Examples of such promoter include promoters derived from *Escherichia coli*, phage and the like, which are functional in *E. coli*, such as trp promoter ($P_{trp}$), lac promoter ($P_{lac}$), $P_L$ promoter, $P_R$ promoter, $P_{SE}$ promoter and the like, SPO1 promoter, SPO2 promoter, penP promoter and the like. In addition, artificially constructed promoters such as a promoter having two $P_{trp}$ connected in tandem, tac promoter, lacT7 promoter, let I promoter and the like can also be mentioned.

The method of preparing a DNA encoding a protein having a dipeptide transporting activity, and a method of preparing a microorganism obtained by transforming the parental strain with the DNA are explained in detail in the following.

(a) Preparation of a DNA Encoding Protein Having a Dipeptide Transporting Activity A DNA encoding a protein having a dipeptide transporting activity can be obtained, for example, by Southern hybridization of chromosomal DNA library of a microorganism such as *E. coli* and the like, using a probe DNA that can be designed based on the nucleotide sequence of DNA encoding a protein having the amino acid sequence shown by any of SEQ ID NOs: 6 to 10, or PCR [PCR Protocols, Academic Press (1990)] using a primer DNA that can be designed based on the nucleotide sequence and the chromosomal DNA of a microorganism, preferably *E. coli*, as a template.

In addition, it is possible to search various gene sequence databases for a sequence having 80% or more, preferably 90% or more, more preferably 95% or more, still more preferably 97% or more, particularly preferably 98% or more, most preferably 99% or more homology, with the nucleotide sequence of a DNA encoding a protein having the amino acid sequence shown by any of SEQ ID NOs: 6 to 10, and, based on the nucleotide sequence obtained by the search, obtain a DNA encoding a protein having a dipeptide transporting activity according to the above-mentioned methods from chromosomal DNA, cDNA library and the like of the microorganism having the nucleotide sequence.

The nucleotide sequence of the DNA can be determined by incorporating the obtained DNA directly or after cleaving with a suitable restriction enzyme and the like into a vector according to a conventional method, and introducing the obtained recombinant DNA into a host cell, and analyzing the sequence by a nucleotide sequence analysis method generally used, for example, dideoxy method [Proc. Natl. Acad. Sci., USA, 74, 5463 (1977)], or using a nucleotide sequence analysis apparatus such as 3700 DNA analyzer (manufactured by Applied Biosystems) and the like.

As the above-mentioned vector, pBluescriptII KS(+) (manufactured by Stratagene), pDIRECT [Nucleic Acids Res., 18, 6069 (1990)], pCR-Script Amp SK(+) (manufactured by Stratagene), pT7Blue (manufactured by Novagen), pCR II (manufactured by Invitrogen) and pCR-TRAP (manufactured by GenHunter Corporation) and the like can be mentioned.

As the host cell, microorganism belonging to the genus *Escherichia* and the like can be mentioned. Examples of the microorganism belonging to the genus *Escherichia* include E. coli XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415 and the like.

For introduction of recombinant DNA, any method can be used as long as the DNA is introduced into the above-mentioned host cell. For example, a method using calcium ion [Proc. Natl. Acad. Sci., USA, 69, 2110 (1972)], protoplast method (JP-A-63-248394), electroporation method [Nucleic Acids Res., 16, 6127 (1988)] and the like can be mentioned.

As a result of determination of the nucleotide sequence, when the obtained DNA is a partial DNA, full-length DNA can be obtained by subjecting chromosomal DNA library to a Southern hybridization method using the partial DNA as a probe and the like.

Furthermore, the object DNA can be prepared based on the determined DNA nucleotide sequence by chemical synthesis using a 8905 type DNA synthesizer manufactured by Perceptive Biosystems and the like.

Examples of the DNA obtained as mentioned above include a DNA encoding a protein having the amino acid sequence shown by any of SEQ ID NOs: 6 to 10 and a DNA having coding region in the nucleotide sequence shown by any of SEQ ID NOs: 1 to 5.

(b) Preparation of Microorganism Transformed with Plasmid Vector Expressing Protein Having Dipeptide Transporting Activity Based on the DNA encoding a protein having a dipeptide transporting activity, which is obtained by the method of the above-mentioned (a), a DNA fragment having a suitable length and containing a part encoding the protein having a dipeptide transport activity is prepared as necessary. In addition, a transformant showing an increased protein amount can be obtained by substituting the base in the nucleotide sequence of the part encoding the protein having a dipeptide transporting activity, such that a codon optimal for expression in the host cell can be obtained.

Recombinant DNA is prepared by inserting the DNA fragment into the downstream of a promoter of a suitable expression vector.

By introducing the recombinant DNA into a host cell suitable for the expression vector, a transformant wherein the activity of a protein having a dipeptide transport activity is improved as compared to that of the host cell, namely, the parental strain, can be obtained.

As the host cell, microorganisms, preferably procaryote, more preferably bacterium, more preferably microorganisms belonging to the genus *Escherichia*, most preferably *E. coli* can be used.

The expression vectors that can be employed are those capable of autonomous replication or integration into the chromosome in the above host cells and containing a promoter at a position appropriate for the transcription of the DNA encoding protein having a dipeptide transporting activity.

When a procaryote is used as the host cell, it is preferred that the recombinant DNA comprising the DNA which is capable of autonomous replication in the procaryote and which comprises a promoter, a ribosome binding sequence, the DNA encoding protein having a dipeptide transporting activity and a transcription termination sequence. The recombinant DNA may further comprise a gene regulating the promoter.

Examples of the expression vectors are pColdI (manufactured by Takara Bio Inc.), pCDF-1b, pRSF-1b (both manufactured by Novagen, Inc.), pMAL-c2x (manufactured by New England Biolabs), pGEX-4T-1 (manufactured by GE Healthcare Bioscience), pTrcHis (manufactured by Invitrogen), pSE280 (manufactured by Invitrogen), pGEMEX-1 (manufactured by Promega Corp.), pQE-30 (manufactured by Qiagen, Inc.), pET-3 (manufactured by Novagen, Inc.), pKYP10 (JP-A-58-110600), pKYP200[Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescriptII SK(+), pBluescript II KS(−) (manufactured by Stratagene), pTrS30 [prepared from 30 *Escherichia coli* JM109/pTrS30 (FERM BP-5407)], pTrS32 [prepared from *Escherichia coli* JM109/pTrS32 (FERM BP-5408)], pPAC31 (WO 98/12343), pUCi9 [Gene, 33, 103 (1985)], pSTV28 (manufactured by Takara Bio Inc.), pUC118 (manufactured by Takara Bio Inc.), pPA1 (JP-A-63-233798) and the like.

As the promoter, any promoter capable of functioning in host cells such as *E. coli* can be used. For example, promoters derived from *E. coli*, phage and the like, such as trp promoter ($P_{trp}$), lac promoter ($P_{lac}$), $P_L$ promoter, $P_R$ promoter and $P_{SE}$ promoter, SPO1 promoter, SPO2 promoter and penP promoter can be used. Artificially designed and modified promoters such as a promoter in which two $P_{trp}$s are combined in tandem, tac promoter, lacT7 promoter and let I promoter, etc. can also be used.

Also promoters such as xylA promoter for the expression in microorganisms belonging to the genus *Bacillus* [Appl. Microbiol. Biotechnol., 35, 594-599 (1991)] and P54-6 promoter for the expression in microorganisms belonging to the genus *Corynebacterium* [Appl. Microbiol. Biotechnol., 53, 674-679 (2000)] can be used.

It is preferred to use a plasmid in which the distance between the Shine-Dalgarno sequence (ribosome binding sequence) and the initiation codon is adjusted to an appropriate length (e.g., 6 to 18 bases).

In a recombinant DNA wherein a DNA encoding a protein having a dipeptide transporting activity is bonded to an expression vector, a transcription terminator sequence is not always necessary. However, it is preferable to arrange the transcription terminator sequence immediately beneath the structural gene.

Examples of such recombinant DNA include pSbcr, pSnorE, pSydeE, pSemrD, and pSyeeO below.

As a host of the recombinant DNA, procaryote, more preferably bacterium can be mentioned.

Examples of the procaryote include microorganism belonging to the genus *Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus, Zymomonas* and the like. For example, *Escherichia coli, Bacillus subtilis, Bacillus megaterium, Bacillus amyloliquefaciens, Bacillus coagulans, Bacillus licheniformis, Bacillus pumilus, Brevibacterium ammoniagenes, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia ficaria, Serratia fonticola, Serratia liquefaciens, Serratia marcescens, Pseudomonas aeruginosa, Pseudomonas putida, Agrobacterium radiobacter, Agrobacterium rhizogenes, Agrobacterium rubi, Anabaena cylindrica, Anabaena doliolum, Anabaena flos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium* sp. ATCC29409, *Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Zymomonas mobilis* and the like can be mentioned. Examples of preferable procaryote include bacterium belonging to the genus *Escherichia, Serratia, Bacillus, Brevibacterium, Corynebacterium, Pseudomonas, Streptomyces* and the like. For example, the above species belonging to the genus

*Escherichia, Serratia, Bacillus, Brevibacterium, Corynebacterium, Pseudomonas, Streptomyces* and the like can be mentioned. Examples of more preferable bacterium include *Escherichia coli, Corynebacterium glutamicum, Corynebacterium ammoniagenes, Corynebacterium lactofermentum, Corynebacterium flavum, Corynebacterium efficiens, Bacillus sabtilis, Bacillus megaterium, Serratia marcescens, Pseudomonas putida, Pseudomonas aeruginosa, Streptomyces coelicolor* and *Streptomyces lividans*. Particularly preferably, *Escherichia coli* can be mentioned.

(c) Preparation of a Microorganism Wherein a DNA Encoding a Protein Having a Dipeptide Transporting Activity is Incorporated into Chromosomal DNA By incorporating a DNA encoding a protein having a dipeptide transporting activity obtained by the method of the above-mentioned (a) into any position of chromosomal DNA, a microorganism wherein the activity of the protein having a dipeptide transporting activity is higher than that of the parental strain can also be obtained.

As the method for incorporating a DNA encoding a protein having a dipeptide transporting activity into any position of chromosomal DNA of a microorganism, a method utilizing homologous recombination can be mentioned. When *E. coli* is used as a host, namely, a parental strain, the method described in Proc. Natl. Acad. Sci. USA., 97, 6640 (2000) can be mentioned.

(2) Preparation of a Microorganism Wherein the Activity of Protein Having a Dipeptide Synthesizing Activity is Higher than that of Parental Strain Of the microorganisms wherein the activity of a protein having a dipeptide synthesizing activity is higher than that of the parental strain, a microorganism showing specific activity higher than the protein of the parental strain, and a microorganism wherein the production amount of the protein is improved as compared to the parental strain can be obtained as in the above-mentioned (1) by substituting a mutant enzyme gene obtained by subjecting a DNA encoding a protein having a dipeptide synthesizing activity to in vitro mutation treatment, error-prone PCR and the like with the gene of the parental strain.

By respectively culturing the obtained microorganism having a mutant enzyme gene and the parental strain in a liquid culture medium, and measuring and comparing the amount of dipeptide contained in the culture by a known method, the higher activity of the protein having a dipeptide synthesis activity than that of the parental strain can be confirmed.

A method of preparing DNA encoding the protein having a dipeptide synthesizing activity and a method of preparing the microorganism obtained by transforming the parental strain with the DNA are explained in the following.

(a) Preparation of a DNA Encoding a Protein Having Dipeptide Synthesizing Activity A DNA encoding a protein having a dipeptide synthesis activity can be obtained according to the nucleotide sequence of a DNA encoding a protein having a dipeptide synthesizing activity of the above-mentioned 1(2) in the same manner as in the above-mentioned 2(1)(a).

Examples of the DNA obtainable by the above-mentioned method include a DNA having a coding region in the nucleotide sequence shown by any of SEQ ID NOs: 20 to 28, which encodes L-amino acid ligase having the amino acid sequences shown by SEQ ID NOs: 11-18.

(b) Preparation of a Microorganism Transformed with a Plasmid Vector Expressing a Protein Having a Dipeptide Synthesizing Activity A plasmid vector expressing a protein having a dipeptide synthesizing activity can be obtained using the DNA encoding a protein having a dipeptide synthesizing activity, which is obtained in the above-mentioned 2(2)(a), and in the same manner as in the above-mentioned 2(1)(b).

Examples of the plasmid vector expressing a protein having a dipeptide synthesizing activity, which can be obtained by the above-mentioned method, include pPE86usp to be mentioned below.

(c) Preparation of Microorganism Wherein DNA Encoding Protein Having Dipeptide Synthesizing Activity is Incorporated into Chromosomal DNA A microorganism wherein the activity of a protein having a dipeptide synthesizing activity is higher than that of the parental strain can also be obtained by incorporating the DNA encoding a protein having a dipeptide synthesizing activity, which is obtained by the method of the above-mentioned 2(2)(a), into any position of a chromosomal DNA.

The DNA can be incorporated into any position of a chromosomal DNA of microorganism in the same manner as in the above-mentioned 2(1)(c).

(3) Preparation of Microorganism Having Ability to Produce at Least One Kind of Amino Acid from Amino Acids Constituting Dipeptide The microorganism having an ability to produce at least one kind of amino acid from the amino acids constituting the dipeptide, which is used in the process for producing a dipeptide of the present invention, may be any as long as it has such ability. When a strain isolated from the natural world has such ability in itself, the strain per se may be used. Alternatively, a microorganism conferred with an ability to produce at least one kind of amino acid from the amino acids constituting the dipeptide by a known method and the like may be used.

Examples of the known method include (a) a method of moderating or releasing at least one of the mechanisms regulating biosynthesis of an amino acid, (b) a method of potentiating expression of at least one enzyme involved in biosynthesis of an amino acid, (c) a method of increasing the copy number of at least one of enzyme genes involved in biosynthesis of an amino acid, (d) a method of weakening or blocking at least one metabolism pathway branching biosynthesis pathway of an amino acid to metabolite other than the amino acid, and (e) a method of selecting cell line having high resistance to an amino acid analogue as compared to wild-type strain, and the like. The above-mentioned known methods can be used alone or in combination.

The above-mentioned (a) is described in, for example, Agric. Biol. Chem., 43, 105-111 (1979), J. Bacteriol., 110, 761-763 (1972) and Appl. Microbiol. Biotechnol., 39, 318-323 (1993) and the like; the above-mentioned (b) is described in, for example, Agric. Biol. Chem., 43, 105-111 (1979) and J. Bacteriol., 110, 761-763 (1972) and the like; the above-mentioned (c) is described in, for example, Appl. Microbiol. Biotechnol., 39, 318-323 (1993) and Agric. Biol. Chem., 39, 371-377 (1987) and the like; the above-mentioned (d) is described in, for example, Appl. Environ. Micribiol., 38, 181-190 (1979) and Agric. Biol. Chem., 42, 1773-1778 (1978) and the like; and the above-mentioned (e) is described in, for example, Agric. Biol. Chem., 36, 1675-1684 (1972), Agric. Biol. Chem., 41, 109-116 (1977), Agric. Biol. Chem., 37, 2013-2023 (1973) and Agric. Biol. Chem., 51, 2089-2094 (1987) and the like. A microorganism having an ability to produce various amino acids can be prepared by reference to the above-mentioned publications and the like.

Furthermore, many examples of a method of preparing a microorganism having an ability to produce an amino acid by any of the above-mentioned (a)-(e) or a combination thereof are described in Biotechnology 2nd ed., Vol. 6, Products of Primary Metabolism (VCH Verlagsgesellschaft mbH, Weinheim, 1996) section 14a, 14b, and Advances in Biochemical Engineering/Biotechnology, 79, 1-35 (2003), and Amino Acid Fermentation, Japan Scientific Societies Press, Hiroshi Aida et al. (1986). In addition to the above, many reports on a method of preparing a microorganism having an ability to produce a specific amino acid are presented in JP-A-2003-164297, Agric. Biol. Chem., 39, 153-160 (1975), Agric. Biol. Chem., 39, 1149-1153 (1975), JP-A-58-13599, J. Gen. Appl. Microbiol., 4, 272-283 (1958), JP-A-63-94985, Agric. Biol. Chem., 37, 2013-2023 (1973), WO 97/15673, JP-A-56-18596, JP-A-56-144092, National Publication of International Patent Application No. 2003-511086 and the like. A microorganism having an ability to produce one or more kinds of amino acids can be prepared by reference to the above-mentioned publications and the like.

Examples of the microorganism having an ability to produce an amino acid, which can be prepared by the above-mentioned method, include a microorganism as L-glutamine producing bacterium, which is defective in glnE gene and/or glnB gene, a microorganism as L-alanine producing bacterium, which shows enhanced expression of alanine dehydrogenase gene (ald gene), a microorganism as L-proline producing microorganism, which expresses phenylalanine-insensitive pheA gene and/or tyrosine-insensitive aroF gene and the like.

The above-mentioned microorganism that forms and accumulates an amino acid may be any as long as the methods of the above-mentioned (a)-(e) can be applied to or it has the above-mentioned genetic properties. Preferred is procaryote and more preferred is bacterium. The procaryote and bacterium are the same as in the above-mentioned 2(1).

Examples of the microorganism producing an amino acid include *Escherichia coli* JGLE1, *Escherichia coli* JGLBE1 and the like as a L-glutamine producing strain, *Escherichia coli* JM101 strain carrying ald gene expression plasmid and the like as a L-alanine producing strain, *Escherichia coli* JM101 strain carrying pPHEA2 and/or aroF gene expression plasmid and the like as a L-phenylalanine producing strain, *Escherichia coli* JGLE1 and *Escherichia coli* JGLBE1 carrying aid gene expression plasmid and the like as a L-glutamine and L-alanine producing strain, *Escherichia coli* JM101 carrying ald gene expression plasmid and pPHEA2 and/or aroF gene expression plasmid and the like as a L-alanine and L-phenylalanine producing strain, ATCC21277 strain carrying pPHEA2 and/or aroF gene expression plasmid and the like as a L-threonine and L-phenylalanine producing strain, they are described in WO 2006/001379.

Specifically, examples of the microorganism having an ability to produce an amino acid include FERM BP-5807, ATCC13032 and the like as a L-glutamic acid producing strain, FERM P-4806, ATCC14751 and the like as a L-glutamine producing strain, ATCC21148, ATCC21277, ATCC21650 and the like as a L-threonine producing strain, FERM P-5084, ATCC13286 and the like as a L-lysine producing strain, FERM P-5479, VKPM B-2175, ATCC21608 and the like as a L-methionine producing strain, FERM BP-3757, ATCC14310 and the like as a L-isoleucine producing strain, ATCC13005, ATCC19561 and the like as a L-valine producing strain, FERM BP-4704, ATCC21302 and the like as a L-leucine producing strain, FERM BP-4121, ATCC15108 and the like as a L-alanine producing strain, ATCC21523, FERM BP-6576 and the like as a L-serine producing strain, FERM BP-2807, ATCC19224 and the like as a L-proline producing strain, FERM P-5616, ATCC21831 and the like as a L-arginine producing strain, ATCC13232 and the like as a L-ornithine producing strain, FERM BP-6674, ATCC21607 and the like as a L-histidine producing strain, DSM10118, DSM10121, DSM10123, FERM BP-1777 and the like as a L-tryptophan producing strain, ATCC13281, ATCC21669 and the like as a L-phenylalanine producing strain, ATCC21652 and the like as a L-tyrosine producing strain, W3110/pHC34 (described in National Publication of International Patent Application No. 2003-511086) and the like as a L-cysteine producing strain, *Escherichia coli* SOLR/pRH71 (described in WO 96/27669) and the like as a L-4-hydroxyproline producing strain, FERM BP-5026, FERM BP-5409 and the like as a L-3-hydroxyproline producing strain, FERM P-5643, FERM P-1645 and the like as an L-citrulline producing strain.

The strain shown by the above-mentioned FERM number is available from the International Patent Organism Depositary, National Institute of Advanced Industrial Science and Technology (Japan), the strain shown by ATCC number can be obtained from American Type Culture Collection (USA), the strain shown by VKPM number can be obtained from Russian National Collection of Industrial Microorganisms (Russia), and the strain shown by DSM number can be obtained from Deutsche Sammlung von Mikroorganismen and Zellkulturen (Germany).

(4) Preparation of Microorganism Wherein Activity of Protein Having Peptidase or Peptide Uptaking Activity is Lower than that of Parental Strain or Lost The microorganism of the present invention and a microorganism to be used in the production method of dipeptide of the present invention have an ability to produce a protein having a dipeptide synthesizing activity, wherein the activity of the protein having a dipeptide transporting activity is higher than that of the parental strain, and the activity of the protein having a peptidase or peptide uptaking activity may be lower than that of the parental strain or lost.

The microorganism wherein the activity of a protein having a peptidase or peptide uptaking activity may be lower than that of the parental strain or lost can be prepared according to the method described in WO 2005/045006.

3. Process for Producing Dipeptide of the Present Invention (1) Process for Producing Dipeptide Using Microorganism Culture or Treated Culture Thereof as an Enzyme Source A culture of the microorganism of the present invention can be obtained by culturing the microorganism in a natural medium or synthetic medium containing carbon sources, nitrogen sources, inorganic salts and the like utilizable by the microorganism, and permitting efficient culture of a transformant.

As the carbon sources, any carbon sources that can be assimilated by the microorganism can be used. Examples of carbon sources include hydrocarbonate such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of inorganic or organic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an inorganic or organic acid, an alkali solution, urea, calcium carbonate, ammonia, etc.

If necessary, antibiotics such as ampicillin and tetracycline may be added to the culture medium during the culturing.

When a microorganism transformed with an expression vector comprising an inducible promoter is cultured, an inducer may be added to the culture medium, if necessary. For example, in the case of a microorganism transformed with an expression vector comprising lac promoter, isopropyl-β-D-thiogalactopyranoside or the like may be added to the culture medium; and in the case of a microorganism transformed with an expression vector comprising trp promoter, indoleacrylic acid or the like may be added.

Examples of treated culture include concentrated culture obtained from the above-mentioned method, dried culture, microbial cells centrifuged and obtained from the culture, dried microbial cells, freeze-dried microbial cells, surfactant treated microbial cells, sonicated microbial cells, mechanically grinded microbial cells, solvent treated microbial cells, enzyme treated microbial cells and treated culture containing viable microbial cells such as immobilized microbial cells.

Using a culture or a treated culture of the microorganism of the present invention, which can be obtained by the above-mentioned method, as an enzyme source, a dipeptide can be produced by forming and accumulating the dipeptide in an aqueous medium containing the enzyme source and one or more kinds of substrates selected from an amino acid, amino acid ester and amino acid amide, and recovering the dipeptide from the medium.

The above-mentioned process is explained in detail in the following by dividing into (i) to (iii):

(i) a process using a culture or a treated culture of the microorganism as an enzyme source, wherein dipeptide is formed and accumulated in an aqueous medium containing the enzyme source and one or more kinds, preferably one or two kinds, of amino acids, and recovered from the medium, (ii) a process using a culture or a treated culture of the microorganism as an enzyme source, wherein a dipeptide is formed and accumulated in an aqueous medium containing the enzyme source, one or more kinds, preferably one kind, of amino acid ester and one or more kinds, preferably one kind, of amino acid, and recovered from the medium, and (iii) a process using a culture or a treated culture of the microorganism as an enzyme source, wherein a dipeptide is formed and accumulated in an aqueous medium containing the enzyme source, one or more kinds, preferably one kind, of amino acid amide and one or more kinds, preferably one kind, of amino acid, and recovered from the medium.

In the production process of the above-mentioned (i), one or more kinds, preferably one or two kinds of amino acids used as substrates may be any amino acids, preferably amino acids selected from the group consisting of L-amino acids, glycine (Gly) and β-alanine (β-Ala), which can be used in any combination. Examples of the L-amino acid include L-alanine (L-Ala), L-glutamine (L-Gln), L-glutamic acid (L-Glu), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-tyrosine (L-Tyr), L-lysine (L-Lys), L-arginine (L-Arg), L-histidine (L-His), L-aspartic acid (L-Asp), L-α-aminobutyric acid (L-α-AB), L-azaserine, L-theanine, L-4-hydroxyproline (L-4-HYP), L-3-hydroxyproline (L-3-HYP), L-ornithine (L-Orn), L-citrulline (L-Cit) and L-6-diazo-5-oxo norleucine and the like.

The amino acids which are more preferably used in the production process of the above-mentioned (i) are a combination of one kind of amino acid selected from the group consisting of L-Ala, Gly, L-Met, L-Ser, L-Thr, L-Cys, L-α-AB and β-Ala, and one kind of amino acid selected from the group consisting of L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, β-Ala, L-azaserine, L-theanine, L-4-HYP, L-3-HYP, L-Orn, L-Cit and L-6-diazo-5-oxo-norleucine; a combination of L-Gln and L-Phe. Further preferred amino acids are: a combination of L-Ala and one kind of amino acid selected from the group consisting of L-Ala, L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-Azaserine, L-Cit and L-theanine; a combination of Gly and one kind of amino acid selected from the group consisting of L-Gln, Gly, L-Phe, L-Trp, L-Met, L-Ser, L-Thr, L-Cys, L-Tyr, L-Lys, L-Arg, L-α-AB and L-Cit; a combination of L-Met and one kind of amino acid selected from the group consisting of L-Phe, L-Met, L-Ser, L-Thr, L-Cys, L-Tyr, L-Lys and L-His; a combination of L-Ser and one kind of amino acid selected from the group consisting of L-Gln, L-Phe, L-Ser, L-Thr, L-Tyr, L-His and L-α-AB; a combination of L-Thr and one kind of amino acid selected from the group consisting of L-Gln, L-Phe, L-Leu, L-Thr and L-α-AB; a combination of L-Gln and L-Phe; a combination of β-Ala and one kind of amino acid selected from the group consisting of L-Phe, L-Met, L-His and L-Cit; a combination of L-α-AB and L-Gln, L-Arg or L-α-AB.

In the production process of the above-mentioned (i), the amino acid to be used as a substrate is added to an aqueous medium to a concentration of 0.1-500 g/L, preferably 0.2-200 g/L, from the start of or during the reaction.

Examples of the dipeptide produced by the production process of the above-mentioned (i) include a dipeptide represented by the following formula (I)

$$R^1\text{-}R^2 \qquad (I)$$

wherein $R^1$ and $R^2$ are the same or different and each is an is amino acid. Preferable examples include a dipeptide represented by the above-mentioned formula (I) wherein $R^1$ and $R^2$ are the same or different and each is an amino acid selected from L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, β-Ala, L-azaserine, L-theanine, L-4-HYP, L-3-HYP, L-Orn and L-6-diazo-5-oxo-norleucine. More preferred is a dipeptide wherein when $R^1$ is L-Ala, Gly, L-Met, L-Ser, L-Thr, L-Cys, L-α-AB or β-Ala, then $R^2$ is L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, β-Ala, L-azaserine, L-theanine, L-4-HYP, L-3-HYP, L-Orn or L-6-diazo-5-oxo-norleucine, and still more preferred is a dipeptide wherein when $R^1$ is L-Ala, then $R^2$ is L-Ala, L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine or L-theanine, when $R^1$ is Gly, then $R^2$ is L-Gln, Gly, L-Trp, L-Met, L-Ser, L-Thr, L-Cys, L-Tyr, L-Lys, L-Arg or L-α-AB, when $R^1$ is L-Met, then $R^2$ is L-Phe, L-Met, L-Cys, L-Tyr, L-Lys or L-His, when $R^1$ is L-Ser, then $R^2$ is L-Gln, Gly, L-Phe, L-Met, L-Ser, L-Thr, L-Tyr, L-His or L-α-AB, when $R^1$ is L-Thr, then $R^2$ is L-Gln, L-Gly, L-Phe, L-Met, L-Ser, L-Thr or L-α-AB, when $R^1$ is L-Gln, then $R^2$ is L-Phe or L-α-AB, when $R^1$ is L-Phe, then $R^2$ is L-Gln, when re is L-Trp, then $R^2$ is Gly, when $R^1$ is L-Cys, then $R^2$ is L-Ala, L-Gln, Gly or L-Met, when $R^1$ is L-Lys, then $R^2$ is L-Ala, Gly or L-Met, when $R^1$ is L-Arg, then $R^2$ is L-α-AB, when $R^1$ is L-His, then $R^2$ is L-Met, or when $R^1$ is L-α-AB, then $R^2$ is L-Ala, L-Gln, Gly, L-Ser, L-Thr, L-Arg or L-α-AB.

In the above-mentioned production process, moreover, a compound which can be metabolized by the microorganism of the present invention to produce ATP, for example, saccharides such as glucose, alcohols such as ethanol, organic acids such as acetic acid and the like can be added as necessary as a supply source of ATP to an aqueous medium.

In the production process of the above-mentioned (ii), one or more kinds of amino acid esters and one or more kinds of amino acids to be used as substrates may be any combination of any amino acid ester and any amino acid as long as the microorganism to be used as an enzyme source in the production process of the present invention can form dipeptide by using them as the substrates. Preferred is a combination of one kind of amino acid ester and one kind of amino acid, wherein the amino acid is preferably L-amino acid or glycine. Examples of a more preferable combination of one kind of amino acid ester and one kind of amino acid include a combination of amino acid ester, which is one kind selected from the group consisting of L-alanine ester, glycine ester, L-valine ester, L-isoleucine ester, L-methionine ester, L-phenylalanine ester, L-serine ester, L-threonine ester, L-glutamine ester, L-tyrosine ester, L-arginine ester, L-aspartic acid-α-ester, L-aspartic acid-β-ester, L-leucine ester, L-asparagine ester, L-lysine ester, L-aspartic acid-α,β-dimethylester and L-glutamine-γ-ester, and amino acid, which is one kind selected from the group consisting of L-Gln, L-Asn, Gly, L-Ala, L-Leu, L-Met, L-Pro, L-Phe, L-Trp, L-Ser, L-Thr, L-Tyr, L-Lys, L-Arg, L-His and L-Glu.

In the production process of the above-mentioned (ii), the amino acid ester and amino acid to be used as substrates are added to an aqueous medium to a concentration of 0.1-500 g/L, preferably 0.2-200 g/L, from the start of or during the reaction.

In the production process of the above-mentioned (iii), one or more kinds of amino acid amides and one or more kinds of amino acids to be used as substrates may be any combination of any amino acid amide and any amino acid as long as the microorganism to be used as an enzyme source in the production method of the present invention can form dipeptide by using them as the substrates. Preferred is a combination of one kind of amino acid amide and one kind of amino acid. As the amino acid, L-amino acid and glycine are preferable. Examples of the combination of one kind of amino acid amide and one kind of amino acid include a combination of one kind of amino acid amide selected from the group consisting of L-alanine amide, glycine amide and L-aspartic acid amide, and one kind of amino acid selected from the group consisting of L-Gln, L-Asn, Gly, L-Ala, L-Val, L-Leu, L-Ile, L-Met, L-Pro, L-Phe, L-Trp, L-Ser, L-Thr, L-Tyr, L-Lys, L-Arg, L-His and L-Glu.

In the production process of the above-mentioned (iii), the amino acid amide and amino acid to be used as substrates are added to an aqueous medium to a concentration of 0.1-500 g/L, preferably 0.2-200 g/L, from the start of or during the reaction.

The aqueous medium to be used in the production process of the present invention may have any components and any composition as long as it does not inhibit the reaction for production of a dipeptide. For example, water, buffers such as phosphate, carbonate, acetate, borate, citrate, tris etc. and the like can be mentioned. In addition, it may contain alcohols such as methanol, ethanol and the like, ester such as ethyl acetate and the like, ketone such as acetone and the like, and amides such as acetamide and the like.

The reaction for production of a dipeptide is performed in an aqueous medium under the conditions of pH 5-11, preferably pH 6-10, at 20-60° C., preferably 25-45° C., for 2-150 hr, preferably 6-120 hr.

Where necessary, a surfactant or an organic solvent may be further added to the aqueous medium.

The surfactant may be any as long as it promotes formation of a dipeptide such as nonionic surfactants such as polyoxyethylene octadecylamine (e.g., NYMEEN S-215, manufactured by NOF Corporation), cationic surfactants such as cetyl trimethylammonium bromide and alkyldimethyl benzylammonium chloride (e.g., cation F2-40E manufactured by NOF Corporation), anionic surfactants such as lauroyl sarcosinate, tertiary amine such as alkyldimethylamine (e.g., tertiary amine FB, manufactured by NOF Corporation) and the like. One kind or several kinds of these can be used in a mixture. The concentration of the surfactant is generally 0.1-50 g/l. Examples of the organic solvent include xylene, toluene, aliphatic alcohol, acetone, ethyl acetate and the like, and it is generally used at a concentration of 0.1-50 ml/l.

While the amount of the culture or a treated product of the culture to be used as an enzyme source varies depending on the specific activity and the like of the enzyme source, it is, for example, 5-1000 mg, preferably 10-400 mg, per 1 mg of amino acid, amino acid methyl ester or amino acid amide as the substrate.

The dipeptide formed and accumulated in the aqueous medium can be harvested by a general method using activated carbon, ion exchange resin and the like, or extraction with organic solvent, crystallization, thin layer chromatography, high performance liquid chromatography and the like.

Moreover, the production processes of the above-mentioned (ii) and (iii) can be performed according to the description of WO 03/010189 or WO 03/010187.

(2) Production by Fermentation Method

A dipeptide can be produced by culturing the microorganism of the present invention having an ability to produce at least one kind of amino acid from among the amino acids constituting dipeptide in a culture medium to allow formation and accumulation of the dipeptide in the culture medium, and recovering the dipeptide from the culture.

The method for culturing the microorganism in a culture medium is similar to the culturing method in the above-mentioned (1). When desired, the culture medium may contain at least one kind of amino acid constituting the desired dipeptide.

Example of the dipeptide produced by the above-mentioned process includes a dipeptide wherein one or two kinds of amino acids are α-bonded, with preference given to dipeptide wherein the amino acid is L-amino acid or glycine. More preferred is a dipeptide represented by the following formula (II)

$$R^1\text{-}R^2 \tag{II}$$

wherein $R^1$ and $R^2$ are the same or different and each is an amino acid selected from L-Ala, L-Gln, L-Glu, Gly, L-Val, L-Leu, L-Ile, LL-Pro, L-Phe, L-Trp, L-Met, L-Ser, L-Thr, L-Cys, L-Asn, L-Tyr, L-Lys, L-Arg, L-His, L-Asp, L-α-AB, L-4-HYP, L-3-HYP, L-ornithine (L-Orn) and L-citrulline (L-Cit). More preferred is a dipeptide wherein when $R^1$ is L-Ala, Gly, L-Met, L-Ser, L-Cys, L-α-AB or L-Thr, then $R^2$ is L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, L-4-HYP, L-3-HYP, L-Orn or L-Cit. Particularly preferred is a dipeptide wherein when $R^1$ is L-Ala, then $R^2$ is L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB or L-Cit, when $R^1$ is Gly, then $R^2$ is L-Gln, Gly, L-Phe, L-Trp, L-Met, L-Ser, L-Thr, L-Cys, L-Tyr, L-Lys, L-Arg, L-α-AB or L-Cit, when $R^1$ is L-Met, then $R^2$ is L-Phe, L-Met, L-Cys, L-Tyr, L-Lys or L-His, when $R^1$ is L-Ser, then $R^2$ is L-Gln, Gly, L-Phe, L-Met, L-Ser, L-Thr, L-Tyr, L-His or L-α-AB, when $R^1$ is L-Thr, then $R^2$ is L-Gln, L-Leu, L-Phe, L-Met, L-Ser, L-Thr or L-α-AB, when $R^1$ is L-Gln, then $R^2$ is L-Phe or L-α-AB, when $R^1$ is L-Phe, then $R^2$ is L-Gln, when $R^1$ is L-Trp, then $R^2$ is Gly, when $R^1$ is L-Cys, then $R^2$ is L-Ala, L-Gln, Gly or L-Met, when $R^1$ is L-Lys, then $R^2$ is L-Ala, Gly or L-Met, when $R^1$ is L-Arg, then $R^2$ is L-α-AB, when $R^1$ is L-His, then $R^2$ is L-Met, or when $R^1$ is L-α-AB, then $R^2$ is L-Ala, L-Gln, Gly, L-Ser, L-Thr, L-Arg or L-α-AB, and most preferred are L-alanyl-L-alanine (L-Ala-L-Ala), L-alanyl-L-glutamine (L-Ala-L-Gln), L-alanyl-L-phenylalanine (L-Ala-L-Phe) and L-threonyl-L-phenylalanine (L-Thr-L-Phe).

Recovery of the dipeptide formed and accumulated in the aqueous medium or culture can be carried out by ordinary methods using activated carbon, ion exchange resins, etc. or by means such as extraction with an organic solvent, crystallization, thin layer chromatography, high performance liquid chromatography and the like.

The present invention is explained in detail in the following by referring to Examples, which are not to be construed as limitative.

EXAMPLE 1

Construction of bcr Gene Expression Plasmid

A bcr gene expression plasmid was constructed by the following method.

*Escherichia coli* JM101 strain was inoculated into LB medium [10 g/l Bacto Tripton (manufactured by Difco), 5 g/l yeast extract (manufactured by Difco), 5 g/l sodium chloride] and cultured by standing at 30° C. overnight. After culture, the chromosomal DNA of the microorganism was isolated and purified by a method using saturated phenol described in Current Protocols in Molecular Biology.

Based on the nucleotide sequence shown by SEQ ID NO: 1, DNAs consisting of the nucleotide sequence shown by SEQ ID NO: 30 or 31 were synthesized as primer DNAs for bcr gene amplification, and PCR was performed using the synthetic DNAs as a primer set.

PCR was performed by preparing 50 µL of a reaction mixture comprising 0.1 µg of chromosomal DNA as a template, 0.5 µmol/L of each of the primers, 2.5 units of Pyrobest DNA polymerase(manufactured by Takara Bio Inc.), 5 µL of buffer for Pyrobest DNA polymerase (10×) (manufactured by Takara Bio Inc.) and 200 µmol/L each of dNTPs (dATP, dGTP, dCTP and dTTP) and repeating 30 times a cycle consisting of reaction at 96° C. for 15 sec, reaction at 55° C. for 30 sec and reaction at 72° C. for 1 min.

After confirmation of the amplification of about 1.2 kb DNA fragment, the DNA fragment was purified by a conventional method.

The expression vector pTrS30 [prepared from *Escherichia coli* JM109/pTrS30 (FERM BP-5407)] containing the DNA fragment and trp promoter was digested with HindIII, SacI, respectively, the DNA fragments were separated by agarose gel electrophoresis and DNA fragments digested with restriction enzyme were recovered using a GENECLEAN II kit (manufactured by BIO 101).

The 1.2 kb fragment containing the bcr gene obtained above, and pTrs30 fragment digested with restriction enzyme were ligated to each other using a Ligation Kit (manufactured by Takara Bio Inc.).

*Escherichia coli* DH5α strain (manufactured by Takara Bio Inc.) was transformed using the obtained ligated DNA, and a transformant was selected with ampicillin resistance as an index.

A plasmid was extracted from the colony of the selected transformant by a known method, and the structure thereof was analyzed using a restriction enzyme, whereby it was confirmed that pTbcr expression vector wherein bcr gene was ligated to the downstream of trp promoter was acquired.

Then, pTbcr and pSTV28 were digested with EcoRI and SacI, respectively, and 1.6 kb fragment wherein bcr gene was ligated to the downstream of trp promoter and pSTV28 fragment digested with restriction enzyme were recovered in the same manner as in the above.

They were ligated in the same manner as in the above, *Escherichia coli* DH5α strain was transformed with the obtained ligated DNA, and a transformant was selected with chloramphenicol resistance as an index.

A plasmid was extracted from the colony of the selected transformant by a known method, and the structure thereof was analyzed using a restriction enzyme, whereby it was confirmed that an expression vector wherein bcr gene was ligated to the downstream of trp promoter was obtained. The expression vector was designated as pSbcr.

EXAMPLE 2

Construction of norE Gene Expression Plasmid

Based on the nucleotide sequence shown by SEQ ID NO: 2, the primer DNAs consisting of a nucleotide sequence shown by SEQ ID NO: 32 or 33 were synthesized in the same manner as Example 1 as primer DNAs for norE gene amplification. PCR was performed using these synthetic DNAs as a set of primers.

PCR was performed under similar conditions as in Example 1 except that the above-mentioned primer set was used as a primer DNA.

The amplified DNA fragment obtained by PCR and pTrS30 were digested with HindIII and BamHI, respectively, the both DNAs were ligated to each other in the same manner as in Example 1, and *Escherichia coli* DH5α strain was transformed with the ligated DNA.

An expression vector pTnorE wherein norE gene was ligated to the downstream of trp promoter was constructed by extraction from the obtained transformant. In the same manner as in Example 1, pTnorE and pSTV28 were digested with EcoRI and BamHI, respectively. Both DNAs were ligated to each other and the expression vector wherein norE gene was ligated to the downstream of trp promoter was constructed in the same manner as in Experimental Example 1 and designated as pSnor.

EXAMPLE 3

Construction of ydeE Gene Expression Plasmid

Based on the nucleotide sequence shown by SEQ ID NO: 3, the primer DNAs consisting of a nucleotide sequence shown by SEQ ID NO: 34 or 35 were synthesized in the same manner as Example 1 as primer DNAs for ydeE gene amplification. PCR was performed using these synthetic DNAs as a set of primers.

PCR was performed under similar conditions as in Example 1 except that the above-mentioned primer set was used as a primer DNA.

The amplified DNA fragment obtained by PCR and pSTV28 were digested with EcoRI and BamHI, respectively. Both DNAs were ligated to each other in the same manner as in Example 1 and *Escherichia coli* DH5α strain was transformed with the ligated DNA. The expression vector wherein ydeE gene was ligated to the downstream of lac promoter was constructed by the above-mentioned method and designated as pSydeE.

EXAMPLE 4

Construction of emrD Gene Expression Plasmid

Based on the nucleotide sequence shown by SEQ ID NO: 4, the primer DNAs consisting of a nucleotide sequence shown by SEQ ID NO: 36 or 37 were synthesized in the same manner as Example 1 as primer DNAs for emrD gene amplification. PCR was performed using these synthetic DNAs as a set of primers.

PCR was performed under similar conditions as in Example 1 except that the above-mentioned primer set was used as a primer DNA.

The amplified DNA fragment obtained by PCR and pSTV28 were digested with EcoRI and PstI, respectively. Both DNAs were ligated to each other in the same manner as in Example 1 and *Escherichia coli* DH5α strain was transformed with the ligated DNA. The expression vector wherein emrD gene was ligated to the downstream of lac promoter was constructed by the above-mentioned method and designated as pSemrD.

EXAMPLE 5

Construction of yeeO Gene Expression Plasmid

Based on the nucleotide sequence shown by SEQ ID NO: 5, the primer DNAs consisting of a nucleotide sequence shown by SEQ ID NO: 38 or 39 were synthesized in the same manner as Example 1 as primer DNAs for yeeO gene amplification. PCR was performed using these synthetic DNAs as a set of primers.

PCR was performed under similar conditions as in Example 1 except that the above-mentioned primer set was used as a primer DNA.

The amplified DNA fragment obtained by PCR and pSTV28 were digested with EcoRI and PstI, respectively. Both DNAs were ligated to each other in the same manner as in Example 1 and *Escherichia coli* DH5α strain was transformed with the ligated DNA. The expression vector wherein yeeO gene was ligated to the downstream of lac promoter was constructed by the above-mentioned method and designated as pSyeeO.

EXAMPLE 6

Construction of ywfE Gene and ald Gene Expression Plasmid (1) Construction of Expression Plasmid pTrSQE30

PCR was performed using DNAs consisting of the nucleotide sequence shown by SEQ ID NO: 40 or 41 as a set of primers and expression vector pQE60 (manufactured by QIAGEN K.K.) as a template.

PCR was performed by preparing 40 µL of a reaction mixture comprising 10 ng of plasmid DNA, 0.5 µmol/L of each of the primers, 2.5 units of Pfu DNA polymerase, 4 µL of buffer for Pfu DNA polymerase (10×) and 200 µmol/L each of dNTPs and repeating 30 times a cycle consisting of reaction at 94° C. for 1 min, reaction at 55° C. for 2 min and reaction at 72° C. for 3 min.

The amplified DNA fragment obtained by PCR and pTrS30 were digested with ClaI and SphI, respectively. Both DNAs were ligated to each other in the same manner as in Example 1 and *Escherichia coli* NM522 strain was transformed with the ligated DNA. A C-terminal His-tagged protein expression vector having trp promoter was constructed by the above-mentioned method and designated as pTrSQE30.

(2) Construction of Expression Plasmid pUATQE30

PCR was performed using DNAs consisting of the nucleotide sequence shown by SEQ ID NO: 42 or 43 as a set of primers and a chromosomal DNA of *Escherichia coli* W3110 as a template.

PCR was performed by preparing 40 µL of a reaction mixture comprising 0.1 µg of chromosomal DNA, 0.5 µmol/L of each of the primers, 2.5 units of Pfu DNA polymerase, 4 µL of buffer for Pfu DNA polymerase (10×) and 200 µmol/L each of dNTPs and repeating 30 times a cycle consisting of reaction at 94° C. for 1 min, reaction at 55° C. for 2 min and reaction at 72° C. for 3 min.

The amplified DNA fragment obtained by PCR and pTrSQE30 obtained above were digested with EcoRI and ClaI, respectively. Both DNAs were ligated to each other in the same manner as in Example 1 and *Escherichia coli* NM522 strain was transformed with the ligated DNA. A C-terminal His-tagged protein expression vector having a stress protein promoter (uspA promoter) was constructed by the above-mentioned method and designated as pUATQE30.

(3) Construction of ywfE Gene and ald Gene Expression Plasmid

PCR was performed using DNAs consisting of the nucleotide sequence shown by SEQ ID NO: 41 or 42 as a set of primers and pUATQE30 obtained above as a template.

PCR was performed by preparing 40 µL of a reaction mixture comprising 10 ng of plasmid, 0.5 µmol/L of each of the primers, 2.5 units of Pfu DNA polymerase, 4 µL of buffer for Pfu DNA polymerase (10×) and 200 µmol/L each of dNTPs and repeating 30 times a cycle consisting of reaction at 94° C. for 1 min, reaction at 55° C. for 2 min and reaction at 72° C. for 3 min.

The amplified DNA fragment obtained by PCR and pPE86 which is *Bacillus subtilis*-derived ywfE gene and *Bacillus subtilis*-derived ald gene expression plasmid (described in WO 2006/001379) were digested with EcoRI and NcoI, respectively. Both DNAs were ligated to each other in the same manner as in Example 1 and *Escherichia coli* NM522 strain was transformed with the ligated DNA. The expression plasmid wherein ywfE gene and ald gene are ligated to the downstream of uspA promoter was constructed by the above-mentioned method and designated as pPE86usp.

EXAMPLE 7

Preparation of Strain with Deletion of Pepd Gene, Pepn Gene, pepB Gene, pepA Gene, dpp Operon, glnE Gene and glnB Gene Using *Escherichia coli* JPNDBP7 (WO 2005/045006) wherein pepD gene, pepN gene, pepB gene and dpp operon were deleted as a parental strain, a strain without pepA gene, glnE gene and glnB gene on the chromosomal DNA thereof was prepared according to a method utilizing the homologous recombination system of lambda phage [Proc. Natl. Acad. Sci. USA, 97, 6641-6645 (2000)].

Plasmids pKD46, pKD3 and pCP20 described below were prepared by extraction from *Escherichia coli* strains carrying the plasmids, which were obtained from the *Escherichia coli* Genetic Stock Center (USA, Yale University), according to a known method.

(1) Cloning of DNA Fragment for Gene Deletion

The nucleotide sequences of pepA gene encoding peptidase of *Escherichia coli* K12 strain, putA gene involved in L-proline degradation, each gene of glnE and glnB involved in the control of L-glutamine biosynthesis have already been clarified [Science, 5331, 1453-1474 (1997)].

To delete respective genes of pepA, putA, glnE and glnB, DNAs having a nucleotide sequence homologous to 36 bp nucleotide sequence at the upstream and downstream of the respective genes to be deleted on the chromosomal DNA of *Escherichia coli* K12 strain and the nucleotide sequence to be recognized by yeast-derived Flp recombinase were synthesized based on the reported nucleotide sequences.

That is, DNAs having the nucleotide sequences shown by SEQ ID NOs: 40 and 41 as a primer set for amplification of DNA fragment for pepA gene deletion, DNAs consisting of the nucleotide sequences shown by SEQ ID NOs: 42 and 43 as a primer set for amplification of DNA fragment for putA gene deletion, DNAs having the nucleotide sequences shown by SEQ ID NOs: 44 and 45 as a primer set for amplification of DNA fragment for glnE gene deletion, DNAs consisting of the nucleotide sequences shown by SEQ ID NOs: 46 and 47 as a primer set for amplification of DNA fragment for glnB gene deletion were respectively synthesized.

Then, PCR was performed using the above-mentioned synthetic DNAs as a set of primers and pKD3DNA as a template. PCR was performed by repeating 30 times of a cycle consisting of reaction at 94° C. for 1 min, reaction at 55° C. for 2 min and reaction at 72° C. for 3 min, using 40 µL of the reaction mixture comprising 10 ng of plasmid DNA, 0.5 µmol/L of each of the primers, 2.5 units of Pfu DNA polymerase, 4 µL of buffer for Pfu DNA polymerase (10×) and 200 µmol/L each of deoxy NTPs.

The DNA fragments for deletion of pepA gene, putA gene, glnE gene or glnB gene, which contain chloramphenicol resistance gene, were obtained by the above-mentioned PCR.

(2) Preparation of pepA Gene Defective *Escherichia coli* JPNDBP7

*Escherichia coli* JPNDBP7 strain was transformed with pKD46, the transformant was spread on an LB agar medium containing 100 mg/L of ampicillin and cultured at 30° C. to select *Escherichia coli* JPNDBP7 strain carrying pKD46 (hereinafter referred to as *Escherichia coli* JPNDBP7/pKD46).

The plasmid pKD46 has λRed recombinase gene and the expression of this gene can be induced by L-arabinose. Therefore, homologous recombination occurs with high frequency when *Escherichia coli* carrying pKD46 cultured in the presence of L-arabinose is transformed with linear DNA. Moreover, since pKD46 has a temperature-sensitive replication origin, the plasmid can be cured easily by growing at 42° C.

A DNA fragment for pepD gene deletion obtained above, which contains a chloramphenicol resistance gene, was introduced into *Escherichia coli* JPNDBP7/pKD46 obtained by culturing in the presence of 10 mmol/L L-arabinose and 50 µg/ml ampicillin by electric pulse method. A transformant wherein the DNA fragment for pepA gene deletion containing a chloramphenicol resistance gene was incorporated onto the chromosomal DNA of *Escherichia coli* JPNDBP7 was spread on an LB agar medium (Bacto Tripton 10 g/L, Bacto Yeast Extract 5 g/L, sodium chloride 5 g/L, agar 15 g/L) containing 25 mg/L of chloramphenicol and cultured at 30° C. for selection.

The selected chloramphenicol resistance strain was inoculated into an LB agar medium containing 25 mg/L chloramphenicol, cultured for 14 hr at 42° C. and single colonies were separated. Each of the obtained colonies was replicated into an LB agar medium containing 25 mg/L of chloramphenicol and an LB agar medium containing 100 mg/l of ampicillin, cultured at 37° C., and the colonies showing chloramphenicol resistance and ampicillin sensitivity were selected to give pKD46-cured strain.

Then, the pKD46-cured strain obtained above was transformed with pCP20 and selected on an LB agar medium containing 100 mg/l of ampicillin to give pKD46-cured strain carrying pCP20.

The plasmid pCP20 has Flp recombinase gene derived from yeast and the expression of this gene can be induced at 42° C.

Also, the both ends of the DNA fragments for deletion of pepA gene, putA gene, glnE gene or glnB gene containing a chloramphenicol resistance gene, which were prepared above, have a nucleotide sequence recognizable by Flp recombinase. Therefore, the resistance gene can be easily cured by homologous recombination catalyzed by Flp recombinase.

Furthermore, Flp recombinase expression and curing of pCP20 can be introduced simultaneously by growing a strain carrying pCP20 at 42° C., since pCP20 has a temperature sensitive replication origin.

The pKD46-cured strain carrying pCP20 obtained above was inoculated into a drug-free LB agar medium, cultured for 14 hr at 42° C. and single colonies were separated. Each of the obtained colonies was replicated into a drug-free LB agar medium, an LB agar medium containing 25 mg/L of chloramphenicol and an LB agar medium containing 100 mg/L of ampicillin, cultured at 30° C. and the colonies showing chloramphenicol sensitivity and ampicillin sensitivity were selected.

The chromosomal DNA was prepared from each strain selected above. The strain confirmed by PCR to be pepA gene defective on the chromosomal DNA was taken as pepA gene defective strain and designated as *Escherichia coli* JPNDABP strain.

Then, using *Escherichia coli* JPNDABP strain as a parental strain and according to a method similar to the above, putA gene deletion, glnE gene deletion and glnB gene deletion were introduced in this order to give the strain having deletion of pepD, pepN, pepA, pepB, putA, glnE and glnB genes, as well as dpp operon multigene. The obtained strain was designated as *Escherichia coli* JPNDABPUTGEB strain.

EXAMPLE 8

Production of L-alanyl-L-glutamine (L-Ala-L-Gln)

JPNDABPUTGEB obtained in Example 7 was transformed with pPE86usp obtained in Example 6 to give *Escherichia coli* JPNDABPUTGEB/pPE86usp having an ability to produce a protein having a dipeptide synthase activity.

Then, *Escherichia coli* JPNDABPUTGEB/pPE86usp was transformed with pSbcr, pSnorE, pSydeE, pSemrD or pSyeeO, which was obtained in Examples 1-5. The obtained transformants were designated as *Escherichia coli* JPNDABPUTGEB/pPE86usp/pSbcr, JPNDABPUTGEB/pPE86usp/pSnorE, JPNDABPUTGEB/pPE86usp/pSydeE, JPNDABPUTGEB/pPE86usp/pSemrD, and JPNDABPUTGEB/pPE86usp/pSyeeO, respectively. In the same manner, a transformant (JPNDABPUTGEB/pPE86usp/pSTV28) carrying pSTV28 was also obtained.

The transformant obtained above was inoculated into a large test tube containing 8 ml of LB medium containing 50 µg/ml ampicillin and 25 µg/ml chloramphenicol and the mixture was cultured for 17 hr at 30° C. The cultured medium was added to a test tube containing 8 ml of a culture medium (16 g/L dipotassium hydrogen phosphate, 14 g/L potassium dihydrogen phosphate, 2 g/L ammonium sulfate, 1 g/L citric acid (anhydrous), 1 g/L casamino acid (manufactured by Difco), 10 g/L glucose, 10 mg/L vitamin $B_1$, 2 g/L magnesium sulfate 7 hydrate, 10 mg/L manganese sulfate 5 hydrate, 50 mg/L ferric sulfate 7 hydrate, 0.1 g/L L-Pro; adjusted to pH 7.2 with 10 mol/L of sodium hydroxide solution; glucose, vitamin $B_1$, magnesium sulfate 7 hydrate, ferric sulfate 7 hydrate, and L-Pro were added after separate autoclaving) to 1%, and the mixture was cultured for 24 hr at 30° C. The cultured medium was centrifuged to give supernatant. The cultured resultant product in the culture supernatant was derivatized by F-moc method, and the resultant product was analyzed by HPLC. The results are shown in Table 1.

TABLE 1

| strain | L-Ala-L-Gln (g/l) |
| --- | --- |
| JPNDABPUTGEB/pPE86usp/pSTV28 | 0.34 |
| JPNDABPUTGEB/pPE86usp/pSbcr | 0.55 |
| JPNDABPUTGEB/pPE86usp/pSnorE | 0.62 |
| JPNDABPUTGEB/pPE86usp/pSydeE | 0.69 |
| JPNDABPUTGEB/pPE86usp/pSemrD | 0.52 |
| JPNDABPUTGEB/pPE86usp/pSyeeO | 0.55 |

As shown in Table 1, the accumulation amount of L-Ala-L-Gln in the culture medium increased by enhancing the expression of bcr, norE, ydeE, emrD or yeeO gene. These results show that the above-mentioned gene products were proteins having an activity to transport a dipeptide, by which the dipeptide in the cell is extracellularly exported.

EXAMPLE 9

Production of L-Alanyl-L-Leucine (L-Ala-L-Leu), L-Alanyl-L-Valine (L-Ala-L-Val, L-Alanyl-L-Isoleucine (L-Ala-L-Ile), L-Alanyl-L-Tyrosine (L-Ala-L-Tyr)

*Escherichia coli* JPNDDP36 (WO 05/45006) was transformed with pPE86usp obtained in Example 6 and the obtained transformant was designated as JPNDDP36/pPE86usp. *Escherichia coli* JPNDDP36/pPE86usp was transformed with pSbcr, pSnorE, pSydeE, pSemrD and pSyeeO, which were obtained in Examples 1-5, respectively, and the obtained transformants were designated as *Escherichia coli* JPNDDP36/pPE86usp/pSbcr, JPNDDP36/pPE86usp/pSnorE, JPNDDP36/pPE86usp/pSydeE, JPNDDP36/pPE86usp/pSemrD and JPNDDP36/pPE86usp/pSyeeO, respectively. In the same manner, a transformant (JPNDDP36/pPE86usp/pSTV28) carrying pSTV28 was also obtained.

The transformant obtained above was inoculated into a large test tube containing 8 ml of LB medium containing 50 µg/ml ampicillin and 25 µg/ml chloramphenicol, and the mixture was cultured for 17 hr at 30° C. The cultured medium was added to a test tube containing 8 ml of an aqueous medium containing 100 µg/ml ampicillin, 25 µg/ml chloramphenicol and amino acid (L-Leu or L-Val or L-Ile or L-Tyr) (16 g/l dipotassium hydrogen phosphate, 14 g/l potassium dihydrogen phosphate, 2 g/l ammonium sulfate, 1 g/l citric acid (anhydrous), 1 g/l casamino acid (manufactured by Difco), 0.1 g/l L-Pro, 2 g/l L-Leu (or L-Val, L-Ile, L-Tyr), 10 g/l glucose, 10 mg/l vitamin $B_1$, 2 g/l magnesium sulfate 7 hydrate, 50 mg/l ferric sulfate 7 hydrate, 10 mg/l manganese sulfate 5 hydrate; adjusted to pH 7.2 with 10 mol/l of sodium hydroxide solution; glucose, vitamin $B_1$, magnesium sulfate 7 hydrate, ferric sulfate 7 hydrate and L-Pro were added after separate autoclaving) to 1%, and the mixture was cultured for 24 hr at 30° C. The aqueous medium was centrifuged to give supernatant.

The resultant product in the supernatant was derivatized by F-moc method, and the resultant product was analyzed by HPLC. The results are shown in Table 2.

TABLE 2

| strain | |
| --- | --- |
| | L-Ala-L-Leu (g/l) |
| JPNDDP36/pPE86usp/pSTV28 | 0.12 |
| JPNDDP36/pPE86usp/pSbcr | 0.29 |
| JPNDDP36/pPE86usp/pSnorE | 0.39 |
| JPNDDP36/pPE86usp/pSydeE | 0.39 |
| JPNDDP36/pPE86usp/pSemrD | 0.56 |
| JPNDDP36/pPE86usp/pSyeeO | 0.26 |
| | L-Ala-L-Val (g/l) |
| JPNDDP36/pPE86usp/pSTV28 | 0.68 |
| JPNDDP36/pPE86usp/pSbcr | 1.65 |
| JPNDDP36/pPE86usp/pSnorE | 1.40 |
| JPNDDP36/pPE86usp/pSydeE | 2.21 |
| JPNDDP36/pPE86usp/pSemrD | 1.25 |
| JPNDDP36/pPE86usp/pSyeeO | 1.46 |
| | L-Ala-L-Ile (g/l) |
| JPNDDP36/pPE86usp/pSTV28 | 0.26 |
| JPNDDP36/pPE86usp/pSbcr | 1.13 |
| JPNDDP36/pPE86usp/pSnorE | 0.84 |
| JPNDDP36/pPE86usp/pSydeE | 1.15 |
| JPNDDP36/pPE86usp/pSemrD | 0.43 |
| JPNDDP36/pPE86usp/pSyeeO | 0.51 |
| | L-Ala-L-Tyr (g/l) |
| JPNDDP36/pPE86usp/pSTV28 | 0.25 |
| JPNDDP36/pPE86usp/pSbcr | 0.33 |
| JPNDDP36/pPE86usp/pSnorE | 0.81 |
| JPNDDP36/pPE86usp/pSydeE | 0.54 |
| JPNDDP36/pPE86usp/pSemrD | 0.32 |
| JPNDDP36/pPE86usp/pSyeeO | 0.22 |

As shown in Table 2, the accumulation amounts of dipeptides other than L-Ala-L-Gln in the culture medium also increased by enhancing the expression of bcr, norE, ydeE, emrD or yeeO gene. These results show that the above-mentioned gene products are proteins having a transporting activity for dipeptides in general.

SEQUENCE LISTING FREE TEXT

SEQ ID NO: 30—explanation of artificial sequence: synthetic DNA
SEQ ID NO: 31—explanation of artificial sequence: synthetic DNA
SEQ ID NO: 32—explanation of artificial sequence: synthetic DNA
SEQ ID NO: 33—explanation of artificial sequence: synthetic DNA
SEQ ID NO: 34—explanation of artificial sequence: synthetic DNA
SEQ ID NO: 35—explanation of artificial sequence: synthetic DNA
SEQ ID NO: 36—explanation of artificial sequence: synthetic DNA
SEQ ID NO: 37—explanation of artificial sequence: synthetic DNA
SEQ ID NO: 38—explanation of artificial sequence: synthetic DNA
SEQ ID NO: 39—explanation of artificial sequence: synthetic DNA
SEQ ID NO: 40—explanation of artificial sequence: synthetic DNA
SEQ ID NO: 41—explanation of artificial sequence: synthetic DNA
SEQ ID NO: 42—explanation of artificial sequence: synthetic DNA
SEQ ID NO: 43—explanation of artificial sequence: synthetic DNA
SEQ ID NO: 44—explanation of artificial sequence: synthetic DNA
SEQ ID NO: 45—explanation of artificial sequence: synthetic DNA
SEQ ID NO: 46—explanation of artificial sequence: synthetic DNA
SEQ ID NO: 47—explanation of artificial sequence: synthetic DNA

INDUSTRIAL APPLICABILITY

According to the present invention, by enhancing the activity of a protein to transport a dipeptide in the microbial cell to the outside of the microbial cells of a microorganism, a dipeptide can be produced efficiently using the microorganism.

The invention claimed is:

1. A process for producing a dipeptide which comprises
(a) allowing (i) a culture of a microorganism or a treated culture of a microorganism selected from the group consisting of concentrated culture, microbial cells centrifuged and obtained from a culture, and immobilized microbial cells, having an ability to produce a protein having a dipeptide synthesizing activity and in which an activity of a protein having dipeptide transporting activity is higher than that of a parental strain, and (ii) an amino acid, amino acid ester or amino acid amide to be present in an aqueous medium,
(b) allowing the dipeptide to form and accumulate in the aqueous medium, and
(c) recovering the dipeptide from the aqueous medium, wherein the protein having a dipeptide transporting activity is selected from
(1) a protein having an amino acid sequence according to any one of SEQ ID NOs: 6 to 10,
(2) a protein consisting of an amino acid sequence wherein one to ten amino acids are deleted, substituted or added in the amino acid sequence according to any one of SEQ ID NOs: 6 to 10, and having a dipeptide transporting activity, and
(3) a protein having an amino acid sequence having at 95% or more identity with the amino acid sequence according to any one of SEQ ID NOs: 6 to 10, and having a dipeptide transporting activity, and wherein the dipeptide is selected from the group consisting of: L-Ala-L-Leu, L-Ala-L-Val, L-Ala-L-Ile, L-Ala-L-Tyr and L-Ala-L-Gln.

2. A process for producing a dipeptide which comprises
(a) culturing a microorganism having an ability to produce a protein having a dipeptide synthesizing activity and in which an activity of a protein having dipeptide transporting activity is higher than that of a parental strain, and which has an ability to produce at least one of the amino acids constituting the dipeptide in a medium,
(b) allowing the dipeptide to form and accumulate in the medium, and
(c) recovering the dipeptide from the culture, wherein the protein having a dipeptide transporting activity is selected from
(1) a protein having an amino acid sequence according to any one of SEQ ID NOs: 6to 10,
(2) a protein consisting of an amino acid sequence wherein one to ten amino acids are deleted, substituted or added in the amino acid sequence according to any one of SEQ ID NOs: 6 to 10, and having a dipeptide transporting activity, and
(3) a protein having an amino acid sequence having at 95% or more identity with the amino acid sequence according to any one of SEQ ID NOs: 6 to 10, and having a dipeptide transporting activity, and wherein the dipeptide is selected from the group consisting of: L-Ala-L-Leu, L-Ala-L-Val, L-Ala-L-Ile, L-Ala-L-Tyr and L-Ala-L-Gln.

3. The process of claim 2, wherein the microorganism belongs to the genus Escherichia, Corynebacterium, Bacillus, Serratia, Pseudomonas or Streptomyces.

4. The process of claim 1, wherein the microorganism is obtained by transforming the parental strain with a DNA selected from
(a) a DNA encoding a protein according to any one of (1) to (3) of claim 1,
(b) a DNA having a coding region having the nucleotide sequence according to any one of SEQ ID NOs: 1 to 5,
(c) a DNA hybridizing with a DNA consisting of a nucleotide sequence which is complementary to a DNA having a coding region having the nucleotide sequence according to any one of SEQ ID NOs: 1 to 5 under stringent conditions, and encoding the protein having a dipeptide transporting activity.

5. The process of claim 4, wherein the microorganism belongs to the genus Escherichia, Corynebacterium, Bacillus, Serratia, Pseudomonas or Streptomyces.

6. The process of claim 2, wherein the microorganism is obtained by transforming the parental strain with a DNA selected from
(a) a DNA encoding a protein according to any one of (1) to (3) of claim 2,
(b) a DNA having a coding region having the nucleotide sequence according to any one of SEQ ID NOs: 1 to 5,
(c) a DNA hybridizing with a DNA consisting of a nucleotide sequence which is complementary to a DNA having a coding region having the nucleotide sequence according to any one of SEQ ID NOs: 1 to 5 under stringent conditions, and encoding the protein having a dipeptide transporting activity.

7. The process of claim 6, wherein the microorganism belongs to the genus *Escherichia, Corynebacterium, Bacillus, Serratia, Pseudomonas* or *Streptomyces*.

8. The process of claim 1, wherein the microorganism belongs to the genus *Escherichia, Corynebacterium, Bacillus, Serratia, Pseudomonas* or *Streptomyces*.

* * * * *

```
                          SEQUENCE LISTING

<160> NUMBER OF SEQ ID NOS: 47

<210> SEQ ID NO 1
<211> LENGTH: 1491
<212> TYPE: DNA
<213> ORGANISM: Escherichia coli
<220> FEATURE:
<221> NAME/KEY: CDS
<222> LOCATION: (201)..(1388)

<400> SEQUENCE: 1
gtctgaccat cagcgaaggg cgttatcatc aggtgaaacg catgttcgcc gccgtgggta      60
accacgtggt tgagctgcat cgtgaacgta ttggcggtat tacgctggat gctgatttag     120
cccccggtga atatcgtccg ttaactgaag aagaaattgc cagcgtcgtc taacttttca     180
atgactttca ggagcccgtt gtg acc acc cga cag cat tcg tcg ttt gct att     233
                      Met Thr Thr Arg Gln His Ser Ser Phe Ala Ile
                       1               5                  10 gtt ttt atc ctt ggc ctg ctg gcc atg ttg atg ccg ctg tcg att gat       281
Val Phe Ile Leu Gly Leu Leu Ala Met Leu Met Pro Leu Ser Ile Asp
            15                  20                  25 atg tat ctg ccc gcg cta ccg gta att tca gcg cag ttt ggc gta ccg       329
Met Tyr Leu Pro Ala Leu Pro Val Ile Ser Ala Gln Phe Gly Val Pro
        30                  35                  40 gcg ggc agt acg cag atg acc ctc agt act tat att ctg ggc ttt gcg       377
Ala Gly Ser Thr Gln Met Thr Leu Ser Thr Tyr Ile Leu Gly Phe Ala
    45                  50                  55 ttg ggg cag tta atc tac ggg ccg atg gca gac agc ttc ggg cgt aag       425
Leu Gly Gln Leu Ile Tyr Gly Pro Met Ala Asp Ser Phe Gly Arg Lys
60                  65                  70                  75 ccg gtg gtg ctc ggc ggt acg ctg gtg ttt gcc gcc gcc gcg gtg gcg       473
Pro Val Val Leu Gly Gly Thr Leu Val Phe Ala Ala Ala Ala Val Ala
                80                  85                  90 tgt gcg ttg gca aac acc atc gat cag ctg att gtg atg cgt ttc ttc       521
Cys Ala Leu Ala Asn Thr Ile Asp Gln Leu Ile Val Met Arg Phe Phe
            95                 100                 105
```

```
cac ggg ctg gct gcg gct gcg gcc agc gtg gtc att aac gcc ctg atg      569
His Gly Leu Ala Ala Ala Ala Ala Ser Val Val Ile Asn Ala Leu Met
        110                 115                 120 cgc gat att tac ccg aaa gaa gag ttc tcg cgg atg atg tcg ttt gtc      617
Arg Asp Ile Tyr Pro Lys Glu Glu Phe Ser Arg Met Met Ser Phe Val
    125                 130                 135 atg ctg gtg aca acc att gca ccg ctg atg gca ccg ata gtt ggc ggc      665
Met Leu Val Thr Thr Ile Ala Pro Leu Met Ala Pro Ile Val Gly Gly
140                 145                 150                 155 tgg gtg ctg gtg tgg ctg agc tgg cat tac atc ttc tgg atc ctg gca      713
Trp Val Leu Val Trp Leu Ser Trp His Tyr Ile Phe Trp Ile Leu Ala
                160                 165                 170 tta gcg gcg att ctg gct tcg gca atg att ttc ttc ctg att aaa gaa      761
Leu Ala Ala Ile Leu Ala Ser Ala Met Ile Phe Phe Leu Ile Lys Glu
            175                 180                 185 acc tta cca ccg gag cgt cgt cag cca ttt cac att cgt acc act att      809
Thr Leu Pro Pro Glu Arg Arg Gln Pro Phe His Ile Arg Thr Thr Ile
        190                 195                 200 ggt aac ttt gcg gcg ctg ttc cgc cat aaa cgt gtc ctg agc tac atg      857
Gly Asn Phe Ala Ala Leu Phe Arg His Lys Arg Val Leu Ser Tyr Met
    205                 210                 215 ctt gcc agt ggt ttc agc ttt gcc ggg atg ttc tca ttc tta agc gcc      905
Leu Ala Ser Gly Phe Ser Phe Ala Gly Met Phe Ser Phe Leu Ser Ala
220                 225                 230                 235 gga ccg ttt gtt tat att gaa att aac cac gtc gcg ccg gaa aac ttt      953
Gly Pro Phe Val Tyr Ile Glu Ile Asn His Val Ala Pro Glu Asn Phe
                240                 245                 250 ggt tat tac ttt gcg cta aac att gtt ttt ctg ttc gtg atg acc atc     1001
Gly Tyr Tyr Phe Ala Leu Asn Ile Val Phe Leu Phe Val Met Thr Ile
            255                 260                 265 ttt aac agc cgc ttc gtc cgc cgc att ggc gcg tta aat atg ttc cgc     1049
Phe Asn Ser Arg Phe Val Arg Arg Ile Gly Ala Leu Asn Met Phe Arg
        270                 275                 280 tcg ggg ttg tgg ata caa ttt att atg gca gcg tgg atg gtc atc agt     1097
Ser Gly Leu Trp Ile Gln Phe Ile Met Ala Ala Trp Met Val Ile Ser
    285                 290                 295 gcg ctg ctg ggg ctg gga ttt tgg tcg ctg gtg gtt ggc gtt gcg gcg     1145
Ala Leu Leu Gly Leu Gly Phe Trp Ser Leu Val Val Gly Val Ala Ala
300                 305                 310                 315 ttt gtg ggc tgc gtg tcg atg gtg tca tcc aat gcg atg gcg gtc att     1193
Phe Val Gly Cys Val Ser Met Val Ser Ser Asn Ala Met Ala Val Ile
                320                 325                 330 ctt gat gag ttt ccc cat atg gcg gga acg gca tct tcg ctg gca gga     1241
Leu Asp Glu Phe Pro His Met Ala Gly Thr Ala Ser Ser Leu Ala Gly
            335                 340                 345 acc ttc cgt ttt ggc ata ggg gca att gtt ggc gca ttg ctt tct ctt     1289
Thr Phe Arg Phe Gly Ile Gly Ala Ile Val Gly Ala Leu Leu Ser Leu
        350                 355                 360 gcg acc ttt aac tct gca tgg ccg atg att tgg tca att gca ttc tgc     1337
Ala Thr Phe Asn Ser Ala Trp Pro Met Ile Trp Ser Ile Ala Phe Cys
    365                 370                 375 gca acc agc tcc att ctc ttc tgt ctg tac gcc agt cgg ccg aaa aaa     1385
Ala Thr Ser Ser Ile Leu Phe Cys Leu Tyr Ala Ser Arg Pro Lys Lys
380                 385                 390                 395 cgg tgatctattg cacaacgagg aagctaaaag gcttcctttg ttgatgcatg          1438
Arg tcaaccacaa atctatcatt cccccgatat atgtttattt tatgtaaaat caa          1491

<210> SEQ ID NO 2
<211> LENGTH: 1674
```

<212> TYPE: DNA
<213> ORGANISM: Escherichia coli
<220> FEATURE:
<221> NAME/KEY: CDS
<222> LOCATION: (201)..(1571)

<400> SEQUENCE: 2

```
aaatcagtta agacattctg ttcagcacaa tagcaggtgg aaaacgccct taccagtgaa      60
ggggtaagaa tggctatttt ttcactggag aattaataaa tcctcgctac aatagactga     120
atttcccctg cttcttcttt tgctgccca ttcaggcggc ttttagtct ctcatataac       180 tacaaataaa aggtgttcac gtg cag aag tat atc agt gaa gcg cgt ctg tta    233
                      Met Gln Lys Tyr Ile Ser Glu Ala Arg Leu Leu
                       1               5                  10
```

| tta gca tta gca atc ccg gtg att ctc gcg caa atc gcc caa act gcg | 281 |
|---|---|
| Leu Ala Leu Ala Ile Pro Val Ile Leu Ala Gln Ile Ala Gln Thr Ala | |
|         15                  20                  25 | |

| atg ggt ttt gtc gat acc gtg atg gcg ggc ggc tat agt gcc acc gac | 329 |
|---|---|
| Met Gly Phe Val Asp Thr Val Met Ala Gly Gly Tyr Ser Ala Thr Asp | |
|         30                  35                  40 | |

| atg gcg gcg gtc gct atc ggt act tct atc tgg ctt ccg gcg atc ctc | 377 |
|---|---|
| Met Ala Ala Val Ala Ile Gly Thr Ser Ile Trp Leu Pro Ala Ile Leu | |
|     45                  50                  55 | |

| ttt ggt cac gga ctg ctg ctg gca tta acg ccg gtt atc gcg caa tta | 425 |
|---|---|
| Phe Gly His Gly Leu Leu Leu Ala Leu Thr Pro Val Ile Ala Gln Leu | |
| 60                  65                  70                  75 | |

| aat ggt tcc ggt cga cgt gag cgc att gcg cat cag gtg cga caa ggt | 473 |
|---|---|
| Asn Gly Ser Gly Arg Arg Glu Arg Ile Ala His Gln Val Arg Gln Gly | |
|         80                  85                  90 | |

| ttc tgg ctg gca ggt ttt gtt tcc gtt ctc att atg ctg gtg ctg tgg | 521 |
|---|---|
| Phe Trp Leu Ala Gly Phe Val Ser Val Leu Ile Met Leu Val Leu Trp | |
|         95                 100                 105 | |

| aat gca ggt tac att atc cgc tcc atg gaa aac atc gat ccg gct ctg | 569 |
|---|---|
| Asn Ala Gly Tyr Ile Ile Arg Ser Met Glu Asn Ile Asp Pro Ala Leu | |
|         110                 115                 120 | |

| gcg gac aaa gcc gtg ggt tat ctg cgt gcg ttg ttg tgg ggc gcg ccg | 617 |
|---|---|
| Ala Asp Lys Ala Val Gly Tyr Leu Arg Ala Leu Leu Trp Gly Ala Pro | |
|     125                 130                 135 | |

| gga tat ctg ttc ttc cag gtt gcc cgt aac cag tgt gaa ggt ctg gca | 665 |
|---|---|
| Gly Tyr Leu Phe Phe Gln Val Ala Arg Asn Gln Cys Glu Gly Leu Ala | |
| 140                 145                 150                 155 | |

| aaa acc aag ccg ggt atg gta atg ggc ttt atc ggc ctg ctg gtg aac | 713 |
|---|---|
| Lys Thr Lys Pro Gly Met Val Met Gly Phe Ile Gly Leu Leu Val Asn | |
|         160                 165                 170 | |

| atc ccg gtg aac tat atc ttt att tat ggt cat ttc ggt atg cct gag | 761 |
|---|---|
| Ile Pro Val Asn Tyr Ile Phe Ile Tyr Gly His Phe Gly Met Pro Glu | |
|         175                 180                 185 | |

| ctc ggt ggc gtt ggt tgt ggc gtg gct act gcg gcg gtg tat tgg gtc | 809 |
|---|---|
| Leu Gly Gly Val Gly Cys Gly Val Ala Thr Ala Ala Val Tyr Trp Val | |
|         190                 195                 200 | |

| atg ttc ctt gcc atg gtt tct tac att aaa cgc gcc cgc tcc atg cgc | 857 |
|---|---|
| Met Phe Leu Ala Met Val Ser Tyr Ile Lys Arg Ala Arg Ser Met Arg | |
|     205                 210                 215 | |

| gat att cgt aac gaa aaa ggc acc gca aaa ccc gat cct gcg gtt atg | 905 |
|---|---|
| Asp Ile Arg Asn Glu Lys Gly Thr Ala Lys Pro Asp Pro Ala Val Met | |
| 220                 225                 230                 235 | |

| aaa cga ctg att caa ctc ggt ttg ccg att gcg ctg gca ctg ttc ttt | 953 |
|---|---|
| Lys Arg Leu Ile Gln Leu Gly Leu Pro Ile Ala Leu Ala Leu Phe Phe | |
|         240                 245                 250 | |

| gaa gtg aca ctg ttt gcc gtc gtg gct ctg tta gtg tct ccg ctc ggt | 1001 |
|---|---|
| Glu Val Thr Leu Phe Ala Val Val Ala Leu Leu Val Ser Pro Leu Gly | |

```
                        255                 260                 265
att gtt gat gtc gca gga cac cag att gcc ctg aac ttt agt tca cta       1049
Ile Val Asp Val Ala Gly His Gln Ile Ala Leu Asn Phe Ser Ser Leu
                270                 275                 280 atg ttc gtg ctt cca atg tcg ctg gcg gca gcg gta act atc cgc gta       1097
Met Phe Val Leu Pro Met Ser Leu Ala Ala Ala Val Thr Ile Arg Val
        285                 290                 295 ggt tat cgt ctg ggt cag ggc tca acg ctg gat gcg caa acc gct gcg       1145
Gly Tyr Arg Leu Gly Gln Gly Ser Thr Leu Asp Ala Gln Thr Ala Ala
300                 305                 310                 315 cgg acc ggg ctt atg gtg ggt gtc tgt atg gca acc ctg acg gcc att       1193
Arg Thr Gly Leu Met Val Gly Val Cys Met Ala Thr Leu Thr Ala Ile
                320                 325                 330 ttc acg gtt tca ctg cgg gag caa atc gcc ctg ttg tac aac gac aat       1241
Phe Thr Val Ser Leu Arg Glu Gln Ile Ala Leu Leu Tyr Asn Asp Asn
        335                 340                 345 ccc gag gtt gta acg ctg gct gcg cat ttg atg ttg ctg gcg gcg gta       1289
Pro Glu Val Val Thr Leu Ala Ala His Leu Met Leu Leu Ala Ala Val
350                 355                 360 tat cag att tct gac tca atc cag gtg att ggc agt ggg att ttg cgt       1337
Tyr Gln Ile Ser Asp Ser Ile Gln Val Ile Gly Ser Gly Ile Leu Arg
                365                 370                 375 ggt tat aaa gat acg cgt tcc att ttc tat att acc ttt acg gct tac       1385
Gly Tyr Lys Asp Thr Arg Ser Ile Phe Tyr Ile Thr Phe Thr Ala Tyr
380                 385                 390                 395 tgg gtg ctg ggc ttg cca agc ggc tat att ctg gca ctg acc gat ctg       1433
Trp Val Leu Gly Leu Pro Ser Gly Tyr Ile Leu Ala Leu Thr Asp Leu
                400                 405                 410 gtc gtt gaa cct atg ggg cca gca ggc ttc tgg ata ggc ttt att att       1481
Val Val Glu Pro Met Gly Pro Ala Gly Phe Trp Ile Gly Phe Ile Ile
        415                 420                 425 ggc ctg acg tcg gca gcc att atg atg atg ttg cgt atg cgg ttc ctg       1529
Gly Leu Thr Ser Ala Ala Ile Met Met Met Leu Arg Met Arg Phe Leu
430                 435                 440 caa cgt ctg ccg tca gcc atc att ctg caa cga gca tcc cgc                1571
Gln Arg Leu Pro Ser Ala Ile Ile Leu Gln Arg Ala Ser Arg
        445                 450                 455 taataaagac aaggcgcaac cttcacgggt tgcgcctgta ttttacgca ggctggagcg      1631 ttgcgccaat cccgtcttcg tctggctgta atttcagagc gtt                        1674

<210> SEQ ID NO 3
<211> LENGTH: 1488
<212> TYPE: DNA
<213> ORGANISM: Escherichia coli
<220> FEATURE:
<221> NAME/KEY: CDS
<222> LOCATION: (201)..(1385)

<400> SEQUENCE: 3
cgacattcta ccgcctctga atttcatctt ttgtaagcaa tcaacttagc tgaatttact        60
tttctttaac agttgattcg ttagtcgccg gttacgacgg cattaatgcg caaataagtc      120
gctatacttc ggattttgc catgctattt ctttacatct ctaaaacaaa acataacgaa       180
acgcactgcc ggacagacaa atg aac tta tcc cta cga cgc tct acc agc gcc      233
                        Met Asn Leu Ser Leu Arg Arg Ser Thr Ser Ala
                         1               5                  10 ctt ctt gcc tcg tcg ttg tta tta acc atc gga cgc ggc gct acg ctg       281
Leu Leu Ala Ser Ser Leu Leu Leu Thr Ile Gly Arg Gly Ala Thr Leu
        15                  20                  25 cca ttt atg acc att tac ttg agt cgc cag tac agc ctg agt gtc gat       329
```

```
                Pro Phe Met Thr Ile Tyr Leu Ser Arg Gln Tyr Ser Leu Ser Val Asp
                        30                  35                  40 cta atc ggt tat gcg atg aca att gcg ctc act att ggc gtc gtt ttt       377
Leu Ile Gly Tyr Ala Met Thr Ile Ala Leu Thr Ile Gly Val Val Phe
         45                  50                  55 agc ctc ggt ttt ggt atc ctg gcg gat aag ttc gac aag aaa cgc tat       425
Ser Leu Gly Phe Gly Ile Leu Ala Asp Lys Phe Asp Lys Lys Arg Tyr
 60                  65                  70                  75 atg tta ctg gca att acc gcc ttc gcc agc ggt ttt att gcc att act       473
Met Leu Leu Ala Ile Thr Ala Phe Ala Ser Gly Phe Ile Ala Ile Thr
                 80                  85                  90 tta gtg aat aac gtg acg ctg gtt gtg ctc ttt ttt gcc ctc att aac       521
Leu Val Asn Asn Val Thr Leu Val Val Leu Phe Phe Ala Leu Ile Asn
         95                 100                 105 tgc gcc tat tct gtt ttt gct acc gtg ctg aaa gcc tgg ttt gcc gac       569
Cys Ala Tyr Ser Val Phe Ala Thr Val Leu Lys Ala Trp Phe Ala Asp
110                 115                 120 aat ctt tcg tcc acc agc aaa acg aaa atc ttc tca atc aac tac acc       617
Asn Leu Ser Ser Thr Ser Lys Thr Lys Ile Phe Ser Ile Asn Tyr Thr
         125                 130                 135 atg cta aac att ggc tgg acc atc ggt ccg ccg ctc ggc acg ctg ttg       665
Met Leu Asn Ile Gly Trp Thr Ile Gly Pro Pro Leu Gly Thr Leu Leu
140                 145                 150                 155 gta atg cag agc atc aat ctg ccc ttc tgg ctg gca gct atc tgt tcc       713
Val Met Gln Ser Ile Asn Leu Pro Phe Trp Leu Ala Ala Ile Cys Ser
                 160                 165                 170 gcg ttt ccc atg ctt ttc att caa att tgg gta aag cgc agc gag aaa       761
Ala Phe Pro Met Leu Phe Ile Gln Ile Trp Val Lys Arg Ser Glu Lys
         175                 180                 185 atc atc gcc acg gaa aca ggc agt gtc tgg tcg ccg aaa gtt tta tta       809
Ile Ile Ala Thr Glu Thr Gly Ser Val Trp Ser Pro Lys Val Leu Leu
190                 195                 200 caa gat aaa gca ctg ttg tgg ttt acc tgc tct ggt ttt ctg gct tct       857
Gln Asp Lys Ala Leu Leu Trp Phe Thr Cys Ser Gly Phe Leu Ala Ser
         205                 210                 215 ttt gta agc ggc gca ttt gct tca tgc att tca caa tat gtg atg gtg       905
Phe Val Ser Gly Ala Phe Ala Ser Cys Ile Ser Gln Tyr Val Met Val
220                 225                 230                 235 att gct gat ggg gat ttt gcc gaa aag gtg gtc gcg gtt gtt ctt ccg       953
Ile Ala Asp Gly Asp Phe Ala Glu Lys Val Val Ala Val Val Leu Pro
                 240                 245                 250 gtg aat gct gcc atg gtg gtt acg ttg caa tat tcc gtg ggc cgc cga      1001
Val Asn Ala Ala Met Val Val Thr Leu Gln Tyr Ser Val Gly Arg Arg
         255                 260                 265 ctt aac ccg gct aac atc cgc gcg ctg atg aca gca ggc acc ctc tgt      1049
Leu Asn Pro Ala Asn Ile Arg Ala Leu Met Thr Ala Gly Thr Leu Cys
270                 275                 280 ttc gtc atc ggt ctg gtc ggt ttt att ttt tcc ggc aac agc ctg cta      1097
Phe Val Ile Gly Leu Val Gly Phe Ile Phe Ser Gly Asn Ser Leu Leu
         285                 290                 295 ttg tgg ggt atg tca gct gcg gta ttt act gtc ggt gaa atc att tat      1145
Leu Trp Gly Met Ser Ala Ala Val Phe Thr Val Gly Glu Ile Ile Tyr
300                 305                 310                 315 gcg ccg ggc gag tat atg ttg att gac cat att gcg ccg cca gaa atg      1193
Ala Pro Gly Glu Tyr Met Leu Ile Asp His Ile Ala Pro Pro Glu Met
                 320                 325                 330 aaa gcc agc tat ttt tcc gcc cag tct tta ggc tgg ctt ggt gcc gcg      1241
Lys Ala Ser Tyr Phe Ser Ala Gln Ser Leu Gly Trp Leu Gly Ala Ala
         335                 340                 345 att aac cca tta gtg agt ggc gta gtg cta acc agc ctg ccg cct tcc      1289
```

```
                 Ile Asn Pro Leu Val Ser Gly Val Val Leu Thr Ser Leu Pro Pro Ser
                         350                 355                 360 tcg ctg ttt gtc atc tta gcg ttg gtg atc att gct gcg tgg gtg ctg                    1337
Ser Leu Phe Val Ile Leu Ala Leu Val Ile Ile Ala Ala Trp Val Leu
        365                 370                 375 atg tta aaa ggg att cga gca aga ccg tgg ggg cag ccc gcg ctt tgt                    1385
Met Leu Lys Gly Ile Arg Ala Arg Pro Trp Gly Gln Pro Ala Leu Cys
380                 385                 390                 395 tgatttaagt cgaacacaat aaagatttaa ttcagccttc gtttaggtta cctctgctaa                  1445
tatctttctc attgagatga aaattaaggt aagcgaggaa aca                                    1488

<210> SEQ ID NO 4
<211> LENGTH: 1485
<212> TYPE: DNA
<213> ORGANISM: Escherichia coli
<220> FEATURE:
<221> NAME/KEY: CDS
<222> LOCATION: (201)..(1382)

<400> SEQUENCE: 4
atgctgacgc atcttatccg ccctaccatc tctcccggca acatttattg ccgcttttgt                    60
ttacatattc tgccgctaaa caattcccca ttcctggcgt atatctggct aacattcatc                   120
aatgtgatag attcctctcc cgcatttatg ggaatgcgta gtgacttatt ctaattattt                   180
ttataaaagc atccgtgata atg aaa agg caa aga aac gtc aat ttg tta ttg                   233
                         Met Lys Arg Gln Arg Asn Val Asn Leu Leu Leu
                         1               5                   10 atg ttg gta tta ctc gtg gcc gtc ggt cag atg gcg caa acc att tat                    281
Met Leu Val Leu Leu Val Ala Val Gly Gln Met Ala Gln Thr Ile Tyr
        15                  20                  25 att cca gct att gcc gat atg gcg cgc gat ctc aac gtc cgt gaa ggg                    329
Ile Pro Ala Ile Ala Asp Met Ala Arg Asp Leu Asn Val Arg Glu Gly
                30                  35                  40 gcg gtg cag agc gta atg ggc gct tat ctg ctg act tac ggt gtc tca                    377
Ala Val Gln Ser Val Met Gly Ala Tyr Leu Leu Thr Tyr Gly Val Ser
45                  50                  55 cag ctg ttt tat ggc ccg att tcc gac cgc gtg ggc cgc cga ccg gtg                    425
Gln Leu Phe Tyr Gly Pro Ile Ser Asp Arg Val Gly Arg Arg Pro Val
60                  65                  70                  75 atc ctc gtc gga atg tcc att ttt atg ctg gca acg ctg gtc gcg gtc                    473
Ile Leu Val Gly Met Ser Ile Phe Met Leu Ala Thr Leu Val Ala Val
                80                  85                  90 acg acc tcc agt ttg acg gtg ttg att gcc gcc agc gcg atg cag ggg                    521
Thr Thr Ser Ser Leu Thr Val Leu Ile Ala Ala Ser Ala Met Gln Gly
        95                  100                 105 atg ggc acc ggc gtt ggc ggc gta atg gcg cgt act tta ccg cga gat                    569
Met Gly Thr Gly Val Gly Gly Val Met Ala Arg Thr Leu Pro Arg Asp
            110                 115                 120 tta tat gaa cgg aca cag ttg cgc cat gct aac agc ctg tta aac atg                    617
Leu Tyr Glu Arg Thr Gln Leu Arg His Ala Asn Ser Leu Leu Asn Met
        125                 130                 135 ggg att ctc gtc agt ccg ttg ctc gca ccg cta atc ggc ggt ctg ctg                    665
Gly Ile Leu Val Ser Pro Leu Leu Ala Pro Leu Ile Gly Gly Leu Leu
140                 145                 150                 155 gat acg atg tgg aac tgg cgc gcc tgt tat ctc ttt ttg ttg gtt ctt                    713
Asp Thr Met Trp Asn Trp Arg Ala Cys Tyr Leu Phe Leu Leu Val Leu
                160                 165                 170 tgt gct ggt gtg acc ttc agt atg gcc cgc tgg atg ccg gaa acg cgt                    761
Cys Ala Gly Val Thr Phe Ser Met Ala Arg Trp Met Pro Glu Thr Arg
        175                 180                 185
```

```
ccg gtc gat gca ccg cgc acg cgc ctg ctt acc agt tat aaa acg ctt      809
Pro Val Asp Ala Pro Arg Thr Arg Leu Leu Thr Ser Tyr Lys Thr Leu
        190                 195                 200 ttc ggt aac agc ggt ttt aac tgt tat ttg ctg atg ctg att ggc ggt      857
Phe Gly Asn Ser Gly Phe Asn Cys Tyr Leu Leu Met Leu Ile Gly Gly
    205                 210                 215 ctg gcc ggg att gcc gcc ttt gaa gcc tgc tcc ggc gtg ctg atg ggc      905
Leu Ala Gly Ile Ala Ala Phe Glu Ala Cys Ser Gly Val Leu Met Gly
220                 225                 230                 235 gcg gtg tta ggg ctg agc agt atg acg gtc agt att ttg ttt att ctg      953
Ala Val Leu Gly Leu Ser Ser Met Thr Val Ser Ile Leu Phe Ile Leu
                240                 245                 250 ccg att ccg gca gcg ttt ttt ggc gca tgg ttt gcc gga cgt ccc aat     1001
Pro Ile Pro Ala Ala Phe Phe Gly Ala Trp Phe Ala Gly Arg Pro Asn
            255                 260                 265 aaa cgc ttc tcc acg tta atg tgg cag tcg gtt atc tgc tgc ctg ctg     1049
Lys Arg Phe Ser Thr Leu Met Trp Gln Ser Val Ile Cys Cys Leu Leu
        270                 275                 280 gct ggc ttg ctg atg tgg atc ccc gac tgg ttt ggc gtg atg aat gtc     1097
Ala Gly Leu Leu Met Trp Ile Pro Asp Trp Phe Gly Val Met Asn Val
    285                 290                 295 tgg acg ctg ctc gtt ccc gcc gcg ctg ttc ttt ttc ggt gcc ggg atg     1145
Trp Thr Leu Leu Val Pro Ala Ala Leu Phe Phe Phe Gly Ala Gly Met
300                 305                 310                 315 ctg ttt ccg ctg gcg acc agc ggc gcg atg gag ccg ttc ccc ttc ctg     1193
Leu Phe Pro Leu Ala Thr Ser Gly Ala Met Glu Pro Phe Pro Phe Leu
                320                 325                 330 gcg ggc acg gct ggc gcg ctg gtc ggc ggt ctg caa aac att ggt tcc     1241
Ala Gly Thr Ala Gly Ala Leu Val Gly Gly Leu Gln Asn Ile Gly Ser
            335                 340                 345 ggc gtg ctg gcg tcg ctc tct gcg atg ttg ccg caa acc ggt cag ggc     1289
Gly Val Leu Ala Ser Leu Ser Ala Met Leu Pro Gln Thr Gly Gln Gly
        350                 355                 360 agc ctg ggg ttg ttg atg acc tta atg gga ttg atc gtg ctg tgc         1337
Ser Leu Gly Leu Leu Met Thr Leu Met Gly Leu Ile Val Leu Cys
    365                 370                 375 tgg ctg ccg ctg gcg acg cgg atg tcg cat cag ggg cag ccc gtt         1382
Trp Leu Pro Leu Ala Thr Arg Met Ser His Gln Gly Gln Pro Val
380                 385                 390 taagcgcacg tcaccgcagc atcgtcatca gctccatggg agaacgatgc tgctttatca    1442
gatcacgcat cacccgcata tgcggtgcgg agtaagaata aaa                     1485

<210> SEQ ID NO 5
<211> LENGTH: 1944
<212> TYPE: DNA
<213> ORGANISM: Escherichia coli
<220> FEATURE:
<221> NAME/KEY: CDS
<222> LOCATION: (201)..(1841)

<400> SEQUENCE: 5
tttgtaatgc aggactgtca gttgaggata tcaagcggca ggtgatggaa agcagtgaag     60
aggaaattga ttatcagata tagcaaaaat cccgctataa aagcgggctt ttcaggaatt    120
tggctcctct gactggactc gaaccagtga catacggatt aacagtccgc cgttctaccg    180
actgaactac agaggaatcg ttg ttg agg cac atc tta acg gcg aaa aat ctt    233
                         Met Leu Arg His Ile Leu Thr Ala Lys Asn Leu
                           1               5                  10 ttg tca aac ccg att ttt aaa ttc ccc aac tgt ttg ccg ttt cta tca     281
Leu Ser Asn Pro Ile Phe Lys Phe Pro Asn Cys Leu Pro Phe Leu Ser
            15                  20                  25
```

| | | |
|---|---|---|
| aca gtt tgt tgc att tgc aga caa ttt gtt ggc gaa aat ctt tgc agc<br>Thr Val Cys Cys Ile Cys Arg Gln Phe Val Gly Glu Asn Leu Cys Ser<br>     30                    35                      40 | 329 | |
| ttt gct gat tct ccc tca tta ttt gaa atg tgg ttt cac ttt ctg caa<br>Phe Ala Asp Ser Pro Ser Leu Phe Glu Met Trp Phe His Phe Leu Gln<br>45                      50                    55 | 377 | |
| tta agg tcg gct ttg aat atc tcc tct gct tta cgc cag gtt gtt cac<br>Leu Arg Ser Ala Leu Asn Ile Ser Ser Ala Leu Arg Gln Val Val His<br>60                      65                    70                    75 | 425 | |
| ggc act cgc tgg cac gct aaa cgc aag agc tac aaa gtg ttg ttc tgg<br>Gly Thr Arg Trp His Ala Lys Arg Lys Ser Tyr Lys Val Leu Phe Trp<br>                80                    85                    90 | 473 | |
| cgc gag ata acc ccg ctt gct gtt cct atc ttc atg gag aat gcc tgt<br>Arg Glu Ile Thr Pro Leu Ala Val Pro Ile Phe Met Glu Asn Ala Cys<br>                     95                      100                  105 | 521 | |
| gtc ctg ttg atg ggg gtt ctg agc act ttt ctg gtc agc tgg ctg gga<br>Val Leu Leu Met Gly Val Leu Ser Thr Phe Leu Val Ser Trp Leu Gly<br>          110                      115                    120 | 569 | |
| aaa gat gcg atg gcc ggc gtg gga ttg gcg gac agc ttc aat atg gtc<br>Lys Asp Ala Met Ala Gly Val Gly Leu Ala Asp Ser Phe Asn Met Val<br>        125                      130                    135 | 617 | |
| att atg gct ttt ttt gct gct atc gat ctt ggt act act gtc gtt gtg<br>Ile Met Ala Phe Phe Ala Ala Ile Asp Leu Gly Thr Thr Val Val Val<br>140                      145                    150                  155 | 665 | |
| gca ttt agt ctc ggt aag cgg gat cga cga cga gcg agg gtg gcg acg<br>Ala Phe Ser Leu Gly Lys Arg Asp Arg Arg Arg Ala Arg Val Ala Thr<br>                 160                      165                    170 | 713 | |
| cgg cag tca ttg gtg atc atg acg ttg ttt gcc gta ctg ttg gca acg<br>Arg Gln Ser Leu Val Ile Met Thr Leu Phe Ala Val Leu Leu Ala Thr<br>                     175                      180                    185 | 761 | |
| ctt att cat cat ttt ggc gaa caa att att gat ttc gtc gcg ggt gat<br>Leu Ile His His Phe Gly Glu Gln Ile Ile Asp Phe Val Ala Gly Asp<br>                       190                      195                  200 | 809 | |
| gcc acg aca gaa gtt aaa gca ctg gcg ttg act tat ctg gag ctg acg<br>Ala Thr Thr Glu Val Lys Ala Leu Ala Leu Thr Tyr Leu Glu Leu Thr<br>        205                      210                    215 | 857 | |
| gta ctc agt tat cca gca gct gcc atc act ctt att ggt agc ggg gca<br>Val Leu Ser Tyr Pro Ala Ala Ala Ile Thr Leu Ile Gly Ser Gly Ala<br>220                      225                    230                  235 | 905 | |
| ctt cgt ggt gca ggg aat acg aaa ata ccg cta ttg att aac ggt agc<br>Leu Arg Gly Ala Gly Asn Thr Lys Ile Pro Leu Leu Ile Asn Gly Ser<br>                     240                      245                    250 | 953 | |
| ctg aat att ctt aat att att att agc ggc ata ttg att tac ggc ctt<br>Leu Asn Ile Leu Asn Ile Ile Ile Ser Gly Ile Leu Ile Tyr Gly Leu<br>                     255                      260                    265 | 1001 | |
| ttc tcc tgg ccg gga ctg gga ttt gtc ggg gca ggg ctg ggt tta acc<br>Phe Ser Trp Pro Gly Leu Gly Phe Val Gly Ala Gly Leu Gly Leu Thr<br>        270                      275                    280 | 1049 | |
| att tct cgt tat att ggc gca gtt gca att ttg tgg gtg ctg gcg att<br>Ile Ser Arg Tyr Ile Gly Ala Val Ala Ile Leu Trp Val Leu Ala Ile<br>285                      290                    295 | 1097 | |
| ggt ttt aat cct gcg cta agg att tcg tta aag agc tat ttt aaa ccg<br>Gly Phe Asn Pro Ala Leu Arg Ile Ser Leu Lys Ser Tyr Phe Lys Pro<br>300                      305                    310                    315 | 1145 | |
| ctg aat ttt agc att atc tgg gaa gtc atg ggg att ggt att ccc gcg<br>Leu Asn Phe Ser Ile Ile Trp Glu Val Met Gly Ile Gly Ile Pro Ala<br>                     320                      325                    330 | 1193 | |
| agt gtc gaa tca gtg tta ttt acc agt ggt cgg tta tta acc caa atg<br>Ser Val Glu Ser Val Leu Phe Thr Ser Gly Arg Leu Leu Thr Gln Met<br>        335                      340                    345 | 1241 | |

```
ttc gtt gcc ggg atg ggg acc agt gtt att gcc gga aat ttt atc gcg    1289
Phe Val Ala Gly Met Gly Thr Ser Val Ile Ala Gly Asn Phe Ile Ala
            350                 355                 360 ttt tca att gcg gct ctt atc aac tta ccc gga agt gcg ctc ggc tct    1337
Phe Ser Ile Ala Ala Leu Ile Asn Leu Pro Gly Ser Ala Leu Gly Ser
365                 370                 375 gct tct acg atc att aca ggc cga agg ttg ggg gta ggg cag ata gcg    1385
Ala Ser Thr Ile Ile Thr Gly Arg Arg Leu Gly Val Gly Gln Ile Ala
380                 385                 390                 395 caa gca gag att cag ttg cgg cat gtg ttc tgg ctt tcc act ctt gga    1433
Gln Ala Glu Ile Gln Leu Arg His Val Phe Trp Leu Ser Thr Leu Gly
            400                 405                 410 tta acg gcc atc gcc tgg cta acg gct ccc ttt gcc ggg gtt atg gca    1481
Leu Thr Ala Ile Ala Trp Leu Thr Ala Pro Phe Ala Gly Val Met Ala
        415                 420                 425 tcg ttt tac acc cag gat cca cag gtt aaa cat gtc gtt gtg att ctg    1529
Ser Phe Tyr Thr Gln Asp Pro Gln Val Lys His Val Val Val Ile Leu
    430                 435                 440 att tgg cta aat gct tta ttt atg cct att tgg tcc gcc tca tgg gtg    1577
Ile Trp Leu Asn Ala Leu Phe Met Pro Ile Trp Ser Ala Ser Trp Val
445                 450                 455 cta ccc gct gga ttt aaa ggt gct cgt gat gcc cgt tac gcc atg tgg    1625
Leu Pro Ala Gly Phe Lys Gly Ala Arg Asp Ala Arg Tyr Ala Met Trp
460                 465                 470                 475 gtt tcg atg ttg agc atg tgg ggt tgt cgg gtt gta gtc ggt tat gtg    1673
Val Ser Met Leu Ser Met Trp Gly Cys Arg Val Val Val Gly Tyr Val
            480                 485                 490 ctg gga atc atg ctt ggc tgg ggt gtg gtt ggt gtc tgg atg gga atg    1721
Leu Gly Ile Met Leu Gly Trp Gly Val Val Gly Val Trp Met Gly Met
        495                 500                 505 ttt gcc gac tgg gct gtg cgg gcc gtg ctg ttt tac tgg cga atg gtt    1769
Phe Ala Asp Trp Ala Val Arg Ala Val Leu Phe Tyr Trp Arg Met Val
    510                 515                 520 act gga cgt tgg cta tgg aaa tac cct cga ccc gag ccg caa aag tgt    1817
Thr Gly Arg Trp Leu Trp Lys Tyr Pro Arg Pro Glu Pro Gln Lys Cys
525                 530                 535 gaa aaa aag cca gtt gtg tcg gaa taaacgacaa aatgcagatt atttcagcaa    1871
Glu Lys Lys Pro Val Val Ser Glu
540                 545 acgatttcaa atttaaaaaa caggctttga cattgtgggt gggcatcgct aatattcgcc    1931
tcgttctcac gat                                                      1944

<210> SEQ ID NO 6
<211> LENGTH: 396
<212> TYPE: PRT
<213> ORGANISM: Escherichia coli

<400> SEQUENCE: 6

Met Thr Thr Arg Gln His Ser Ser Phe Ala Ile Val Phe Ile Leu Gly
1               5                   10                  15

Leu Leu Ala Met Leu Met Pro Leu Ser Ile Asp Met Tyr Leu Pro Ala
            20                  25                  30

Leu Pro Val Ile Ser Ala Gln Phe Gly Val Pro Ala Gly Ser Thr Gln
        35                  40                  45

Met Thr Leu Ser Thr Tyr Ile Leu Gly Phe Ala Leu Gly Gln Leu Ile
    50                  55                  60

Tyr Gly Pro Met Ala Asp Ser Phe Gly Arg Lys Pro Val Val Leu Gly
65                  70                  75                  80
```

```
Gly Thr Leu Val Phe Ala Ala Ala Val Ala Cys Ala Leu Ala Asn
                 85                  90                  95

Thr Ile Asp Gln Leu Ile Val Met Arg Phe Phe His Gly Leu Ala Ala
            100                 105                 110

Ala Ala Ala Ser Val Val Ile Asn Ala Leu Met Arg Asp Ile Tyr Pro
            115                 120                 125

Lys Glu Glu Phe Ser Arg Met Met Ser Phe Val Met Leu Val Thr Thr
        130                 135                 140

Ile Ala Pro Leu Met Ala Pro Ile Val Gly Gly Trp Val Leu Val Trp
145                 150                 155                 160

Leu Ser Trp His Tyr Ile Phe Trp Ile Leu Ala Leu Ala Ala Ile Leu
                165                 170                 175

Ala Ser Ala Met Ile Phe Phe Leu Ile Lys Glu Thr Leu Pro Pro Glu
            180                 185                 190

Arg Arg Gln Pro Phe His Ile Arg Thr Thr Ile Gly Asn Phe Ala Ala
        195                 200                 205

Leu Phe Arg His Lys Arg Val Leu Ser Tyr Met Leu Ala Ser Gly Phe
210                 215                 220

Ser Phe Ala Gly Met Phe Ser Phe Leu Ser Ala Gly Pro Phe Val Tyr
225                 230                 235                 240

Ile Glu Ile Asn His Val Ala Pro Glu Asn Phe Gly Tyr Tyr Phe Ala
                245                 250                 255

Leu Asn Ile Val Phe Leu Phe Val Met Thr Ile Phe Asn Ser Arg Phe
            260                 265                 270

Val Arg Arg Ile Gly Ala Leu Asn Met Phe Arg Ser Gly Leu Trp Ile
        275                 280                 285

Gln Phe Ile Met Ala Ala Trp Met Val Ile Ser Ala Leu Leu Gly Leu
290                 295                 300

Gly Phe Trp Ser Leu Val Val Gly Val Ala Phe Val Gly Cys Val
305                 310                 315                 320

Ser Met Val Ser Ser Asn Ala Met Ala Val Ile Leu Asp Glu Phe Pro
                325                 330                 335

His Met Ala Gly Thr Ala Ser Ser Leu Ala Gly Thr Phe Arg Phe Gly
            340                 345                 350

Ile Gly Ala Ile Val Gly Ala Leu Leu Ser Leu Ala Thr Phe Asn Ser
        355                 360                 365

Ala Trp Pro Met Ile Trp Ser Ile Ala Phe Cys Ala Thr Ser Ser Ile
370                 375                 380

Leu Phe Cys Leu Tyr Ala Ser Arg Pro Lys Lys Arg
385                 390                 395

<210> SEQ ID NO 7
<211> LENGTH: 457
<212> TYPE: PRT
<213> ORGANISM: Escherichia coli

<400> SEQUENCE: 7

Met Gln Lys Tyr Ile Ser Glu Ala Arg Leu Leu Leu Ala Leu Ala Ile
1               5                   10                  15

Pro Val Ile Leu Ala Gln Ile Ala Gln Thr Ala Met Gly Phe Val Asp
            20                  25                  30

Thr Val Met Ala Gly Gly Tyr Ser Ala Thr Asp Met Ala Ala Val Ala
        35                  40                  45

Ile Gly Thr Ser Ile Trp Leu Pro Ala Ile Leu Phe Gly His Gly Leu
    50                  55                  60
```

```
Leu Leu Ala Leu Thr Pro Val Ile Ala Gln Leu Asn Gly Ser Gly Arg
 65                  70                  75                  80

Arg Glu Arg Ile Ala His Gln Val Arg Gln Gly Phe Trp Leu Ala Gly
                 85                  90                  95

Phe Val Ser Val Leu Ile Met Leu Val Leu Trp Asn Ala Gly Tyr Ile
            100                 105                 110

Ile Arg Ser Met Glu Asn Ile Asp Pro Ala Leu Ala Asp Lys Ala Val
        115                 120                 125

Gly Tyr Leu Arg Ala Leu Leu Trp Gly Ala Pro Gly Tyr Leu Phe Phe
130                 135                 140

Gln Val Ala Arg Asn Gln Cys Glu Gly Leu Ala Lys Thr Lys Pro Gly
145                 150                 155                 160

Met Val Met Gly Phe Ile Gly Leu Leu Val Asn Ile Pro Val Asn Tyr
                165                 170                 175

Ile Phe Ile Tyr Gly His Phe Gly Met Pro Glu Leu Gly Gly Val Gly
            180                 185                 190

Cys Gly Val Ala Thr Ala Ala Val Tyr Trp Val Met Phe Leu Ala Met
        195                 200                 205

Val Ser Tyr Ile Lys Arg Ala Arg Ser Met Arg Asp Ile Arg Asn Glu
210                 215                 220

Lys Gly Thr Ala Lys Pro Asp Pro Ala Val Met Lys Arg Leu Ile Gln
225                 230                 235                 240

Leu Gly Leu Pro Ile Ala Leu Ala Leu Phe Phe Glu Val Thr Leu Phe
                245                 250                 255

Ala Val Val Ala Leu Leu Val Ser Pro Leu Gly Ile Val Asp Val Ala
            260                 265                 270

Gly His Gln Ile Ala Leu Asn Phe Ser Ser Leu Met Phe Val Leu Pro
        275                 280                 285

Met Ser Leu Ala Ala Ala Val Thr Ile Arg Val Gly Tyr Arg Leu Gly
290                 295                 300

Gln Gly Ser Thr Leu Asp Ala Gln Thr Ala Ala Arg Thr Gly Leu Met
305                 310                 315                 320

Val Gly Val Cys Met Ala Thr Leu Thr Ala Ile Phe Thr Val Ser Leu
                325                 330                 335

Arg Glu Gln Ile Ala Leu Leu Tyr Asn Asp Asn Pro Glu Val Val Thr
            340                 345                 350

Leu Ala Ala His Leu Met Leu Leu Ala Ala Val Tyr Gln Ile Ser Asp
        355                 360                 365

Ser Ile Gln Val Ile Gly Ser Gly Ile Leu Arg Gly Tyr Lys Asp Thr
370                 375                 380

Arg Ser Ile Phe Tyr Ile Thr Phe Thr Ala Tyr Trp Val Leu Gly Leu
385                 390                 395                 400

Pro Ser Gly Tyr Ile Leu Ala Leu Thr Asp Leu Val Val Glu Pro Met
                405                 410                 415

Gly Pro Ala Gly Phe Trp Ile Gly Phe Ile Ile Gly Leu Thr Ser Ala
            420                 425                 430

Ala Ile Met Met Met Leu Arg Met Arg Phe Leu Gln Arg Leu Pro Ser
        435                 440                 445

Ala Ile Ile Leu Gln Arg Ala Ser Arg
450                 455

<210> SEQ ID NO 8
<211> LENGTH: 395
<212> TYPE: PRT
<213> ORGANISM: Escherichia coli
```

<400> SEQUENCE: 8

Met Asn Leu Ser Leu Arg Arg Ser Thr Ser Ala Leu Ala Ser Ser
1               5                   10                  15

Leu Leu Leu Thr Ile Gly Arg Gly Ala Thr Leu Pro Phe Met Thr Ile
            20                  25                  30

Tyr Leu Ser Arg Gln Tyr Ser Leu Ser Val Asp Leu Ile Gly Tyr Ala
            35                  40                  45

Met Thr Ile Ala Leu Thr Ile Gly Val Val Phe Ser Leu Gly Phe Gly
    50                  55                  60

Ile Leu Ala Asp Lys Phe Asp Lys Lys Arg Tyr Met Leu Leu Ala Ile
65                  70                  75                  80

Thr Ala Phe Ala Ser Gly Phe Ile Ala Ile Thr Leu Val Asn Asn Val
                85                  90                  95

Thr Leu Val Val Leu Phe Phe Ala Leu Ile Asn Cys Ala Tyr Ser Val
                100                 105                 110

Phe Ala Thr Val Leu Lys Ala Trp Phe Ala Asp Asn Leu Ser Ser Thr
                115                 120                 125

Ser Lys Thr Lys Ile Phe Ser Ile Asn Tyr Thr Met Leu Asn Ile Gly
    130                 135                 140

Trp Thr Ile Gly Pro Pro Leu Gly Thr Leu Leu Val Met Gln Ser Ile
145                 150                 155                 160

Asn Leu Pro Phe Trp Leu Ala Ala Ile Cys Ser Ala Phe Pro Met Leu
                165                 170                 175

Phe Ile Gln Ile Trp Val Lys Arg Ser Glu Lys Ile Ile Ala Thr Glu
                180                 185                 190

Thr Gly Ser Val Trp Ser Pro Lys Val Leu Leu Gln Asp Lys Ala Leu
                195                 200                 205

Leu Trp Phe Thr Cys Ser Gly Phe Leu Ala Ser Phe Val Ser Gly Ala
                210                 215                 220

Phe Ala Ser Cys Ile Ser Gln Tyr Val Met Val Ile Ala Asp Gly Asp
225                 230                 235                 240

Phe Ala Glu Lys Val Val Ala Val Val Leu Pro Val Asn Ala Ala Met
                245                 250                 255

Val Val Thr Leu Gln Tyr Ser Val Gly Arg Arg Leu Asn Pro Ala Asn
                260                 265                 270

Ile Arg Ala Leu Met Thr Ala Gly Thr Leu Cys Phe Val Ile Gly Leu
                275                 280                 285

Val Gly Phe Ile Phe Ser Gly Asn Ser Leu Leu Trp Gly Met Ser
                290                 295                 300

Ala Ala Val Phe Thr Val Gly Glu Ile Ile Tyr Ala Pro Gly Glu Tyr
305                 310                 315                 320

Met Leu Ile Asp His Ile Ala Pro Pro Glu Met Lys Ala Ser Tyr Phe
                325                 330                 335

Ser Ala Gln Ser Leu Gly Trp Leu Gly Ala Ala Ile Asn Pro Leu Val
                340                 345                 350

Ser Gly Val Val Leu Thr Ser Leu Pro Pro Ser Ser Leu Phe Val Ile
                355                 360                 365

Leu Ala Leu Val Ile Ile Ala Ala Trp Val Leu Met Leu Lys Gly Ile
                370                 375                 380

Arg Ala Arg Pro Trp Gly Gln Pro Ala Leu Cys
385                 390                 395

<210> SEQ ID NO 9

```
<211> LENGTH: 394
<212> TYPE: PRT
<213> ORGANISM: Escherichia coli

<400> SEQUENCE: 9

Met Lys Arg Gln Arg Asn Val Asn Leu Leu Met Leu Val Leu Leu
1               5                   10                  15

Val Ala Val Gly Gln Met Ala Gln Thr Ile Tyr Ile Pro Ala Ile
                20                  25                  30

Asp Met Ala Arg Asp Leu Asn Val Arg Glu Gly Ala Val Gln Ser Val
                35                  40                  45

Met Gly Ala Tyr Leu Leu Thr Tyr Gly Val Ser Gln Leu Phe Tyr Gly
50                  55                  60

Pro Ile Ser Asp Arg Val Gly Arg Arg Pro Val Ile Leu Val Gly Met
65                  70                  75                  80

Ser Ile Phe Met Leu Ala Thr Leu Val Ala Val Thr Thr Ser Ser Leu
                85                  90                  95

Thr Val Leu Ile Ala Ala Ser Ala Met Gln Gly Met Gly Thr Gly Val
                100                 105                 110

Gly Gly Val Met Ala Arg Thr Leu Pro Arg Asp Leu Tyr Glu Arg Thr
                115                 120                 125

Gln Leu Arg His Ala Asn Ser Leu Leu Asn Met Gly Ile Leu Val Ser
130                 135                 140

Pro Leu Leu Ala Pro Leu Ile Gly Gly Leu Leu Asp Thr Met Trp Asn
145                 150                 155                 160

Trp Arg Ala Cys Tyr Leu Phe Leu Leu Val Leu Cys Ala Gly Val Thr
                165                 170                 175

Phe Ser Met Ala Arg Trp Met Pro Glu Thr Arg Pro Val Asp Ala Pro
                180                 185                 190

Arg Thr Arg Leu Leu Thr Ser Tyr Lys Thr Leu Phe Gly Asn Ser Gly
                195                 200                 205

Phe Asn Cys Tyr Leu Leu Met Leu Ile Gly Gly Leu Ala Gly Ile Ala
210                 215                 220

Ala Phe Glu Ala Cys Ser Gly Val Leu Met Gly Ala Val Leu Gly Leu
225                 230                 235                 240

Ser Ser Met Thr Val Ser Ile Leu Phe Ile Leu Pro Ile Pro Ala Ala
                245                 250                 255

Phe Phe Gly Ala Trp Phe Ala Gly Arg Pro Asn Lys Arg Phe Ser Thr
                260                 265                 270

Leu Met Trp Gln Ser Val Ile Cys Cys Leu Leu Ala Gly Leu Leu Met
                275                 280                 285

Trp Ile Pro Asp Trp Phe Gly Val Met Asn Val Trp Thr Leu Leu Val
                290                 295                 300

Pro Ala Ala Leu Phe Phe Phe Gly Ala Gly Met Leu Phe Pro Leu Ala
305                 310                 315                 320

Thr Ser Gly Ala Met Glu Pro Phe Pro Phe Leu Ala Gly Thr Ala Gly
                325                 330                 335

Ala Leu Val Gly Gly Leu Gln Asn Ile Gly Ser Gly Val Leu Ala Ser
                340                 345                 350

Leu Ser Ala Met Leu Pro Gln Thr Gly Gln Gly Ser Leu Gly Leu Leu
                355                 360                 365

Met Thr Leu Met Gly Leu Leu Ile Val Leu Cys Trp Leu Pro Leu Ala
                370                 375                 380

Thr Arg Met Ser His Gln Gly Gln Pro Val
385                 390
```

<210> SEQ ID NO 10
<211> LENGTH: 547
<212> TYPE: PRT
<213> ORGANISM: Escherichia coli

<400> SEQUENCE: 10

```
Met Leu Arg His Ile Leu Thr Ala Lys Asn Leu Leu Ser Asn Pro Ile
1               5                   10                  15

Phe Lys Phe Pro Asn Cys Leu Pro Phe Leu Ser Thr Val Cys Cys Ile
            20                  25                  30

Cys Arg Gln Phe Val Gly Glu Asn Leu Cys Ser Phe Ala Asp Ser Pro
        35                  40                  45

Ser Leu Phe Glu Met Trp Phe His Phe Leu Gln Leu Arg Ser Ala Leu
    50                  55                  60

Asn Ile Ser Ser Ala Leu Arg Gln Val Val His Gly Thr Arg Trp His
65                  70                  75                  80

Ala Lys Arg Lys Ser Tyr Lys Val Leu Phe Trp Arg Glu Ile Thr Pro
                85                  90                  95

Leu Ala Val Pro Ile Phe Met Glu Asn Ala Cys Val Leu Leu Met Gly
            100                 105                 110

Val Leu Ser Thr Phe Leu Val Ser Trp Leu Gly Lys Asp Ala Met Ala
        115                 120                 125

Gly Val Gly Leu Ala Asp Ser Phe Asn Met Val Ile Met Ala Phe Phe
    130                 135                 140

Ala Ala Ile Asp Leu Gly Thr Thr Val Val Ala Phe Ser Leu Gly
145                 150                 155                 160

Lys Arg Asp Arg Arg Ala Arg Val Ala Thr Arg Gln Ser Leu Val
                165                 170                 175

Ile Met Thr Leu Phe Ala Val Leu Leu Ala Thr Leu Ile His His Phe
            180                 185                 190

Gly Glu Gln Ile Ile Asp Phe Val Ala Gly Asp Ala Thr Glu Val
    195                 200                 205

Lys Ala Leu Ala Leu Thr Tyr Leu Glu Leu Thr Val Leu Ser Tyr Pro
210                 215                 220

Ala Ala Ala Ile Thr Leu Ile Gly Ser Gly Ala Leu Arg Gly Ala Gly
225                 230                 235                 240

Asn Thr Lys Ile Pro Leu Leu Ile Asn Gly Ser Leu Asn Ile Leu Asn
                245                 250                 255

Ile Ile Ile Ser Gly Ile Leu Ile Tyr Gly Leu Phe Ser Trp Pro Gly
            260                 265                 270

Leu Gly Phe Val Gly Ala Gly Leu Gly Leu Thr Ile Ser Arg Tyr Ile
    275                 280                 285

Gly Ala Val Ala Ile Leu Trp Val Leu Ala Ile Gly Phe Asn Pro Ala
290                 295                 300

Leu Arg Ile Ser Leu Lys Ser Tyr Phe Lys Pro Leu Asn Phe Ser Ile
305                 310                 315                 320

Ile Trp Glu Val Met Gly Ile Gly Ile Pro Ala Ser Val Glu Ser Val
                325                 330                 335

Leu Phe Thr Ser Gly Arg Leu Leu Thr Gln Met Phe Val Ala Gly Met
            340                 345                 350

Gly Thr Ser Val Ile Ala Gly Asn Phe Ile Ala Phe Ser Ile Ala Ala
    355                 360                 365

Leu Ile Asn Leu Pro Gly Ser Ala Leu Gly Ser Ala Ser Thr Ile Ile
370                 375                 380
```

```
Thr Gly Arg Arg Leu Gly Val Gly Gln Ile Ala Gln Ala Glu Ile Gln
385                 390                 395                 400

Leu Arg His Val Phe Trp Leu Ser Thr Leu Gly Leu Thr Ala Ile Ala
            405                 410                 415

Trp Leu Thr Ala Pro Phe Ala Gly Val Met Ala Ser Phe Tyr Thr Gln
        420                 425                 430

Asp Pro Gln Val Lys His Val Val Ile Leu Ile Trp Leu Asn Ala
        435                 440                 445

Leu Phe Met Pro Ile Trp Ser Ala Ser Trp Val Leu Pro Ala Gly Phe
    450                 455                 460

Lys Gly Ala Arg Asp Ala Arg Tyr Ala Met Trp Val Ser Met Leu Ser
465                 470                 475                 480

Met Trp Gly Cys Arg Val Val Gly Tyr Val Leu Gly Ile Met Leu
            485                 490                 495

Gly Trp Gly Val Val Gly Val Trp Met Gly Met Phe Ala Asp Trp Ala
        500                 505                 510

Val Arg Ala Val Leu Phe Tyr Trp Arg Met Val Thr Gly Arg Trp Leu
        515                 520                 525

Trp Lys Tyr Pro Arg Pro Glu Pro Gln Lys Cys Glu Lys Lys Pro Val
        530                 535                 540

Val Ser Glu
545

<210> SEQ ID NO 11
<211> LENGTH: 472
<212> TYPE: PRT
<213> ORGANISM: Bacillus subtilis 168

<400> SEQUENCE: 11

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asn Lys Pro Glu Glu Glu Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205
```

Lys Ser Ile Asn Val Pro Lys Ala Val Thr Phe Glu Ala Pro Phe Ile
                210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
                260                 265                 270

Glu Thr Ser His Ile Thr Pro Ser Ile Leu Asp Glu Ala Lys Lys
                275                 280                 285

Lys Ile Val Glu Ala Ala Lys Lys Ala Asn Glu Gly Leu Gly Leu Gln
                290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
                340                 345                 350

Val Leu Cys Phe Gly Lys Asp Ala Asp Leu Pro Asp Gly Leu Leu Asp
                355                 360                 365

Gln Glu Pro Tyr Tyr Val Ala Asp Cys His Leu Tyr Pro Gln His Phe
                370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
                435                 440                 445

Gln Asp Val Ala Glu Ser Ile Arg Gln Ile Gln Gln His Ala Lys Leu
450                 455                 460

Thr Ala Lys Tyr Val Leu Pro Val
465                 470

<210> SEQ ID NO 12
<211> LENGTH: 472
<212> TYPE: PRT
<213> ORGANISM: Bacillus subtilis ATCC6633

<400> SEQUENCE: 12

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
                35                  40                  45

Glu Lys Tyr Ser Val Ala Val Ile Lys Asp Lys Asp Tyr Phe Gln Ser
                50                  55                  60

Leu Ala Asp Phe Glu His Pro Asp Ser Ile Tyr Trp Ala His Glu Asp
65                  70                  75                  80

His Asp Lys Pro Glu Glu Val Val Glu Gln Ile Val Lys Val Ala
                85                  90                  95

Gln Met Phe Glu Ala Asp Ala Ile Thr Thr Asn Asn Glu Leu Phe Ile
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
        130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Ile Gly Thr Pro Leu Ile
                165                 170                 175

Leu Lys Pro Thr Tyr Leu Ala Ser Ser Ile Gly Val Thr Leu Ile Thr
                180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
        210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
                260                 265                 270

Glu Thr Ser His Ile Thr Pro Ser Ile Leu Asp Glu Glu Ala Lys Lys
            275                 280                 285

Lys Ile Val Glu Ala Ala Lys Lys Ala Asn Glu Gly Leu Gly Leu Gln
        290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
                340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys His Leu Tyr Pro Gln His Phe
        370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
        450                 455                 460

Thr Ala Lys Tyr Val Leu Pro Val
465                 470

<210> SEQ ID NO 13
<211> LENGTH: 472
<212> TYPE: PRT
<213> ORGANISM: Bacillus subtilis IAM1213

<400> SEQUENCE: 13

Met Glu Arg Lys Thr Val Leu Val Ile Ala Asp Leu Gly Gly Cys Pro
1               5                   10                  15

```
Pro His Met Phe Tyr Lys Ser Ala Ala Glu Lys Tyr Asn Leu Val Ser
         20                  25                  30

Phe Ile Pro Arg Pro Phe Ala Ile Thr Ala Ser His Ala Ala Leu Ile
             35                  40                  45

Glu Lys Tyr Ser Val Ala Val Ile Lys Asp Lys Asp Tyr Phe Lys Ser
 50                  55                  60

Leu Ala Asp Phe Glu His Pro Asp Ser Ile Tyr Trp Ala His Glu Asp
 65              70                  75                  80

His Asn Lys Pro Glu Glu Val Val Glu Gln Ile Val Lys Val Ala
                 85                  90                  95

Glu Met Phe Gly Ala Asp Ala Ile Thr Thr Asn Asn Glu Leu Phe Ile
             100                 105                 110

Ala Pro Met Ala Lys Ala Cys Glu Arg Leu Gly Leu Arg Gly Ala Gly
             115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                 165                 170                 175

Leu Lys Pro Thr Tyr Leu Ala Ser Ser Ile Gly Val Thr Leu Ile Thr
             180                 185                 190

Asp Thr Glu Thr Ala Glu Asp Glu Phe Asn Arg Val Asn Asp Tyr Leu
         195                 200                 205

Lys Ser Ile Asn Val Pro Lys Ala Val Thr Phe Glu Ala Pro Phe Ile
210                 215                 220

Ala Glu Glu Phe Leu Gln Gly Tyr Gly Asp Trp Tyr Gln Thr Glu
225                 230                 235                 240

Gly Tyr Ser Asp Tyr Ile Ser Ile Glu Gly Ile Met Ala Asp Gly Glu
             245                 250                 255

Tyr Phe Pro Ile Ala Ile His Asp Lys Thr Pro Gln Ile Gly Phe Thr
             260                 265                 270

Glu Thr Ser His Ile Thr Pro Ser Ile Leu Asp Glu Glu Ala Lys Lys
         275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
             325                 330                 335

Asn Ile Lys Lys Val Phe Gly Leu Asp Met Ala Gln Leu Leu Leu Asp
             340                 345                 350

Val Leu Cys Phe Gly Lys Asp Ala Asp Leu Pro Asp Gly Leu Leu Asp
             355                 360                 365

Gln Glu Pro Tyr Tyr Val Ala Asp Cys His Leu Tyr Pro Gln His Phe
         370                 375                 380

Lys Gln Asn Gly Gln Ile Pro Glu Thr Ala Glu Asp Leu Val Ile Glu
385                 390                 395                 400

Ala Ile Asp Leu Pro Asp Gly Leu Leu Lys Gly Asp Thr Glu Ile Val
                 405                 410                 415

Ser Phe Ser Ala Ala Pro Gly Thr Ser Val Asp Leu Thr Leu Phe
             420                 425                 430

Glu Ala Phe Asn Ser Ile Ala Ala Phe Glu Leu Lys Gly Ser Asn Ser
```

```
                    435                 440                 445
Gln Asp Val Ala Glu Ser Ile Arg Gln Ile Gln His Ala Lys Leu
        450                 455                 460

Thr Ala Lys Tyr Val Leu Pro Val
465                 470

<210> SEQ ID NO 14
<211> LENGTH: 472
<212> TYPE: PRT
<213> ORGANISM: Bacillus subtilis IAM1107

<400> SEQUENCE: 14

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Val Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
        130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
    290                 295                 300

Asn Cys Ala Thr His Thr Glu Val Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
```

-continued

```
                        340                 345                 350
Val Leu Cys Phe Gly Lys Asp Ala Asp Leu Pro Asp Gly Leu Leu Asp
                355                 360                 365

Gln Glu Pro Tyr Tyr Val Ala Asp Cys His Leu Tyr Pro Gln His Phe
        370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Phe
                405                 410                 415

Ser Phe Ser Ala Ala Pro Gly Thr Ser Val Asp Leu Thr Leu Phe
        420                 425                 430

Glu Ala Phe Asn Ser Ile Ala Ala Phe Glu Leu Lys Gly Ser Asn Ser
                435                 440                 445

Gln Asp Val Ala Glu Ser Ile Arg Gln Ile Gln Gln His Ala Lys Leu
        450                 455                 460

Thr Ala Lys Tyr Val Leu Pro Val
465                 470

<210> SEQ ID NO 15
<211> LENGTH: 472
<212> TYPE: PRT
<213> ORGANISM: Bacillus subtilis IAM1214

<400> SEQUENCE: 15

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Gln Ser
        50                  55                  60

Leu Ala Asp Phe Glu His Pro Asp Ser Ile Tyr Trp Ala His Glu Asp
65                  70                  75                  80

His Asp Lys Pro Glu Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
```

```
              245                 250                 255
Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
            275                 280                 285

Lys Ile Val Glu Ala Ala Lys Lys Ala Asn Glu Gly Leu Gly Leu Gln
            290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
                340                 345                 350

Val Leu Cys Phe Gly Lys Asp Ala Asp Leu Pro Asp Gly Leu Leu Asp
                355                 360                 365

Gln Glu Pro Tyr Tyr Val Ala Asp Cys His Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Pro Gly Thr Ser Val Asp Leu Thr Leu Phe
                420                 425                 430

Glu Ala Phe Asn Ser Ile Ala Ala Phe Glu Leu Lys Gly Ser Asn Ser
                435                 440                 445

Gln Asp Val Ala Glu Ser Ile Arg Gln Ile Gln Gln His Ala Lys Leu
            450                 455                 460

Thr Ala Lys Tyr Val Leu Pro Val
465                 470

<210> SEQ ID NO 16
<211> LENGTH: 472
<212> TYPE: PRT
<213> ORGANISM: Bacillus subtilis ATCC21555

<400> SEQUENCE: 16

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Ile Ala Val Ile Lys Asp Lys Asp Tyr Phe Lys Ser
    50                  55                  60

Leu Ala Asp Phe Glu His Pro Asp Ser Ile Tyr Trp Ala His Glu Asp
65                  70                  75                  80

His Asp Lys Pro Glu Glu Glu Val Glu Glu Ile Val Lys Val Ala
                85                  90                  95

Asp Met Phe Gly Val Asp Ala Ile Thr Thr Asn Asn Glu Leu Phe Ile
                100                 105                 110

Ala Pro Met Ala Lys Ala Cys Lys Arg Leu Gly Leu Arg Gly Ala Gly
                115                 120                 125

Val Gln Ala Ala Glu Asn Ala Arg Asp Lys Asn Lys Met Arg Ala Ala
            130                 135                 140

Phe Asn Arg Ala Gly Val Lys Ser Ile Lys Asn Lys Arg Val Thr Thr
```

```
                145                 150                 155                 160
Leu Glu Asp Phe Arg Ala Ala Leu Gln Glu Ile Gly Thr Pro Leu Ile
                165                 170                 175

Leu Lys Pro Thr Tyr Leu Ala Ser Ser Ile Gly Val Thr Leu Ile Lys
            180                 185                 190

Glu Met Glu Thr Ala Glu Ala Glu Phe Asn Arg Val Asn Glu Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Asp Asp Trp Tyr Glu Thr Ser
225                 230                 235                 240

Gly Tyr Ser Asp Tyr Ile Ser Ile Glu Gly Ile Met Ala Asp Gly Glu
                245                 250                 255

Tyr Phe Pro Val Ala Ile His Asp Lys Thr Pro Gln Ile Gly Phe Thr
            260                 265                 270

Glu Thr Ala His Ile Thr Pro Ser Ile Leu Asp Asp Ala Lys Arg
        275                 280                 285

Lys Ile Val Glu Ala Ala Lys Lys Ala Asn Glu Gly Leu Gly Leu Glu
    290                 295                 300

Asn Cys Ala Thr His Thr Glu Ile Lys Leu Met Lys Asn Arg Glu Ala
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Val Asp Met Ala Gln Leu Leu Leu Asp
            340                 345                 350

Val Leu Cys Tyr Gly Lys Glu Ala Asp Leu Pro Lys Gly Leu Leu Glu
        355                 360                 365

Gln Glu Pro Cys Tyr Val Ala Asp Cys His Leu Tyr Pro Gln His Phe
    370                 375                 380

Lys Glu Asn Gly Gln Leu Pro Glu Thr Val Val Asp Phe Val Ile Glu
385                 390                 395                 400

Ser Ile Glu Ile Pro Asp Gly Val Leu Lys Gly Asp Thr Glu Leu Val
                405                 410                 415

Ser Phe Ser Ala Ala Glu Ala Gly Thr Ser Val Asp Leu Arg Leu Phe
            420                 425                 430

Glu Ala Phe Asn Ser Ile Ala Ala Phe Glu Leu Lys Gly Ser Asn Ser
        435                 440                 445

Asn Asp Val Ala Glu Ser Ile Lys Gln Ile Gln Gln Gln Ala Lys Leu
    450                 455                 460

Thr Ala Lys Tyr Ala Leu Ser Val
465                 470

<210> SEQ ID NO 17
<211> LENGTH: 472
<212> TYPE: PRT
<213> ORGANISM: Bacillus amyloliquefaciens IFO3022

<400> SEQUENCE: 17

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
```

```
                50                   55                   60
Leu Ala Asp Phe Glu His Pro Asp Ser Ile Tyr Trp Ala His Glu Asp
65                   70                   75                   80

His Asp Lys Pro Glu Glu Val Val Glu Ile Val Lys Val Ala
                    85                   90                   95

Gly Met Phe Ala Val Asp Ala Ile Thr Thr Asn Asn Glu Leu Phe Ile
                    100                  105                  110

Ala Pro Met Ala Lys Ala Cys Glu Arg Leu Gly Leu Arg Gly Ala Gly
                    115                  120                  125

Val Gln Ala Ala Glu Asn Ala Arg Asp Lys Asn Lys Met Arg Ala Ala
                    130                  135                  140

Phe Asn Arg Ala Gly Val Lys Ser Ile Lys Asn Arg Val Thr Thr
145                  150                  155                  160

Leu Glu Asp Phe Arg Ala Ala Leu Gln Glu Ile Gly Thr Pro Leu Ile
                    165                  170                  175

Leu Lys Pro Thr Tyr Leu Ala Ser Ser Ile Gly Val Thr Leu Ile Lys
                    180                  185                  190

Glu Arg Glu Thr Ala Glu Ala Glu Phe Asn Arg Val Asn Glu Tyr Leu
                    195                  200                  205

Lys Ser Ile Asn Val Pro Lys Ala Val Thr Phe Glu Ala Pro Phe Ile
210                  215                  220

Ala Glu Glu Phe Leu Gln Gly Tyr Asp Asp Trp Tyr Glu Thr Ser
225                  230                  235                  240

Gly Tyr Ser Asp Tyr Ile Ser Ile Glu Gly Ile Met Ala Asp Gly Glu
                    245                  250                  255

Tyr Phe Pro Val Ala Ile His Asp Lys Thr Pro Gln Ile Gly Phe Thr
                    260                  265                  270

Glu Thr Ser His Ile Thr Pro Ser Ile Leu Asp Asp Ala Lys Arg
                    275                  280                  285

Lys Ile Val Glu Ala Ala Lys Lys Ala Asn Glu Gly Leu Gly Leu Glu
                    290                  295                  300

Asn Cys Ala Thr His Thr Glu Ile Lys Leu Met Lys Asn Arg Glu Ala
305                  310                  315                  320

Gly Leu Ile Glu Ser Ala Ala Arg Phe Ala Gly Trp Asn Met Ile Pro
                    325                  330                  335

Asn Ile Lys Lys Val Phe Gly Val Asp Met Ala Gln Leu Leu Leu Asp
                    340                  345                  350

Val Leu Cys Phe Gly Lys Glu Ala Asp Leu Pro Lys Gly Leu Leu Glu
                    355                  360                  365

Gln Glu Pro Cys Tyr Val Ala Asp Cys His Leu Tyr Pro Gln His Phe
370                  375                  380

Lys Glu Asn Gly Gln Leu Pro Glu Thr Ala Val Asp Phe Val Ile Glu
385                  390                  395                  400

Ser Ile Asp Ile Pro Asp Gly Val Leu Lys Gly Asp Thr Glu Ile Val
                    405                  410                  415

Ser Phe Ser Ala Ala Glu Ala Gly Thr Ser Val Asp Leu Arg Leu Phe
                    420                  425                  430

Glu Ala Phe Asn Ser Ile Ala Ala Phe Glu Leu Lys Gly Ser Asn Ser
                    435                  440                  445

Gly Asp Val Ala Glu Ser Ile Lys Gln Ile Gln Gln Ala Lys Leu
                    450                  455                  460

Thr Ala Lys Tyr Ala Leu Pro Val
465                  470
```

```
<210> SEQ ID NO 18
<211> LENGTH: 476
<212> TYPE: PRT
<213> ORGANISM: Bacillus pumilus NRRL B-12025

<400> SEQUENCE: 18
```

| | | | | | | | | | | | | | | | |
|---|---|---|---|---|---|---|---|---|---|---|---|---|---|---|---|
| Val | Leu | Ser | Leu | Ser | Lys | Lys | Thr | Val | Leu | Ile | Ala | Asp | Leu | Gly | |
| 1 | | | | 5 | | | | | 10 | | | | | 15 | |
| Gly | Cys | Pro | Pro | His | Met | Phe | Tyr | Glu | Ser | Val | Ala | Ala | Ser | Tyr | His |
| | | | 20 | | | | | 25 | | | | | 30 | | |
| Ile | Val | Ser | Tyr | Ile | Pro | Arg | Pro | Phe | Ala | Ile | Thr | Lys | Gly | His | Ala |
| | | 35 | | | | | 40 | | | | | 45 | | | |
| Glu | Leu | Ile | Glu | Lys | Tyr | Ser | Ile | Ala | Val | Ile | Lys | Asp | Arg | Asp | Tyr |
| | 50 | | | | | 55 | | | | | 60 | | | | |
| Phe | Glu | Thr | His | Pro | Ser | Phe | Glu | His | Pro | Asp | Ser | Ile | Tyr | Trp | Ala |
| 65 | | | | | 70 | | | | | 75 | | | | | 80 |
| His | Asp | Asp | Tyr | Pro | Lys | Ser | Glu | Glu | Val | Val | Glu | Asp | Phe | Ile | |
| | | | | 85 | | | | | 90 | | | | | 95 | |
| Arg | Val | Ala | Ser | Phe | Phe | Lys | Ala | Asp | Ala | Ile | Thr | Thr | Asn | Asn | Glu |
| | | | 100 | | | | | 105 | | | | | 110 | | |
| Leu | Phe | Ile | Ala | Pro | Met | Ala | Lys | Ala | Ala | Glu | Arg | Leu | Gly | Leu | Arg |
| | | 115 | | | | | 120 | | | | | 125 | | | |
| Gly | Ala | Gly | Val | Lys | Ala | Ala | Glu | Met | Ala | Arg | Asp | Lys | Ser | Gln | Met |
| | 130 | | | | | 135 | | | | | 140 | | | | |
| Arg | Ala | Ala | Phe | Asn | Ala | Ser | Gly | Val | Lys | Ala | Val | Lys | Thr | Gln | Pro |
| 145 | | | | | 150 | | | | | 155 | | | | | 160 |
| Val | Thr | Thr | Leu | Ser | Asp | Phe | Gln | Gln | Ala | Ile | Glu | Ser | Ile | Gly | Thr |
| | | | | 165 | | | | | 170 | | | | | 175 | |
| Pro | Leu | Ile | Leu | Lys | Pro | Thr | Tyr | Leu | Ala | Ser | Ser | Ile | Gly | Val | Thr |
| | | | 180 | | | | | 185 | | | | | 190 | | |
| Leu | Phe | His | Asp | Lys | Ala | Gly | Ser | Asp | Asp | Leu | Phe | Leu | Gln | Val | Gln |
| | | 195 | | | | | 200 | | | | | 205 | | | |
| Ser | Tyr | Leu | Glu | Thr | Ile | Pro | Val | Pro | Asp | Ala | Val | Thr | Tyr | Glu | Ala |
| | 210 | | | | | 215 | | | | | 220 | | | | |
| Pro | Phe | Val | Ala | Glu | Thr | Tyr | Leu | Glu | Gly | Ala | Tyr | Glu | Asp | Trp | Tyr |
| 225 | | | | | 230 | | | | | 235 | | | | | 240 |
| Glu | Asp | Glu | Gly | Tyr | Ala | Asp | Tyr | Val | Ser | Val | Glu | Gly | Leu | Val | Val |
| | | | | 245 | | | | | 250 | | | | | 255 | |
| Glu | Gly | Glu | Tyr | Leu | Pro | Phe | Val | Ile | His | Asp | Lys | Thr | Pro | Gln | Ile |
| | | | 260 | | | | | 265 | | | | | 270 | | |
| Gly | Phe | Thr | Glu | Thr | Ala | His | Ile | Thr | Pro | Thr | Ile | Leu | Asp | Asn | Glu |
| | | 275 | | | | | 280 | | | | | 285 | | | |
| Ala | Lys | Gln | Ile | Ile | Glu | Ala | Ala | Arg | Lys | Ala | Asn | Glu | Gly | Leu | |
| | 290 | | | | | 295 | | | | | 300 | | | | |
| Gly | Leu | Glu | His | Cys | Ala | Thr | His | Thr | Glu | Ile | Lys | Leu | Met | Lys | Asn |
| 305 | | | | | 310 | | | | | 315 | | | | | 320 |
| Arg | Glu | Thr | Gly | Leu | Ile | Glu | Ala | Ala | Arg | Phe | Ala | Gly | Trp | Asn | |
| | | | | 325 | | | | | 330 | | | | | 335 | |
| Met | Ile | Pro | Asn | Ile | Lys | Lys | Val | Phe | Gly | Val | Asp | Met | Ala | Lys | Leu |
| | | | 340 | | | | | 345 | | | | | 350 | | |
| Leu | Ile | Asp | Val | Leu | Val | Asp | Gly | Lys | Lys | Ala | Val | Leu | Pro | Lys | Gln |
| | | 355 | | | | | 360 | | | | | 365 | | | |
| Leu | Leu | Ser | Gly | His | Thr | Phe | Tyr | Val | Ala | Asp | Cys | His | Leu | Tyr | Pro |
| | 370 | | | | | 375 | | | | | 380 | | | | |

```
Gln His Phe Lys Glu Ser Gly Leu Ile Pro Pro Glu Ala Thr His Ile
385                 390                 395                 400

Thr Ile Asp His Val Ser Ile Pro Gln Glu Ala Phe Val Gly Asp Thr
                405                 410                 415

Ala Ile Val Ser Gln Ser Phe Pro Ala Lys Gly Thr Ile Val Asp Leu
            420                 425                 430

Glu Leu Phe Glu Ala Phe Asn Gly Ile Val Ser Leu Glu Leu Lys Gly
        435                 440                 445

Ser Ser Ser Gln Asp Val Ala Ala Ser Ile Arg Asn Ile Gln Lys Gln
    450                 455                 460

Ala Thr Ile Gln Leu Met Asp Glu Leu Val Lys Gly
465                 470                 475

<210> SEQ ID NO 19
<211> LENGTH: 93
<212> TYPE: PRT
<213> ORGANISM: Bacillus subtilis 168

<400> SEQUENCE: 19

Gly Ala Gly Val Gln Ala Ala Glu Asn Ala Arg Asp Lys Asn Lys Met
1               5                   10                  15

Arg Asp Ala Phe Asn Lys Ala Gly Val Lys Ser Ile Lys Asn Lys Arg
            20                  25                  30

Val Thr Thr Leu Glu Asp Phe Arg Ala Ala Leu Glu Glu Ile Gly Thr
        35                  40                  45

Pro Leu Ile Leu Lys Pro Thr Tyr Leu Ala Ser Ser Ile Gly Val Thr
    50                  55                  60

Leu Ile Thr Asp Thr Glu Thr Ala Glu Asp Glu Phe Asn Arg Val Asn
65                  70                  75                  80

Asp Tyr Leu Lys Ser Ile Asn Val Pro Lys Ala Val Thr
                85                  90

<210> SEQ ID NO 20
<211> LENGTH: 1416
<212> TYPE: DNA
<213> ORGANISM: Bacillus subtilis 168

<400> SEQUENCE: 20 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
            20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
        35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
    50                  55                  60 tta gct gat ttt gaa cac cct gat tcc att tat tgg gcg cat gaa gat     240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
            100                 105                 110
```

```
gct ccg atg gcg aaa gcc tgt gaa cgt ctg ggc ttg aga ggt gcc ggc       384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct       432
Val Gln Ala Ala Glu Asn Ala Arg Asp Lys Asn Lys Met Arg Asp Ala
130                 135                 140 ttt aat aag gcc gga gtc aaa tcg atc aaa aac aaa cga gtc aca act       480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc       528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg       576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg       624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc       672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa       720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag       768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca       816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag       864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt gga ctg caa       912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg       960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc      1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat      1056
Asn Ile Lys Lys Val Phe Gly Leu Asp Met Ala Gln Leu Leu Leu Asp
            340                 345                 350 gtc ctc tgt ttc gga aaa gac gcc gat ctg ccg gac gga tta ttg gat      1104
Val Leu Cys Phe Gly Lys Asp Ala Asp Leu Pro Asp Gly Leu Leu Asp
        355                 360                 365 caa gag cct tat tat gtt gcc gac tgc cat ttg tac ccg cag cat ttc      1152
Gln Glu Pro Tyr Tyr Val Ala Asp Cys His Leu Tyr Pro Gln His Phe
370                 375                 380 aaa caa aat ggc caa att cct gaa act gct gag gat ttg gtc att gaa      1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt      1248
Ala Ile Asp Ile Pro Asp Gly Leu Leu Lys Gly Asp Thr Glu Ile Val
                405                 410                 415 tct ttt tcg gcc gca gca cca ggc act tca gtt gat ttg aca ttg ttt      1296
Ser Phe Ser Ala Ala Ala Pro Gly Thr Ser Val Asp Leu Thr Leu Phe
            420                 425                 430
```

```
gaa gct ttc aat tcc att gct gca ttt gaa ctg aaa ggc agt aat tca    1344
Glu Ala Phe Asn Ser Ile Ala Ala Phe Glu Leu Lys Gly Ser Asn Ser
            435                 440                 445 cag gat gtg gct gaa tca atc aga caa att cag cag cat gcg aag ctg    1392
Gln Asp Val Ala Glu Ser Ile Arg Gln Ile Gln Gln His Ala Lys Leu
        450                 455                 460 acg gca aag tat gtg ctg cca gta                                    1416
Thr Ala Lys Tyr Val Leu Pro Val
465                 470

<210> SEQ ID NO 21
<211> LENGTH: 1416
<212> TYPE: DNA
<213> ORGANISM: Bacillus subtilis ATCC6633

<400> SEQUENCE: 21 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtt agc     96
Pro His Met Phe Tyr Lys Ser Ala Ala Glu Lys Tyr Asn Leu Val Ser
                20                  25                  30 ttt att ccg aga cct ttt gca ata aca gcc tcc cat gca gca ctg att    144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt cag agc    192
Glu Lys Tyr Ser Val Ala Val Ile Lys Asp Lys Asp Tyr Phe Gln Ser
        50                  55                  60 tta gct gat ttt gag cat ccc gat tca att tat tgg gcg cat gag gat    240
Leu Ala Asp Phe Glu His Pro Asp Ser Ile Tyr Trp Ala His Glu Asp
65                  70                  75                  80 cat gac aag cct gaa gaa gag gtt gtc gag caa atc gtc aag gtt gcc    288
His Asp Lys Pro Glu Glu Glu Val Val Glu Gln Ile Val Lys Val Ala
                85                  90                  95 caa atg ttt gag gcg gac gcc atc aca aca aac aat gaa tta ttc att    336
Gln Met Phe Glu Ala Asp Ala Ile Thr Thr Asn Asn Glu Leu Phe Ile
                100                 105                 110 gcc ccg atg gcg aaa gcc tgt gaa cgc ctt ggc ctg agg ggc gcc gga    384
Ala Pro Met Ala Lys Ala Cys Glu Arg Leu Gly Leu Arg Gly Ala Gly
            115                 120                 125 gtg cag gca gcg gaa aat gcc aga gat aaa aat aaa atg agg gac gct    432
Val Gln Ala Ala Glu Asn Ala Arg Asp Lys Asn Lys Met Arg Asp Ala
        130                 135                 140 ttt aat aag gcg gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctt gag gat ttt cgt gct gca ctt gaa gag atc ggc aca cct cta atc    528
Leu Glu Asp Phe Arg Ala Ala Leu Glu Glu Ile Gly Thr Pro Leu Ile
                165                 170                 175 tta aag cct aca tac tta gcg agt tca atc ggc gta acg ctg att acc    576
Leu Lys Pro Thr Tyr Leu Ala Ser Ser Ile Gly Val Thr Leu Ile Thr
            180                 185                 190 gac acg gag acg gca gaa gat gaa ttt aac aga gtc aat gac tac ctg    624
Asp Thr Glu Thr Ala Glu Asp Glu Phe Asn Arg Val Asn Asp Tyr Leu
        195                 200                 205 aaa tcg att aac gtg ccg aag gcg gtc aca ttt gaa gca ccg ttt att    672
Lys Ser Ile Asn Val Pro Lys Ala Val Thr Phe Glu Ala Pro Phe Ile
    210                 215                 220 gct gag gaa ttt tta cag ggt gag tac gga gac tgg tat caa aca gaa    720
Ala Glu Glu Phe Leu Gln Gly Glu Tyr Gly Asp Trp Tyr Gln Thr Glu
225                 230                 235                 240
```

| | | |
|---|---|---|
| ggg tac tcc gac tat atc agc ata gaa ggc att atg gca gat ggt gag<br>Gly Tyr Ser Asp Tyr Ile Ser Ile Glu Gly Ile Met Ala Asp Gly Glu<br>                        245                        250                        255 | 768 |
| tat ttt ccg atc gcc att cat gac aaa acg ccg caa att gga ttt aca<br>Tyr Phe Pro Ile Ala Ile His Asp Lys Thr Pro Gln Ile Gly Phe Thr<br>                        260                        265                        270 | 816 |
| gag aca tca cat att acg cca tcc att ctg gat gaa gag gcg aaa aag<br>Glu Thr Ser His Ile Thr Pro Ser Ile Leu Asp Glu Glu Ala Lys Lys<br>                275                        280                        285 | 864 |
| aaa att gtc gaa gcg gct aaa aag gca aat gaa ggg ctt gga ctg caa<br>Lys Ile Val Glu Ala Ala Lys Lys Ala Asn Glu Gly Leu Gly Leu Gln<br>      290                        295                        300 | 912 |
| aat tgc gca aca cat aca gaa atc aag cta atg aaa aac aga gaa ccg<br>Asn Cys Ala Thr His Thr Glu Ile Lys Leu Met Lys Asn Arg Glu Pro<br>305                        310                        315                        320 | 960 |
| ggt tta ata gag tcg gct gcc aga ttc gca ggc tgg aat atg att cct<br>Gly Leu Ile Glu Ser Ala Ala Arg Phe Ala Gly Trp Asn Met Ile Pro<br>                        325                        330                        335 | 1008 |
| aac att aaa aag gtt ttc ggc ctt gat atg gcg caa tta tta tta gat<br>Asn Ile Lys Lys Val Phe Gly Leu Asp Met Ala Gln Leu Leu Leu Asp<br>              340                        345                        350 | 1056 |
| gtt ctc tgt ttc gga aaa gat gct gat ctg ccg gac ggg tta ttg gat<br>Val Leu Cys Phe Gly Lys Asp Ala Asp Leu Pro Asp Gly Leu Leu Asp<br>        355                        360                        365 | 1104 |
| caa gag cct tac tat gtt gct gac tgc cat ctg tac cct cag cat ttc<br>Gln Glu Pro Tyr Tyr Val Ala Asp Cys His Leu Tyr Pro Gln His Phe<br>    370                        375                        380 | 1152 |
| aaa caa aat ggc cag atc cct gaa act gcc gag gat ttg gta atc gaa<br>Lys Gln Asn Gly Gln Ile Pro Glu Thr Ala Glu Asp Leu Val Ile Glu<br>385                        390                        395                        400 | 1200 |
| gcg atc gat att ccg gat ggg ctt ttg aag ggt gat aca gaa atc gtt<br>Ala Ile Asp Ile Pro Asp Gly Leu Leu Lys Gly Asp Thr Glu Ile Val<br>                        405                        410                        415 | 1248 |
| act ttt tcg gct gcg gca cca gga aca tca gtt gat ttg aca ctg ttt<br>Thr Phe Ser Ala Ala Ala Pro Gly Thr Ser Val Asp Leu Thr Leu Phe<br>              420                        425                        430 | 1296 |
| gaa gcc ttc aac tcc att gct gca ttt gaa ctg aaa ggc agc aat tca<br>Glu Ala Phe Asn Ser Ile Ala Ala Phe Glu Leu Lys Gly Ser Asn Ser<br>        435                        440                        445 | 1344 |
| cag gat gtg gct gaa tca atc aga caa att cag cag cat gcg aag ctg<br>Gln Asp Val Ala Glu Ser Ile Arg Gln Ile Gln Gln His Ala Lys Leu<br>    450                        455                        460 | 1392 |
| acg gca aag tat gtg ctg cca gta<br>Thr Ala Lys Tyr Val Leu Pro Val<br>465                        470 | 1416 |

```
<210> SEQ ID NO 22
<211> LENGTH: 1416
<212> TYPE: DNA
<213> ORGANISM: Bacillus subtilis IAM1213

<400> SEQUENCE: 22
```

| | | |
|---|---|---|
| atg gag aga aaa aca gta ttg gtc atc gct gat ctt gga ggc tgc ccg<br>Met Glu Arg Lys Thr Val Leu Val Ile Ala Asp Leu Gly Gly Cys Pro<br>1                  5                        10                        15 | 48 |
| ccg cac atg ttt tat aaa agc gct gct gaa aaa tat aac ctg gtc agc<br>Pro His Met Phe Tyr Lys Ser Ala Ala Glu Lys Tyr Asn Leu Val Ser<br>                    20                        25                        30 | 96 |
| ttt att cca aga cct ttt gca att aca gcc tcc cat gca gca ttg att<br>Phe Ile Pro Arg Pro Phe Ala Ile Thr Ala Ser His Ala Ala Leu Ile<br>               35                        40                        45 | 144 |

```
gaa aaa tac tcg gtc gcg gtc ata aaa gat aaa gac tat ttt aag agt    192
Glu Lys Tyr Ser Val Ala Val Ile Lys Asp Lys Asp Tyr Phe Lys Ser
    50              55                  60 tta gct gat ttt gag cat cct gac tcc att tat tgg gcg cat gag gat    240
Leu Ala Asp Phe Glu His Pro Asp Ser Ile Tyr Trp Ala His Glu Asp
65              70                  75                  80 cat aac aag cct gag gaa gag gtc gtc gag caa atc gtc aag gtt gcc    288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att    336
Glu Met Phe Gly Ala Asp Ala Ile Thr Thr Asn Asn Glu Leu Phe Ile
                    100                 105                 110 gct ccg atg gcg aaa gcc tgt gaa cgt ctg ggc ctg aga ggt gcc ggc    384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct    432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctc gaa gat ttc cgt gct gct ctt gaa gag atc ggc aca cct ctt atc    528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg    576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg    624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc    672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa    720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag    768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca    816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag    864
Glu Thr Ser His Ile Thr Pro Ser Ile Leu Asp Glu Glu Ala Lys Lys
        275                 280                 285 aaa att gtc gaa gct gcc aaa aag gca aat gaa ggt ctt ggc ctg caa    912
Lys Ile Val Glu Ala Ala Lys Lys Ala Asn Glu Gly Leu Gly Leu Gln
290                 295                 300 aat tgc gca aca cat aca gag atc aag cta atg aaa aat aga gaa ccg    960
Asn Cys Ala Thr His Thr Glu Ile Lys Leu Met Lys Asn Arg Glu Pro
305                 310                 315                 320 ggt tta att gaa tcg gca gcc aga ttc gcc ggc tgg aat atg atc ccc   1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat   1056
Asn Ile Lys Lys Val Phe Gly Leu Asp Met Ala Gln Leu Leu Leu Asp
            340                 345                 350 gtc ctt tgt ttc gga aaa gac gcc gat ctg ccg gac gga tta ttg gat   1104
Val Leu Cys Phe Gly Lys Asp Ala Asp Leu Pro Asp Gly Leu Leu Asp
        355                 360                 365
```

```
caa gag cct tat tat gtt gcc gac tgc cat ttg tac ccg caa cat ttc    1152
Gln Glu Pro Tyr Tyr Val Ala Asp Cys His Leu Tyr Pro Gln His Phe
    370                 375                 380 aaa caa aat ggc cag att cca gaa act gct gag gat ttg gtc att gaa    1200
Lys Gln Asn Gly Gln Ile Pro Glu Thr Ala Glu Asp Leu Val Ile Glu
385                 390                 395                 400 gcg atc gat ctg cct gac ggg ctt tta aaa ggg gat act gag atc gtt    1248
Ala Ile Asp Leu Pro Asp Gly Leu Leu Lys Gly Asp Thr Glu Ile Val
                405                 410                 415 tct ttt tcg gcc gca gca cca gga act tca gtt gat ttg aca ttg ttt    1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca    1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg    1392
Gln Asp Val Ala Glu Ser Ile Arg Gln Ile Gln Gln His Ala Lys Leu
    450                 455                 460 acg gca aag tat gtg ctg cca gta                                    1416
Thr Ala Lys Tyr Val Leu Pro Val
465                 470

<210> SEQ ID NO 23
<211> LENGTH: 1416
<212> TYPE: DNA
<213> ORGANISM: Bacillus subtilis IAM1107

<400> SEQUENCE: 23 atg gag aga aaa aca gta ttg gtc atc gct gat ctt gga ggc tgc ccg    48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc    96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att    144
Phe Ile Pro Arg Pro Phe Ala Ile Thr Ala Ser His Ala Ala Leu Ile
            35                  40                  45 gaa aaa tac tcg gtc gcg gtc gta aaa gat aaa gac tat ttt aag agt    192
Glu Lys Tyr Ser Val Ala Val Val Lys Asp Lys Asp Tyr Phe Lys Ser
        50                  55                  60 tta gct gat ttt gag cat cct gac tcc att tat tgg gcg cat gag gat    240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc    288
His Asn Lys Pro Glu Glu Glu Val Val Glu Gln Ile Val Lys Val Ala
                85                  90                  95 gaa atg ttc ggg gcg gat gcc atc aca aca aac aat gaa tta ttc att    336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ttg aga ggt gcc ggc    384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct    432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc    528
Leu Glu Asp Phe Arg Ala Ala Leu Glu Glu Ile Gly Thr Pro Leu Ile
                165                 170                 175
```

```
tta aag cct aca tac tta gcg agt tct atc ggt gta acg ctg att acg      576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc      672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt ggc ctg caa      912
Lys Ile Val Glu Ala Ala Lys Lys Ala Asn Glu Gly Leu Gly Leu Gln
    290                 295                 300 aat tgc gca aca cat aca gag gtc aag cta atg aaa aac aga gaa ccg      960
Asn Cys Ala Thr His Thr Glu Val Lys Leu Met Lys Asn Arg Glu Pro
305                 310                 315                 320 ggt tta att gaa tcg gca gcc aga ttt gcc ggc tgg aat atg atc cct     1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat     1056
Asn Ile Lys Lys Val Phe Gly Leu Asp Met Ala Gln Leu Leu Leu Asp
            340                 345                 350 gtc ctc tgt ttc gga aaa gat gcc gat ctg ccg gac gga tta ttg gat     1104
Val Leu Cys Phe Gly Lys Asp Ala Asp Leu Pro Asp Gly Leu Leu Asp
        355                 360                 365 caa gag cct tac tat gtc gcc gac tgc cat ttg tac ccg cag cat ttc     1152
Gln Glu Pro Tyr Tyr Val Ala Asp Cys His Leu Tyr Pro Gln His Phe
    370                 375                 380 aaa caa aat ggc cag att cca gaa acc gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc ttt     1248
Ala Ile Asp Ile Pro Asp Gly Leu Leu Lys Gly Asp Thr Glu Ile Phe
                405                 410                 415 tct ttt tcg gcc gca gca cca ggc act tca gtt gat ttg aca ttg ttt     1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
    450                 455                 460 acg gca aag tat gtg ctg cca gta                                     1416
Thr Ala Lys Tyr Val Leu Pro Val
465                 470

<210> SEQ ID NO 24
<211> LENGTH: 1416
<212> TYPE: DNA
```

<213> ORGANISM: Bacillus subtilis IAM1214

<400> SEQUENCE: 24

```
atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtt agc      96
Pro His Met Phe Tyr Lys Ser Ala Ala Glu Lys Tyr Asn Leu Val Ser
            20                  25                  30 ttt att ccg aga cct ttt gca ata aca gcc tcc cat gca gca ctg att     144
Phe Ile Pro Arg Pro Phe Ala Ile Thr Ala Ser His Ala Ala Leu Ile
        35                  40                  45 gaa aaa tac tcg gtc gcg gtc ata aaa gat aaa gac tat ttt cag agc     192
Glu Lys Tyr Ser Val Ala Val Ile Lys Asp Lys Asp Tyr Phe Gln Ser
    50                  55                  60 tta gct gat ttt gag cat ccc gat tca att tat tgg gcg cat gag gat     240
Leu Ala Asp Phe Glu His Pro Asp Ser Ile Tyr Trp Ala His Glu Asp
65                  70                  75                  80 cat gac aag cct gaa gaa gag gtt gtc gag caa atc gtc aag gtt gcc     288
His Asp Lys Pro Glu Glu Glu Val Val Glu Gln Ile Val Lys Val Ala
                85                  90                  95 caa atg ttt gag gcg gac gcc atc aca aca aac aat gaa tta ttc att     336
Gln Met Phe Glu Ala Asp Ala Ile Thr Thr Asn Asn Glu Leu Phe Ile
            100                 105                 110 gcc ccg atg gcg aaa gcc tgt gaa cgc ctt ggc ctg agg ggc gcc gga     384
Ala Pro Met Ala Lys Ala Cys Glu Arg Leu Gly Leu Arg Gly Ala Gly
        115                 120                 125 gtg cag gca gcg gaa aat gcc aga gat aaa aat aaa atg agg gac gct     432
Val Gln Ala Ala Glu Asn Ala Arg Asp Lys Asn Lys Met Arg Asp Ala
    130                 135                 140 ttt aat aag gcg gga gtc aaa tcg atc aaa aac aaa cga gtc aca act     480
Phe Asn Lys Ala Gly Val Lys Ser Ile Lys Asn Lys Arg Val Thr Thr
145                 150                 155                 160 ctt gag gat ttt cgt gct gca ctt gaa gag atc ggc aca cct cta atc     528
Leu Glu Asp Phe Arg Ala Ala Leu Glu Glu Ile Gly Thr Pro Leu Ile
                165                 170                 175 tta aag cct aca tac tta gcg agt tca atc ggc gta acg ctg att acc     576
Leu Lys Pro Thr Tyr Leu Ala Ser Ser Ile Gly Val Thr Leu Ile Thr
            180                 185                 190 gac acg gag acg gca gaa gat gaa ttt aac aga gtc aat gac tac ctg     624
Asp Thr Glu Thr Ala Glu Asp Glu Phe Asn Arg Val Asn Asp Tyr Leu
        195                 200                 205 aaa tcg att aac gtg ccg aag gcg gtc aca ttt gaa gca ccg ttt att     672
Lys Ser Ile Asn Val Pro Lys Ala Val Thr Phe Glu Ala Pro Phe Ile
    210                 215                 220 gct gag gaa ttt tta cag ggt gag tac gga gac tgg tat caa aca gaa     720
Ala Glu Glu Phe Leu Gln Gly Glu Tyr Gly Asp Trp Tyr Gln Thr Glu
225                 230                 235                 240 ggg tac tcc gac tat atc agc ata gaa ggc att atg gca gat ggt gag     768
Gly Tyr Ser Asp Tyr Ile Ser Ile Glu Gly Ile Met Ala Asp Gly Glu
                245                 250                 255 tat ttt ccg atc gcc att cat gac aaa acg ccg caa att gga ttt aca     816
Tyr Phe Pro Ile Ala Ile His Asp Lys Thr Pro Gln Ile Gly Phe Thr
            260                 265                 270 gag aca tca cat att acg cca tcc att ctg gat gaa gag gcg aaa aag     864
Glu Thr Ser His Ile Thr Pro Ser Ile Leu Asp Glu Glu Ala Lys Lys
        275                 280                 285 aaa att gtc gaa gcg gct aaa aag gca aat gaa ggg ctt gga ctg caa     912
Lys Ile Val Glu Ala Ala Lys Lys Ala Asn Glu Gly Leu Gly Leu Gln
    290                 295                 300
```

```
aat tgc gca aca cat aca gaa atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gct gcc aga ttc gca ggc tgg aat atg att cct     1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat     1056
Asn Ile Lys Lys Val Phe Gly Leu Asp Met Ala Gln Leu Leu Leu Asp
            340                 345                 350 gtt ctc tgt ttc gga aaa gat gct gat ctg ccg gac ggg tta ttg gat     1104
Val Leu Cys Phe Gly Lys Asp Ala Asp Leu Pro Asp Gly Leu Leu Asp
        355                 360                 365 caa gag cct tac tat gtt gct gac tgc cat ctg tac cct cag cat ttc     1152
Gln Glu Pro Tyr Tyr Val Ala Asp Cys His Leu Tyr Pro Gln His Phe
    370                 375                 380 aaa caa aat ggc cag atc cct gaa act gcc gag gat ttg gta atc gaa     1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt     1248
Ala Ile Asp Ile Pro Asp Gly Leu Leu Lys Gly Asp Thr Glu Ile Val
                405                 410                 415 act ttt tcg gct gcg gca cca gga aca tca gtt gat ttg aca ctg ttt     1296
Thr Phe Ser Ala Ala Ala Pro Gly Thr Ser Val Asp Leu Thr Leu Phe
            420                 425                 430 gaa gcc ttc aac tcc att gct gca ttt gaa ctg aaa ggc agc aat tca     1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
    450                 455                 460 acg gca aag tat gtg ctg cca gta                                      1416
Thr Ala Lys Tyr Val Leu Pro Val
465                 470

<210> SEQ ID NO 25
<211> LENGTH: 1416
<212> TYPE: DNA
<213> ORGANISM: Bacillus subtilis ATCC21555

<400> SEQUENCE: 25 atg gag aga aaa aca gta ttg gtt atc gct gat ctt ggg ggc tgc ccg       48
Met Glu Arg Lys Thr Val Leu Val Ile Ala Asp Leu Gly Gly Cys Pro
1               5                   10                  15 ccg cat atg ttt tac aaa agc gca gcc gaa aaa tac aac ctc gtc agc       96
Pro His Met Phe Tyr Lys Ser Ala Ala Glu Lys Tyr Asn Leu Val Ser
                20                  25                  30 ttt att ccg aga ccc ttt gca att aca gcc tct cat gcg gcc tta att      144
Phe Ile Pro Arg Pro Phe Ala Ile Thr Ala Ser His Ala Ala Leu Ile
            35                  40                  45 gaa aaa tac tcg att gcg gtc att aaa gat aaa gac tat ttt aag agt      192
Glu Lys Tyr Ser Ile Ala Val Ile Lys Asp Lys Asp Tyr Phe Lys Ser
        50                  55                  60 ctg gct gat ttt gaa cat ccc gat tcg att tat tgg gct cat gaa gat      240
Leu Ala Asp Phe Glu His Pro Asp Ser Ile Tyr Trp Ala His Glu Asp
65                  70                  75                  80 cat gac aaa cct gag gaa gaa gtc gtc gaa gaa atc gtg aaa gtg gcc      288
His Asp Lys Pro Glu Glu Glu Val Val Glu Glu Ile Val Lys Val Ala
                85                  90                  95 gac atg ttt ggg gtt gac gcc att acg acc aac aat gaa ctg ttt atc      336
Asp Met Phe Gly Val Asp Ala Ile Thr Thr Asn Asn Glu Leu Phe Ile
            100                 105                 110
```

```
gct ccg atg gca aaa gcg tgt aaa cgt ctc ggc ctg cgg gga gcg ggc      384
Ala Pro Met Ala Lys Ala Cys Lys Arg Leu Gly Leu Arg Gly Ala Gly
        115                 120                 125 gta cag gcc gct gaa aac gcc aga gat aaa aat aaa atg aga gcc gcc      432
Val Gln Ala Ala Glu Asn Ala Arg Asp Lys Asn Lys Met Arg Ala Ala
130                 135                 140 ttc aac cgg gcc ggc gtc aaa tcc atc aaa aac aaa cgg gtg acg acc      480
Phe Asn Arg Ala Gly Val Lys Ser Ile Lys Asn Lys Arg Val Thr Thr
145                 150                 155                 160 ctg gaa gat ttc cgc gcc gcg ctt cag gaa atc gga acg ccg ctt att      528
Leu Glu Asp Phe Arg Ala Ala Leu Gln Glu Ile Gly Thr Pro Leu Ile
                165                 170                 175 ctg aag cct aca tat ctg gca agc tcg atc ggc gtg acg ctt att aaa      576
Leu Lys Pro Thr Tyr Leu Ala Ser Ser Ile Gly Val Thr Leu Ile Lys
            180                 185                 190 gag atg gaa acg gcc gaa gct gaa ttc aac aga gtc aat gag tac ttg      624
Glu Met Glu Thr Ala Glu Ala Glu Phe Asn Arg Val Asn Glu Tyr Leu
        195                 200                 205 aaa tcg att aat gta ccg aaa gcg gtg acg ttt gaa gcg ccg ttt atc      672
Lys Ser Ile Asn Val Pro Lys Ala Val Thr Phe Glu Ala Pro Phe Ile
210                 215                 220 gcg gaa gaa ttc ttg cag ggc gag tat gat gac tgg tac gaa aca agc      720
Ala Glu Glu Phe Leu Gln Gly Glu Tyr Asp Asp Trp Tyr Glu Thr Ser
225                 230                 235                 240 ggt tat tcc gac tat atc agc atc gaa ggc atc atg gcc gac gga gaa      768
Gly Tyr Ser Asp Tyr Ile Ser Ile Glu Gly Ile Met Ala Asp Gly Glu
                245                 250                 255 tac ttc ccc gtt gcg atc cat gat aaa aca ccg caa atc gga ttc acg      816
Tyr Phe Pro Val Ala Ile His Asp Lys Thr Pro Gln Ile Gly Phe Thr
            260                 265                 270 gag aca gcg cat att acg ccg tcc atc ctg gat gat gac gcc aag cgg      864
Glu Thr Ala His Ile Thr Pro Ser Ile Leu Asp Asp Asp Ala Lys Arg
        275                 280                 285 aaa atc gtc gaa gct gcc aag aag gcg aat gaa gga ctc ggc ctc gaa      912
Lys Ile Val Glu Ala Ala Lys Lys Ala Asn Glu Gly Leu Gly Leu Glu
290                 295                 300 aac tgt gca acg cat aca gaa ata aaa tta atg aaa aac cgg gaa gcc      960
Asn Cys Ala Thr His Thr Glu Ile Lys Leu Met Lys Asn Arg Glu Ala
305                 310                 315                 320 gga ctg att gag tca gcg gcc aga ttc gcg gga tgg aat atg att ccg     1008
Gly Leu Ile Glu Ser Ala Ala Arg Phe Ala Gly Trp Asn Met Ile Pro
                325                 330                 335 aat att aaa aag gtc ttc ggc gtt gat atg gcg cag cta tta ttg gat     1056
Asn Ile Lys Lys Val Phe Gly Val Asp Met Ala Gln Leu Leu Leu Asp
            340                 345                 350 gtt ctc tgt tac gga aaa gaa gct gat ctg ccg aaa gga tta ttg gag     1104
Val Leu Cys Tyr Gly Lys Glu Ala Asp Leu Pro Lys Gly Leu Leu Glu
        355                 360                 365 cag gag cca tgc tat gtc gca gac tgc cac ttg tat cct cag cat ttc     1152
Gln Glu Pro Cys Tyr Val Ala Asp Cys His Leu Tyr Pro Gln His Phe
370                 375                 380 aaa gag aac ggc cag ctg cct gag acg gtt gtc gat ttc gtc att gaa     1200
Lys Glu Asn Gly Gln Leu Pro Glu Thr Val Val Asp Phe Val Ile Glu
385                 390                 395                 400 agc att gaa att cct gac ggc gtc tta aag gga gac act gaa ctc gtt     1248
Ser Ile Glu Ile Pro Asp Gly Val Leu Lys Gly Asp Thr Glu Leu Val
                405                 410                 415 tct ttc tca gcg gct gag gcg ggt acg tca gtg gat ctg cgg ctg ttc     1296
Ser Phe Ser Ala Ala Glu Ala Gly Thr Ser Val Asp Leu Arg Leu Phe
            420                 425                 430
```

```
gaa gcg ttc aac agc att gcg gcg ttt gag ctg aaa gga agc aat tcg      1344
Glu Ala Phe Asn Ser Ile Ala Ala Phe Glu Leu Lys Gly Ser Asn Ser
    435                 440                 445 aac gac gtg gcc gaa tca atc aaa caa att cag cag cag gcg aag ctg      1392
Asn Asp Val Ala Glu Ser Ile Lys Gln Ile Gln Gln Gln Ala Lys Leu
450                 455                 460 act gca aag tat gcg tta tcg gta                                      1416
Thr Ala Lys Tyr Ala Leu Ser Val
465                 470

<210> SEQ ID NO 26
<211> LENGTH: 1416
<212> TYPE: DNA
<213> ORGANISM: Bacillus amyloliquefaciens IFO3022

<400> SEQUENCE: 26 atg gag aga aaa aca gta ttg gtt atc gct gac ctt ggg gga tgc ccg       48
Met Glu Arg Lys Thr Val Leu Val Ile Ala Asp Leu Gly Gly Cys Pro
1               5                   10                  15 ccg cat atg ttt tac aaa agc gca gcc gaa aaa tac aac ctc gtc agc       96
Pro His Met Phe Tyr Lys Ser Ala Ala Glu Lys Tyr Asn Leu Val Ser
                20                  25                  30 ttt att ccg aga cct ttt gca att aca gcc tct cat gcg gca tta att      144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt aag agt      192
Glu Lys Tyr Ser Val Ala Val Ile Lys Asp Lys Asp Tyr Phe Lys Ser
    50                  55                  60 ctg gct gat ttt gag cat ccc gat tcg att tac tgg gct cat gaa gat      240
Leu Ala Asp Phe Glu His Pro Asp Ser Ile Tyr Trp Ala His Glu Asp
65                  70                  75                  80 cat gac aaa cct gag gaa gaa gta gtc gaa gaa atc gtc aag gtg gcc      288
His Asp Lys Pro Glu Glu Glu Val Val Glu Glu Ile Val Lys Val Ala
                85                  90                  95 ggc atg ttc gcg gtt gac gcc att acg acc aac aat gaa ctg ttt atc      336
Gly Met Phe Ala Val Asp Ala Ile Thr Thr Asn Asn Glu Leu Phe Ile
                100                 105                 110 gct ccg atg gca aaa gcg tgt gaa cgt ctc ggc ctg cgg gga gcg ggc      384
Ala Pro Met Ala Lys Ala Cys Glu Arg Leu Gly Leu Arg Gly Ala Gly
            115                 120                 125 gta cag gcc gct gaa aat gcc aga gat aaa aac aaa atg aga gcc gct      432
Val Gln Ala Ala Glu Asn Ala Arg Asp Lys Asn Lys Met Arg Ala Ala
    130                 135                 140 ttc aac cgg gcc ggc gtc aag tct atc aaa aac aga cgg gtg acg acg      480
Phe Asn Arg Ala Gly Val Lys Ser Ile Lys Asn Arg Arg Val Thr Thr
145                 150                 155                 160 ctg gaa gat ttc cgc gcc gcg ctt cag gaa atc gga acg ccg ctc att      528
Leu Glu Asp Phe Arg Ala Ala Leu Gln Glu Ile Gly Thr Pro Leu Ile
                165                 170                 175 ctg aag cct aca tat ctg gcg agc tcc atc ggc gtg acg ctc atc aaa      576
Leu Lys Pro Thr Tyr Leu Ala Ser Ser Ile Gly Val Thr Leu Ile Lys
                180                 185                 190 gag agg gaa acg gcc gaa gcc gaa ttt aac aga gtc aat gaa tac ctg      624
Glu Arg Glu Thr Ala Glu Ala Glu Phe Asn Arg Val Asn Glu Tyr Leu
            195                 200                 205 aag tcg atc aac gta ccg aaa gcg gtc acg ttt gaa gcg ccg ttt atc      672
Lys Ser Ile Asn Val Pro Lys Ala Val Thr Phe Glu Ala Pro Phe Ile
    210                 215                 220 gcg gaa gaa ttt ttg cag ggc gag tat gac gac tgg tac gaa aca agc      720
Ala Glu Glu Phe Leu Gln Gly Glu Tyr Asp Asp Trp Tyr Glu Thr Ser
225                 230                 235                 240
```

```
ggt tat tcc gac tat atc agc ata gaa ggc atc atg gcc gac gga gaa      768
Gly Tyr Ser Asp Tyr Ile Ser Ile Glu Gly Ile Met Ala Asp Gly Glu
            245                 250                 255 tac ttc cct gtc gca att cat gat aaa aca ccg caa atc gga ttc acg      816
Tyr Phe Pro Val Ala Ile His Asp Lys Thr Pro Gln Ile Gly Phe Thr
        260                 265                 270 gag aca tcg cat att acg ccg tcc atc ctg gat gat gac gcg aag cgg      864
Glu Thr Ser His Ile Thr Pro Ser Ile Leu Asp Asp Asp Ala Lys Arg
    275                 280                 285 aaa atc gtc gaa gca gcc aaa aag gcg aat gaa gga ctc ggc ctc gaa      912
Lys Ile Val Glu Ala Ala Lys Lys Ala Asn Glu Gly Leu Gly Leu Glu
290                 295                 300 aac tgc gca acc cat aca gag att aaa tta atg aaa aac cgg gaa gcc      960
Asn Cys Ala Thr His Thr Glu Ile Lys Leu Met Lys Asn Arg Glu Ala
305                 310                 315                 320 gga ctg att gaa tca gcg gca cga ttt gcg ggc tgg aac atg att ccg     1008
Gly Leu Ile Glu Ser Ala Ala Arg Phe Ala Gly Trp Asn Met Ile Pro
            325                 330                 335 aat att aaa aag gtc ttc ggc gtc gat atg gcg cag ctg tta ttg gat     1056
Asn Ile Lys Lys Val Phe Gly Val Asp Met Ala Gln Leu Leu Leu Asp
        340                 345                 350 gtt ctc tgt ttc gga aaa gaa gcc gat ctg ccg aaa gga tta ttg gag     1104
Val Leu Cys Phe Gly Lys Glu Ala Asp Leu Pro Lys Gly Leu Leu Glu
    355                 360                 365 cag gag ccg tgc tat gtc gcc gac tgc cac ttg tat cct cag cat ttc     1152
Gln Glu Pro Cys Tyr Val Ala Asp Cys His Leu Tyr Pro Gln His Phe
370                 375                 380 aaa gag aac ggc cag ctg cct gag acg gct gtc gat ttc gtc att gaa     1200
Lys Glu Asn Gly Gln Leu Pro Glu Thr Ala Val Asp Phe Val Ile Glu
385                 390                 395                 400 agc att gac att ccc gac ggc gtc tta aag gga gac acc gaa atc gtt     1248
Ser Ile Asp Ile Pro Asp Gly Val Leu Lys Gly Asp Thr Glu Ile Val
            405                 410                 415 tct ttc tcg gcg gcc gag gcg ggt aca tcc gtg gat ctg cgg ctg ttc     1296
Ser Phe Ser Ala Ala Glu Ala Gly Thr Ser Val Asp Leu Arg Leu Phe
        420                 425                 430 gaa gcg ttc aac agc att gcg gcg ttc gag ctg aaa gga agc aat tcg     1344
Glu Ala Phe Asn Ser Ile Ala Ala Phe Glu Leu Lys Gly Ser Asn Ser
    435                 440                 445 ggt gac gtg gcc gaa tca atc aaa caa att cag cag cag gcg aag ctg     1392
Gly Asp Val Ala Glu Ser Ile Lys Gln Ile Gln Gln Gln Ala Lys Leu
450                 455                 460 act gca aag tat gcg tta ccg gta                                     1416
Thr Ala Lys Tyr Ala Leu Pro Val
465                 470

<210> SEQ ID NO 27
<211> LENGTH: 1428
<212> TYPE: DNA
<213> ORGANISM: Bacillus pumilus NRRL B-12025

<400> SEQUENCE: 27 gtg ctt tca ttg agt aaa aaa act gta ctt gtc att gct gac tta gga       48
Val Leu Ser Leu Ser Lys Lys Thr Val Leu Val Ile Ala Asp Leu Gly
1               5                   10                  15 ggg tgc ccg ccc cat atg ttt tat gaa agc gtg gcg gca tca tac cat       96
Gly Cys Pro Pro His Met Phe Tyr Glu Ser Val Ala Ala Ser Tyr His
            20                  25                  30 atc gtt tct tat atc cca aga ccc ttt gcg att aca aag gga cat gcc      144
Ile Val Ser Tyr Ile Pro Arg Pro Phe Ala Ile Thr Lys Gly His Ala
        35                  40                  45
```

```
gag cta atc gaa aaa tac tcc att gcc gtc atc aaa gac cgt gat tat    192
Glu Leu Ile Glu Lys Tyr Ser Ile Ala Val Ile Lys Asp Arg Asp Tyr
     50                  55                  60 ttt gag aca cac cct tct ttt gaa cac cct gat tct att tac tgg gca    240
Phe Glu Thr His Pro Ser Phe Glu His Pro Asp Ser Ile Tyr Trp Ala
65                  70                  75                  80 cat gat gat tat cca aaa tca gaa gaa gaa gtt gtg gaa gac ttc att    288
His Asp Asp Tyr Pro Lys Ser Glu Glu Glu Val Val Glu Asp Phe Ile
                    85                  90                  95 cga gta gct tcc ttt ttc aaa gca gat gca atc acg acc aat aat gaa    336
Arg Val Ala Ser Phe Phe Lys Ala Asp Ala Ile Thr Thr Asn Asn Glu
                100                 105                 110 tta ttc att gca ccg atg gca aag gcc gct gaa cgt ctt ggg cta cga    384
Leu Phe Ile Ala Pro Met Ala Lys Ala Ala Glu Arg Leu Gly Leu Arg
            115                 120                 125 ggt gcc ggt gtc aag gca gcc gaa atg gcg cgt gat aaa agc caa atg    432
Gly Ala Gly Val Lys Ala Ala Glu Met Ala Arg Asp Lys Ser Gln Met
130                 135                 140 agg gct gca ttc aat gcc tct ggc gtc aaa gcg gtg aaa act cag cct    480
Arg Ala Ala Phe Asn Ala Ser Gly Val Lys Ala Val Lys Thr Gln Pro
145                 150                 155                 160 gtc acg act tta tct gat ttc caa caa gcc att gag tct atc gga aca    528
Val Thr Thr Leu Ser Asp Phe Gln Gln Ala Ile Glu Ser Ile Gly Thr
                165                 170                 175 ccg ctc att tta aag cct aca tat tta gcc agt tct att ggc gtc acc    576
Pro Leu Ile Leu Lys Pro Thr Tyr Leu Ala Ser Ser Ile Gly Val Thr
                180                 185                 190 ttg ttt cat gac aaa gcc gga agt gat gac ttg ttt caa gta caa        624
Leu Phe His Asp Lys Ala Gly Ser Asp Asp Leu Phe Gln Val Gln
            195                 200                 205 tcg tat ttg gaa acc ata cca gtc cca gac gct gtc acg tat gaa gca    672
Ser Tyr Leu Glu Thr Ile Pro Val Pro Asp Ala Val Thr Tyr Glu Ala
210                 215                 220 ccg ttt gtc gct gaa aca tat tta gag ggt gct tac gaa gat tgg tat    720
Pro Phe Val Ala Glu Thr Tyr Leu Glu Gly Ala Tyr Glu Asp Trp Tyr
225                 230                 235                 240 gaa gac gaa gga tat gct gat tat gtc agt gta gaa ggg ctg gtc gta    768
Glu Asp Glu Gly Tyr Ala Asp Tyr Val Ser Val Glu Gly Leu Val Val
                245                 250                 255 gag ggc gaa tat ctc cct ttt gtc ata cat gat aaa acc cct caa atc    816
Glu Gly Glu Tyr Leu Pro Phe Val Ile His Asp Lys Thr Pro Gln Ile
                260                 265                 270 ggc ttt aca gaa acg gct cat atc act ccg acg atc tta gac aat gaa    864
Gly Phe Thr Glu Thr Ala His Ile Thr Pro Thr Ile Leu Asp Asn Glu
            275                 280                 285 gcc aag caa atc atc att gaa gca gca agg aag gca aat gaa ggg cta    912
Ala Lys Gln Ile Ile Ile Glu Ala Ala Arg Lys Ala Asn Glu Gly Leu
            290                 295                 300 ggt ctt gaa cat tgt gca acc cat aca gaa atc aaa ctc atg aaa aat    960
Gly Leu Glu His Cys Ala Thr His Thr Glu Ile Lys Leu Met Lys Asn
305                 310                 315                 320 cga gaa act gga ctg atc gag gca gcg gct cga ttc gct ggc tgg aat    1008
Arg Glu Thr Gly Leu Ile Glu Ala Ala Ala Arg Phe Ala Gly Trp Asn
                325                 330                 335 atg atc ccg aat att aaa aaa gtc ttt ggc gtc gat atg gcg aag cta    1056
Met Ile Pro Asn Ile Lys Lys Val Phe Gly Val Asp Met Ala Lys Leu
                340                 345                 350 ttg att gat gta tta gtt gat ggt aaa aag gct gta ctg cca aaa cag    1104
Leu Ile Asp Val Leu Val Asp Gly Lys Lys Ala Val Leu Pro Lys Gln
            355                 360                 365
```

```
ctg ctt tct gga cat aca ttt tat gta gcg gac tgc cac ctg tac cct       1152
Leu Leu Ser Gly His Thr Phe Tyr Val Ala Asp Cys His Leu Tyr Pro
    370             375                 380 cag cat ttt aaa gag agt ggg ctt atc ccg cct gaa gcc aca cat att       1200
Gln His Phe Lys Glu Ser Gly Leu Ile Pro Pro Glu Ala Thr His Ile
385             390                 395                 400 acc att gat cat gtg tct att ccg cag gaa gca ttc gtt gga gat act       1248
Thr Ile Asp His Val Ser Ile Pro Gln Glu Ala Phe Val Gly Asp Thr
            405                 410                 415 gcg att gtc agt caa tca ttc cct gcc aaa ggg act att gtg gat ctt       1296
Ala Ile Val Ser Gln Ser Phe Pro Ala Lys Gly Thr Ile Val Asp Leu
        420                 425                 430 gaa tta ttt gaa gct ttt aat gga atc gta tct ctt gaa tta aaa gga       1344
Glu Leu Phe Glu Ala Phe Asn Gly Ile Val Ser Leu Glu Leu Lys Gly
    435                 440                 445 tca tcc tca caa gat gtt gcc gcg tcc atc cgc aac att cag aaa cag       1392
Ser Ser Ser Gln Asp Val Ala Ala Ser Ile Arg Asn Ile Gln Lys Gln
450                 455                 460 gca acg att cag tta atg gat gaa tta gtg aag gga                       1428
Ala Thr Ile Gln Leu Met Asp Glu Leu Val Lys Gly
465                 470                 475

<210> SEQ ID NO 28
<211> LENGTH: 1416
<212> TYPE: DNA
<213> ORGANISM: Bacillus subtilis ATCC 15245 and Bacillus subtilis
      IAM 1033

<400> SEQUENCE: 28 atg gag aga aaa aca gta ttg gtc atc gct gat ctt gga ggc tgc ccg        48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc        96
Pro His Met Phe Tyr Lys Ser Ala Ala Glu Lys Tyr Asn Leu Val Ser
            20                  25                  30 ttt att cca aga cct ttt gca att aca gcc tcc cat gca gca ttg att       144
Phe Ile Pro Arg Pro Phe Ala Ile Thr Ala Ser His Ala Ala Leu Ile
        35                  40                  45 gaa aaa tac tcg gtc gcg gtc ata aaa gat aaa gac tat ttt aag agt       192
Glu Lys Tyr Ser Val Ala Val Ile Lys Asp Lys Asp Tyr Phe Lys Ser
    50                  55                  60 tta gct gat ttt gag cat cct gat tcc att tat tgg gcg cat gag gat       240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc       288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att       336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ctg aga ggt gcc ggc       384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct       432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act       480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc       528
Leu Glu Asp Phe Arg Ala Ala Leu Glu Glu Ile Gly Thr Pro Leu Ile
                165                 170                 175
```

```
tta aag cct aca tac tta gcg agt tca atc ggt gta acg ctg att acg       576
Leu Lys Pro Thr Tyr Leu Ala Ser Ser Ile Gly Val Thr Leu Ile Thr
        180                 185                 190 gac act gag acg gca gaa gat gaa ttt aac aga gtc aat gac tat ctg       624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc       672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa       720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag       768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca       816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag       864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt ggc ctg caa       912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg       960
Asn Cys Ala Thr His Thr Glu Ile Lys Leu Met Lys Asn Arg Glu Pro
305                 310                 315                 320 ggt tta ata gag tcg gca gcc aga ttc gca ggc tgg aat atg att cct      1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat      1056
Asn Ile Lys Lys Val Phe Gly Leu Asp Met Ala Gln Leu Leu Leu Asp
            340                 345                 350 gtc ctc tgt ttc gga aaa gac gcc gat ctg ccg gac gga tta ttg gat      1104
Val Leu Cys Phe Gly Lys Asp Ala Asp Leu Pro Asp Gly Leu Leu Asp
        355                 360                 365 caa gag cct tat tat gtt gcc gac tgc cat ttg tac ccg cag cat ttc      1152
Gln Glu Pro Tyr Tyr Val Ala Asp Cys His Leu Tyr Pro Gln His Phe
370                 375                 380 aaa caa aat ggc cag att cca gaa acc gct gag gat ttg gtc att gaa      1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt      1248
Ala Ile Asp Ile Pro Asp Gly Leu Leu Lys Gly Asp Thr Glu Ile Val
                405                 410                 415 tca ttt tca gcc gca gca cca ggc act tca gtt gat ttg aca ttg ttt      1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca      1344
Glu Ala Phe Asn Ser Ile Ala Ala Phe Glu Leu Lys Gly Ser Asn Ser
        435                 440                 445 cag gat gtg gct gaa tca atc aga caa att cag cag cat gca aag ctg      1392
Gln Asp Val Ala Glu Ser Ile Arg Gln Ile Gln Gln His Ala Lys Leu
450                 455                 460 acg gca aag tat gtg ctg cca gta                                      1416
Thr Ala Lys Tyr Val Leu Pro Val
465                 470

<210> SEQ ID NO 29
<211> LENGTH: 279
```

<212> TYPE: DNA
<213> ORGANISM: Bacillus subtilis 168

<400> SEQUENCE: 29

```
ggt gcc ggc gtg cag gca gcc gaa aat gcc aga gat aaa aat aaa atg      48
Gly Ala Gly Val Gln Ala Ala Glu Asn Ala Arg Asp Lys Asn Lys Met
1               5                   10                  15 agg gac gct ttt aat aag gcc gga gtc aaa tcg atc aaa aac aaa cga      96
Arg Asp Ala Phe Asn Lys Ala Gly Val Lys Ser Ile Lys Asn Lys Arg
            20                  25                  30 gtc aca act ctt gaa gat ttc cgt gct gct ctt gaa gag atc ggc aca     144
Val Thr Thr Leu Glu Asp Phe Arg Ala Ala Leu Glu Glu Ile Gly Thr
        35                  40                  45 cct ctt atc tta aag cct aca tac tta gcg agt tct atc ggt gta acg     192
Pro Leu Ile Leu Lys Pro Thr Tyr Leu Ala Ser Ser Ile Gly Val Thr
50                  55                  60 ctg att acg gac act gag acg gca gaa gat gaa ttt aac aga gtc aat     240
Leu Ile Thr Asp Thr Glu Thr Ala Glu Asp Glu Phe Asn Arg Val Asn
65                  70                  75                  80 gac tat ctg aaa tca att aac gtg cca aag gcg gtt acg                 279
Asp Tyr Leu Lys Ser Ile Asn Val Pro Lys Ala Val Thr
                85                  90
```

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
tttaagcttt gactttcagg agcccgttg                                     29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
tttgagctca tatatcgggg gaatgatag                                     29

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
tttaagctta aaggtgttc acgtgcaga                                      29

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
tttggatcct tagcgggatg ctcgttgca                                     29

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
atagaattct taacagttga ttcgttagtc                                        30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
ataggatcct caacaaagcg cgggctgccc                                        30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
tttgaattcg gtgataatga aaaggcaaag                                        30

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
tttctgcagt taaacgggct gcccctgat                                         29

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
tttgaattcg ttgttgaggc acatcttaa                                         29

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
tttctgcagt tattccgaca caactggct                                         29

```
<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
atggagttta gtgtaaaaag cggtagcccg gagaaagtgt aggctggagc tgcttc          56

<210> SEQ ID NO 41
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
ttactcttcg ccgttaaacc cagcgcggtt taacagcata tgaatatcct ccttag          56

<210> SEQ ID NO 42
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
catcatggat atttcacgat aacgttaagt tgcaccgtgt aggctggagc tgcttc          56

<210> SEQ ID NO 43
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
agatgccgga ggaggttgta acatcctccg gctacccata tgaatatcct ccttag          56

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
gttgagcggc tgccagagcc tttagccgag gaatcagtgt aggctggagc tgcttc          56

<210> SEQ ID NO 45
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
ctgccagctt gcccgcacca gttcacgctc tgcggtcata tgaatatcct ccttag          56

<210> SEQ ID NO 46
<211> LENGTH: 56
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
ctggacgatg tccgcgaagc actggccgaa gtcggtgtgt aggctggagc tgcttc        56

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
tgccgcgtcg tcctcttcac cggtacggat gcgaatcata tgaatatcct ccttag        56
```